US007641908B2

(12) United States Patent
Kinney et al.

(10) Patent No.: US 7,641,908 B2
(45) Date of Patent: Jan. 5, 2010

(54) DENGUE SEROTYPE 2 ATTENUATED STRAIN

(75) Inventors: Richard Kinney, Fort Collins, CO (US); Claire Y. H. Kinney, Fort Collins, CO (US); Véronique Barban, Craponne (FR); Jean Lang, Mions (FR); Bruno Guy, Lyons (FR)

(73) Assignees: Sanofi Pasteur, Lyons (FR); Center for Disease Control and Prevention, Atlanta, GA (US)

( * ) Notice: Subject to any disclaimer, the term of this patent is extended or adjusted under 35 U.S.C. 154(b) by 146 days.

(21) Appl. No.: 11/453,344

(22) Filed: Jun. 15, 2006

(65) Prior Publication Data

US 2007/0026016 A1 Feb. 1, 2007

Related U.S. Application Data

(60) Provisional application No. 60/691,274, filed on Jun. 17, 2005.

(51) Int. Cl.
*A61K 39/12* (2006.01)

(52) U.S. Cl. ................................ 424/218.1; 424/186.1

(58) Field of Classification Search ...................... None
See application file for complete search history.

(56) References Cited

U.S. PATENT DOCUMENTS

2004/0137013 A1 7/2004 Katinger et al.

FOREIGN PATENT DOCUMENTS

| | | |
|---|---|---|
| EP | 1 159 968 | 12/2001 |
| WO | WO-96/40933 | 12/1996 |
| WO | WO-00/57907 | 10/2000 |
| WO | WO-02/095075 | 11/2002 |
| WO | WO-03/092592 | 11/2003 |

OTHER PUBLICATIONS

Gowen et al., Antiviral Research, 2008, 78:79-90.*
Sanchez et al. Vaccine, 2006, 24:4914-4926.*
Kinney et al, "Development of new vaccine against dengue fever and Japanese encephalitis", 2001, pp. 176-197, vol. 44, Intervirology.
Kinney et al, "Construction of Infectious cDNA for Dengue 2 Virus: Strain 16681 and its attenuated Vaccine Derivative, Strain PDK-53", Apr. 14, 1997, pp. 300-308, vol. 230, No. 2, Academic Press Orlando, Florida, USA.
Butrapet et al, "Attenuation markers of a candidate dengue type 2 vaccine virus, strain 16681 (PDK-53), are defined by mutations in the 5' noncoding region and nonstructural proteins 1 and 3", Apr. 2000, pp. 3011-3019, vol. 74, No. 7, Journal of Virology, The American Society for Microbiology, USA.
Putnak et al, "Development of a purified, inactivated, dengue-2 virus vaccine prototype in vero cells: Immunogenicity and protection in mice and rhesus monkeys", Dec. 1996, pp. 1176-1184, vol. 174, No. 6, Journal of Infectious Diseases, Chicago, IL, USA.
Montagnon et al, "Experience with vero cells at Pasteur merieux connaught developments in biological standardization", 1997, pp. 137-140, vol. 98, Developments in Biological Standardization, Karger, Basel, CH.

* cited by examiner

*Primary Examiner*—Stacy B Chen
(74) *Attorney, Agent, or Firm*—B. Aaron Schulman; Terry L. Wright; Stites & Harbison PLLC

(57) ABSTRACT

The invention relates to live attenuated VDV2 (VERO-Derived Vaccine Dengue serotype 2) strains which have been derived from the wild-type dengue-2 strain 16681 by passaging on PDK and Vero cells. The invention further relates to a vaccine composition which comprises a VDV2 strain.

10 Claims, 6 Drawing Sheets

| Box | Label |
|---|---|
| Den2-16681/6PDK50 | LAV-2 pre-master P0 |
| TV100 | Transfection on Vero cells FPr/6 transf D09 P1 |
| LST 003 LST007 | Amplifications P2 to P4 |
| Clone 71 Clone 72 Clone 73 | Plaque Purification 1 P5 |
| Clone 721 Clone 722 | Plaque Purification 2 P6 |
| Clone 722 | Amplification 1 P7 |
| TV 722 | Amplification 2 P8 |
| VDV2 | Adaptation passages P9 to P11 |

strain 16681 (Day7)

VDV2 (Day 7)

LAV2 (Day 7)

| | | |
|---|---|---|
| WT dengue 2: | 1.5 to 2.5 mm | (95%) |
| LAV2/PDK50 : | <0.6 mm : 82% and <0.4 mm: | 82% |
| | 1 to 2 mm: | 12% |
| VDV2, passage 9: | <0.6 mm : 22% and <0.4 mm: | 16% |
| | 1 to 2 mm: | 68% |
| VDV2, passage 11: | <0.6 mm : 81% and <0.4 mm: | 57% |
| | 1 to 2 mm: | 12% |

Legend:
- VDV2 passage 9 (325 plaques)
- VDV2 passage 11 (500 plaques)
- WT2 16681 (94 plaques)
- LAV2/PDK50 (95 plaques)

X-axis: Plaque diameter (mm)
Y-axis: % population

DENGUE SEROTYPE 2 ATTENUATED STRAIN

CROSS-REFERENCE TO RELATED APPLICATIONS

The present application claims the benefit of U.S. provisional application 60/691,274, filed on Jun. 17, 2005, incorporated herein by reference.

The invention relates to new live attenuated VDV2 (VERO-Derived Dengue serotype 2 virus) strains which are derived from the wild-type dengue-2 strain 16681 by passaging on PDK and Vero cells sanitization. The invention further relates to a vaccine composition which comprises such VDV2 strain.

Dengue diseases are caused by four closely related, but antigenically distinct, virus serologic types (Gubler, 1988; Kautner et al., 1997; Rigau-Pérez et al., 1998; Vaughn et al., 1997), of the genus *Flavivirus* (Gubler, 1988). Infection with a dengue virus serotype can produce a spectrum of clinical illnesses ranging from a non-specific viral syndrome to severe, fatal haemorrhagic disease. The incubation period of dengue fever (DF) after the mosquito bite averages 4 days (range 3-14 days). DF is characterised by biphasic fever, headache, pain in various parts of the body, prostration, rash, lymphadenopathy and leukopenia (Kautner et al., 1997; Rigau-Pérez et al., 1998). The viremic period is the same as of febrile illness (Vaughn et al., 1997). Recovery from DF is usually complete in 7 to 10 days but prolonged asthenia is common. Leukocytes and platelets counts decreases are frequent.

Dengue haemorrhagic fever (DHF) is a severe febrile disease characterised by abnormalities of homeostasis and increased vascular permeability that can lead to hypovolemia and hypotension (dengue shock syndrome, DSS) often complicated by severe internal bleeding. The case fatality rate of DHF can be as high as 10% without therapy, but below 1% in most centres with therapeutic experience (WHO Technical Guide, 1986).

Routine laboratory diagnosis of dengue infections are based on virus isolation and/or the detection of dengue virus-specific antibodies.

Dengue disease is the second most important tropical infectious disease after malaria, with over half of the world's population (2.5 billion) living in areas at risk for epidemic transmission. An estimated 50 to 100 million cases of dengue, 500,000 hospitalised DHF patients and 25,000 deaths occur each year. Dengue is endemic in Asia, the Pacific, Africa, Latin America, and the Caribbean. More than 100 tropical countries have endemic dengue virus infections, and DHF have been documented in more than 60 of these (Gubler, 2002; Monath, 1994). A number of well described factors appear to be involved in dengue infections: population growth, unplanned and uncontrolled urbanisation particularly in association with poverty, increased air travel, lack of effective mosquito control, and the deterioration of sanitary and public health infrastructure (Gubler, 2002). The awareness of dengue in travellers and expatriates is increasing (Shirtcliffe et al., 1998). Dengue has proven to be a major cause of febrile illness among US troops during deployments in dengue-endemic tropical areas (DeFraites et al., 1994).

The viruses are maintained in a cycle that involves humans and *Aedes aegypti*, a domestic, day-biting mosquito that prefers to feed on humans. Human infection is initiated by the injection of virus during blood feeding by an infected *Aedes aegypti* mosquito. Salivary virus is deposited mainly in the extravascular tissues. The primary cell subset infected after inoculation is dendritic cells, which subsequently migrate to draining lymph nodes (Wu et al., 2000). After initial replication in the skin and draining lymph nodes, virus appears in the blood during the acute febrile phase, generally for 3 to 5 days.

Monocytes and macrophages are with dendritic cells among the primary target of dengue virus. Protection against homotypic reinfection is complete and probably lifelong, but cross-protection between dengue types lasts less than 12 weeks (Sabin, 1952). Consequently a subject can experience a second infection with a different serotype. A second dengue infection is a theoretical risk factor of developing severe dengue disease. However, DHF is multifactorial including: the strain of the virus involved, as well as the age, immune status, and genetic predisposition of the patient. Two factors play a major role in the occurrence of DHF: a rapid viral replication with high viremia (the severity of the disease being related to the level of viremia (Vaughn et al., 2000) and an important inflammatory response with release of high levels of inflammatory mediators (Rothman and Ennis, 1999).

There is no specific treatment against Dengue diseases. The management of DF is supportive with bed rest, control of fever and pain with antipyretics and analgesics, and adequate fluid intake. The treatment of DHF needs correction of fluid loss, replacement of coagulation factors, and infusion of heparin.

Preventive measures presently rely on vector control and personal protection measures, which are difficult to enforce and expensive. No vaccine against dengue is currently registered. Since the 4 serotypes of dengue are circulating worldwide and since they are reported to be involved in cases of DHF, vaccination should ideally confer protection against all 4 dengue virus serotypes.

Live attenuated vaccines (LAVs), which reproduce natural immunity, have been used for the development of vaccines against many diseases, including some viruses belonging to the same genus as dengue (examples of commercially available flavivirus live-attenuated vaccines include yellow fever and Japanese encephalitis vaccines). The advantages of live-attenuated virus vaccines are their capacity of replication and induction of both humoral and cellular immune responses. In addition, the immune response induced by a whole virion vaccine against the different components of the virus (structural and non-structural proteins) reproduced those induced by natural infection.

A dengue vaccine project was initiated in Thailand at the Centre for Vaccine Development, Institute of Sciences and Technology for Development Mahidol University. Candidate live-attenuated vaccines were successfully developed, at a laboratory scale, for dengue serotype 1 (strain 16007, passage 13), serotype 2 (strain 16681, passage 53=LAV2), and serotype 4 (strain 1036, passage 48) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3). These vaccines have been tested as monovalent (single serotype), bivalent (two serotypes), trivalent (three serotypes), and tetravalent (all four serotypes) vaccines in Thai volunteers. Those vaccines were found to be safe and immunogenic in children and in adults (Gubler, 1997). These LAV 1-4 strains have been described in EP 1159968 in the name of the Mahidol University and were deposited before the CNCM (CNCM I-2480; CNCM I-2481; CNCM I-2482 and CNCM I-2483 respectively).

The Den-2 strain 16681 was recovered from serum of a DHF (Dengue Hemorrhagic Fever) patient in Bangkok in 1964 (Halstead et al., 1970). The original viremic serum had been passaged 4 times on BSC-1 cells (African Green Monkey kidney cells) and 5 times on continuous LLC-$MK_2$ cells (Rhesus Monkey kidney cells). In 1977, the virus was passaged once in vivo, in susceptible monkeys (*Macaca Mulatta*), and then again in LLC-$MK_2$ cells. Two additional passages in mosquitoes (*Toxorhynchites amboinensis*) were conducted in 1980. Virus attenuation was performed by passages at 32° C. on PDK cells (Primary Dog Kidney cells). Attenuation of the strain was checked according to several in vitro and in vivo markers. Passage 50 fulfilled all these attenuation criteria and was chosen as master seed for vaccine production (1982), at passage 53. DEN-2 PDK53 vaccine candidate was evaluated in humans and found to be strongly immunogenic with no untoward clinical signs and symptoms (Bhamarapravati et al., 1989).

The complete sequence of the Dengue 2 Live-Attenuated Virus strain (LAV2) was established by R. Kinney et al. (CDC, Fort Collins) in 2001. Sequence differences between parent DEN-2 strain 16681 (SEQ ID No. 3) and LAV2 (SEQ ID No. 38) strain are described in Table 1. Thus, genetic comparison of the wild-type virus strain 16681 and LAV2 strain showed a set of 9 point mutations which could be linked to LAV2 attenuation.

TABLE 1

DEN-2 16681 and DEN-2 16681/PDK53 (LAV2) Sequence Differences

| coordinates | | LAV2 | | 16681 | |
|---|---|---|---|---|---|
| Gene-aa | position | Nt | Aa | nt | aa |
| **Non coding** | **Nt-57** | **T** | — | **C** | — |
| PrM-29 | Nt-524 | T | **Val** | A | **Asp** |
| E-373 | Nt-2055 | T | Phe | C | Phe |
| **NS1-53** | **Nt-2579** | **A** | **Asp** | **G** | **Gly** |
| NS2A-181 | Nt-4018 | T | **Phe** | C | **Leu** |
| **NS3-250** | **Nt-5270** | **A/T** | **Val/Glu** | **A** | **Glu** |
| NS3-342 | Nt-5547 | C | Arg | T | Arg |
| NS4A-75 | Nt-6599 | C | **Ala** | G | **Gly** |
| NS5-334 | Nt-8571 | T | Val | C | Val |

Nucleotide changes modifying the corresponding codon are indicated in bold.

The LAV2 strain which was initially established in 1983 was further rapidly identified as potential vaccine candidate (Bhamarapravati and Yoksan, 1997).

However, at that time, transmission to humans of Spongiform Encephalitis through mammalian cultures was not perceived as a risk and the virus was routinely maintained in Primary Dog Kidney cells (PDK). Furthermore, this LAV2 strain corresponds to a heterogeneous population. This heterogeneity represents an additional risk due to a potential in vitro or in vivo selection of one of the strain present in the composition.

In view of these increasing concerns, the Applicant decided to set up a sanitization process in order to get rid of any such risks. By transfecting Vero cells with the purified genomic RNA of LAV2, followed by three cycles of amplification in Vero cells, and two successive steps of virus plaque purification the Applicant produced a new Vero-Derived serotype 2 virus (VDV2).

This new VDV2 strain which has been thus derived by transfer to VERO cells and biological cloning differs from the LAV2 strain by sequence, an homogenous plaque size and temperature sensitivity but importantly has conserved some phenotypic and genotypic features of the LAV2 such as e.g. attenuation spots, small plaque phenotype, growth restriction at high temperature and has conserved the immunogenic features of the LAV2 strains. These features make this new strain a valuable vaccine candidate for prophylactic immunization in humans.

DEFINITIONS

"Dengue viruses" are positive-sense, single-stranded RNA viruses belonging to the Flavivirus genus of the flaviridae family. In the case of dengue serotype 2 (DEN-2) strain 16681, the entire sequence is 10723 nucleotides long (SEQ ID No. 3). The RNA genome contains a type I cap at the 5'-end but lacks a 3'-end poly (A)-tail. The gene organization is 5'-noncoding region (NCR), structural protein (capsid (C), premembrane/membrane (prM/M), envelope (E)) and non structural protein (NS1-NS2A-NS2B-NS3-NS4A-NS4B-NS5) and 3' NCR. The viral RNA genome is associated with the C proteins to form nucleocapsid (icosahedral symmetry). As with other flaviviruses, the DEN viral genome encodes the uninterrupted open reading frame (ORF) which is translated to a single polyprotein.

Serial passaging of a virulent (disease-causing) strain of dengue-2 results in the isolation of modified virus which are "live attenuated", i.e., infectious, yet not capable of causing disease. These modified viruses are usually tested in monkeys to evaluate their attenuation. However, Humans are the only primates that exhibit signs of clinical disease. The viruses that cause mild (i.e. acceptable in terms of regulatory purposes as presenting a positive benefit/risk ratio) to low or no secondary effects (i.e. systemic events and/or biological abnormalities and/or local reactions) in the majority of the tested humans but still infect and induce an immune response are called "live attenuated".

The term "LAV" denotes live attenuated Dengue viral strains. In the context of the invention "LAVs" are live attenuated strains initially derived from the Dengue serotype 2 (DEN-2) strain 16681 by passages in Primary Dog Kidney (PDK) Cells. For instance "LAV2/PDK53" is the attenuated strain established after 53 passages of strain 16681 in PDK cells (DEN-2 16681/PDK53). "LAV2/PDK50" is the attenuated strain established after 50 passages of strain 16681 in PDK cells (DEN-2 16681/PDK50). LAV2/PDK53 nucleotide sequence is shown in SEQ ID No. 38.

"VDV2" is meant a LAV obtainable by the sanitization process disclosed in the present application. A VDV2 is thus a biological clone (homogeneous) VERO-adapted Dengue serotype 2 virus capable of inducing a specific humoral immune response including neutralizing antibodies in primate especially in humans. The VDV2 strains of the invention can be easily reconstructed starting directly from the here disclosed VDV2 sequences. The induction of a specific humoral immune response can be easily determined by an ELISA assay. The presence of neutralising antibody in the serum of a vaccinee is evaluated by the plaque reduction neutralization test as described in section 4.1.1.2.2. A serum is considered to be positive for the presence of neutralizing antibodies when the neutralizing antibody titer thus determined is at least superior or equal to 1:10.

The terms "mutation" means any detectable change in genetic material, e.g. DNA, RNA, cDNA, or any process, mechanism, or result of such a change. Mutations include substitution of one or more nucleotides. In the context of the instant application, mutations identified in dengue-2 virus genomic sequence or polyprotein are designated pursuant to the nomenclature of Dunnen and Antonarakis (2000). As defined by Dunnen and Antonarakis at the nucleic acid level, substitutions are designated by ">", e.g. "31A>G" denotes that at nucleotide 31 of the reference sequence a A is changed to a G.

Variations at the protein level describe the consequence of the mutation and are reported as follows. Stop codons are designated by X (e.g. R97X denotes a change of Arg96 to a termination codon). Amino acid substitutions a designated for instant by "S9G", which means that Ser in position 9 is replaced by Gly.

VERO-Derived Dengue Serotype 2 Viruses (VDV2)

The composition of the previously developed dengue-2 vaccine candidate LAV2 was improved by a sanitization process.

The VERO-Derived Vaccine Dengue serotype 2 (VDV2) disclosed herein uses the DEN-2 16681 virus attenuated by serial passages on PDK cells. VDV2 contains the genomic sequence of the whole live-attenuated DEN-2 virus, and bears the same attenuation spots which have been linked to attenuation as the original LAV2 strain that was tested in humans.

Sanitization of the LAV2 vaccine was performed by removing proteins and introducing only purified viral genomic material into Vero cells. More specifically, sanitization of the strain was performed by purifying and transfecting viral RNA into Vero cells. The process comprises the following steps:

a) extracting and purifying viral RNA from plaque-purified LVA2 strain, e.g. DEN-2 16681/PDK50 viruses;

b) advantageously associating of the purified RNA with cationic lipids;

c) transfecting Vero cell, in particular Vero cell LS10;

d) recovering of the neo-synthesized virus; and e) purifying a VDV strain by plaque purification and optionally amplifying it in host cells, especially Vero cells.

The Vero cell technology is a well-known technology which has been used for different commercial products (injectable and oral polio vaccines, rabies vaccine). In the present invention qualified Vero cells were advantageously used to guarantee the absence of any risks potentially linked to the presence of adventitious agents. By "qualified VERO cells" is meant cells or cell lines for which culture conditions are known and is such that the said cells are free from any adventitious agents. These include e.g. the VERO cell LS10 of Sanofi Pasteur.

The thus isolated VDV strains are classically stored either in the form of a freezed composition or in the form of a lyophilised product. For that purpose, the VDV can be mixed with a diluent classically a buffered aqueous solution comprising cryoprotective compounds such a sugar alcohol and stabilizer. The pH before freezing or lyophilisation is advantageously settled in the range of 6 to 9, e.g. around 7 such as a pH of 7.5+/−0.2 as determined by a pH meter at RT. Before use, the lyophilised product is mixed with a pharmaceutically diluent or excipient such as a sterile NaCl 4% solution to reconstitute a liquid immunogenic composition or vaccine.

The Glu variant of LAV2 vaccine strain, at position NS3-250, was selected during transfection and cloning, and positions 5'NC-57 and NS1-53, also identified as critical for attenuation of LAV2 vaccine, were both conserved in VDV2 sequence.

Sequencing, at attenuation-specific loci, of virus recovered after transfection, did not reveal any mutation, compared to SEQ ID No. 38. The biologically cloned VDV2 virus exhibits a homogenous plaque phenotype and a remarkable genetic stability with regard to its LAV2 parent as it can be deduced especially from the conservation of the attenuation genotype.

VDV2 (passage 11) strain was sequenced and compared with the serotype 2 Dengue Live Attenuated Virus (LAV2) strain sequence (SEQ ID No. 38). A set of 10 nucleotide differences was identified, triggering six amino acid substitutions located in M and Env structural peptides, and also in non-structural peptides NS3 and NS5. None of these differences corresponds to any of the LAV2 attenuation positions.

TABLE 2

Sequence comparison between LAV2/PDK53 and VDV2 passage 11 strains.

| Nucleotides | | | Amino acids | | | |
|---|---|---|---|---|---|---|
| Position | LAV2 | VDV2 | Region | Position | LAV2 | VDV2 |
| 736 | G | C | M | 9 | G | R |
| 1619 | G | A | E | 228 | G | E |
| 1638 | A | G | E | 234 | K | K |
| 2520 | G | A | NS1 | 33 | K | K |
| **4723** | **T** | **A** | **NS3** | **69** | **S** | **T** |
| **5062** | **G** | **C** | **NS3** | **181** | **D** | **H** |
| **9191** | **G** | **A** | **NS5** | **541** | **R** | **K** |
| 9222 | A | G | NS5 | 551 | E | E |
| **10063** | **T** | **A** | **NS5** | **832** | **S** | **T** |
| 10507 | A | G | 3' nc | – | – | – |

Grey shading: differences in structural proteins;
Bold characters: differences in non-structural proteins.

The invention thus provides for live attenuated dengue-2 virus strains that have been obtained from the wild type virus DEN-2 16681 attenuated by serial passages on PDK cells and then by sanitization on VERO cells. In particular the attenuated strains of the invention comprise at least the identified sequence mutations (non-silent and optionally silent) relative to the nucleotide sequence or polyprotein sequence of the wild-type DEN-2 16681 and LAV2/PDK53 strains.

Accordingly, the invention relates to an isolated live attenuated dengue-2 virus strain which comprises, or consists of, the sequence of LAV2/PDK53 strain (SEQ ID No. 38) wherein at least nucleotides at positions 736, 1619, 4723, 5062, 9191, 10063, and 10507, and optionally 1638, 2520, 9222, and 10361, are mutated, with the proviso that the following nucleotides are not mutated: 57, 524, 2055, 2579, 4018, 5547, 6599, and 8571. Preferably, the mutations are substitutions. Preferably, the nucleotide at position 736 is C, the nucleotide at position 1619 is A, the nucleotide at position 4723 is A, the nucleotide at position 5062 is A, the nucleotide at position 9191 is A, the nucleotide at position 10063 A, and the nucleotide at position 10507 is G.

The nucleotide at position 5270 may be A or T, preferably A.

Still preferably, the isolated strain according to the invention comprises the sequence SEQ ID No. 38 wherein said sequence comprises at least the mutations 736 G>C, 1619 G>A, 4723 T>A, 5062 G>C, 9191 G>A, 10063 T>A, and 10507 A>G, and optionally the mutation 1638 A>G, 2520 G>A, and/or 9222 A>G.

Hence, a live attenuated dengue-2 virus strain according to the invention may comprise, or consist of, the sequence of wild-type dengue-2 strain 16681 (SEQ ID No. 3) wherein said sequence comprises at least the mutations 57 C>T, 524 A>T, 736 G>C, 1619 G>A, 2055 C>T, 2579 G>A, 4018 C>T, 4723 T>A, 5062 G>C, 5547 T>C, 6599 G>C, 8571 C>T, 9191 G>A, 10063 T>A, and 10507 A>G. Preferably, a live attenuated strain according to the invention further comprises the mutation 1638 A>G, 2520 G>A, and/or 9222 A>G by reference to the nucleotide sequence of wild-type strain 16681 (SEQ ID No. 3).

The live attenuated dengue-2 virus strains according to the invention may include variant strains that comprise a sequence SEQ ID No. 38 mutated at positions 736, 1619, 4723, 5062, 9191, 10063, and 10507, as defined above, and that further comprise a substitution of one or more nucleotides in a given codon position that results in no alteration in the amino acid encoded at that position.

Advantageously, the live attenuated dengue-2 virus strain according to the invention comprises a sequence which differs by a limited number of mutations, e.g. no more than 5, still preferably no more than 2, from SEQ ID No. 1.

Preferably, the genomic sequence of a dengue-2 virus strain according to the invention consists of the nucleotide sequence SEQ ID No. 1.

The invention also relates to live attenuated dengue-2 strains that may be derived from the VDV2 strain of sequence SEQ ID No. 1 by further passages on cells, in particular Vero cells.

The invention also relates to an isolated nucleic acid which comprises, or consists of, the DNA sequence SEQ ID No. 1 or its equivalent RNA sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

As used herein, by RNA sequence "equivalent" to SEQ ID No. 1 is meant a sequence SEQ ID No. 1 wherein deoxythymidines have been replaced by uridines. As SEQ ID No. 1 constitutes VDV2 cDNA sequence, the equivalent RNA sequence thus corresponds to the positive strand RNA of VDV2.

The invention further relates to the polyprotein of sequence SEQ ID No. 2 and to fragments thereof. SEQ ID No. 2 is the sequence of the polyprotein encoded by SEQ ID No. 1

A "fragment" of a reference protein is meant a polypeptide which sequence comprises a chain of consecutive amino acids of the reference protein. A fragment may be at least 8, at least 12, at least 20, amino acid long.

Said fragments of the polyprotein of sequence SEQ ID No. 2 comprise at least an arginine at position 9 of M protein (position 214 of SEQ ID No. 2), and/or a glutamic acid at position 228 of E protein (position 508 of SEQ ID No. 2), and/or a threonine at position 69 of NS3 protein (position 1543 of SEQ ID No. 2), and/or a histidine at position 181 of NS3 protein (position 1656 of SEQ ID No. 2), and/or a lysine at position 541 of NS5 protein (position 1725 of SEQ ID No. 2), and/or a threonine at position 832 of NS5 protein (position 3032 of SEQ ID No. 2).

According to an embodiment the fragment of the polyprotein encoded by SEQ ID No. 1 is or comprises M protein, and/or E protein, and/or NS3 protein and/or NS5 protein.

Immunogenic and Vaccine Compositions

The invention also relates to an immunogenic composition, suitable to be used as a vaccine, which comprises a VDV2 strain according to the invention.

The immunogenic compositions according to the invention elicit a specific humoral immune response toward the dengue virus comprising neutralizing antibodies.

Preferably, the immunogenic composition is a vaccine.

According to an embodiment, the immunogenic is a monovalent composition, i.e. it elicits en immune response and/or confers protection against Dengue-2 virus only.

According to another embodiment, the invention relates to a multivalent dengue immunogenic composition. Such a multivalent immunogenic composition or vaccine may be obtained by combining individual monovalent dengue vaccines. The immunogenic or vaccine composition may further comprise at least a live attenuated dengue virus of another serotype. In particular, the immunogenic or vaccine composition may comprise a VDV2 according to the invention in combination with at least a live attenuated dengue virus selected from the group consisting of serotype 1, serotype 3, and serotype 4.

Preferably, the immunogenic or vaccine composition may be a tetravalent dengue vaccine composition, i.e. a vaccine composition that comprises a VDV2 according to the invention in combination with a live attenuated dengue-1 virus strain, a live attenuated dengue-3 virus strain and a live attenuated dengue-4 virus strain.

Live attenuated dengue-1, dengue-3 and dengue-4 virus strains have been described previously. Reference may be made to the live-attenuated vaccines that were developed by Mahidol University by passaging dengue serotype 1 (strain 16007, passage 13; LAV1), and serotype 4 (strain 1036, passage 48, LAV4) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3) (LAV3). The nucleotide sequences of LAV1 (SEQ ID No. 40), LAV3 (SEQ ID No. 41), and LAV4 (SEQ ID No. 42) are shown in the annexed sequence listing.

Advantageously, a live attenuated dengue-1 strain may correspond to a VDV1 strain which has been obtained from the LAV1 strain developed by Mahidol by the process of sanitization according to the invention. In particular a live attenuated dengue-1 strain (VDV1) may comprise, and advantageously consists of the sequence SEQ ID No. 39.

Immunogenic compositions including vaccines may be prepared as injectables which can correspond to liquid solutions, suspensions or emulsions. The active immunogenic ingredients may be mixed with pharmaceutically acceptable excipients which are compatible therewith.

The immunogenic compositions or vaccines according to the present invention may be prepared using any conventional method known to those skilled in the art. Conventionally the antigens according to the invention are mixed with a pharmaceutically acceptable diluent or excipient, such as water or phosphate buffered saline solution, wetting agents, fillers, emulsifier stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Preferably, the immunogenic composition or vaccine corresponds to an injectable composition comprising an aqueous buffered solution to maintain e.g. a pH (as determined at RT with a pH meter) in the range of 6 to 9.

The composition according to the invention may further comprise an adjuvant, i.e. a substance which improves, or enhances, the immune response elicited by the VDV2 strain. Any pharmaceutically acceptable adjuvant or mixture of adjuvants conventionally used in the field of human vaccines may be used for this purpose.

The immunogenic compositions or vaccines according to the invention may be administered by any conventional route usually used in the field of human vaccines, such as the parenteral (e.g. intradermal, subcutaneous, intramuscular) route In the context of the present invention immunogenic compositions or vaccines are preferably injectable compositions administered subcutaneously in the deltoid region.

Method for Immunizing

The invention further provides for a method of immunizing a host in need thereof against a dengue infection which comprises administering the host with an immunoeffective amount of a vaccine composition according to the invention.

A "host in need thereof" denotes a person at risk for dengue infection, i.e. individuals travelling to regions where dengue virus infection is present, and also inhabitants of those regions.

The route of administration is any conventional route used in the vaccine field the choice of administration route depends on the formulation that is selected preferably, the immunogenic composition or vaccine corresponds to an injectable composition administered via subcutaneous route, advantageously in the deltoid region.

The amount of LAV or VDV, in particular VDV2, in the immunogenic compositions or vaccines may be conveniently expressed in viral plaque forming unit (PFU) unit or Cell Culture Infectious Dose 50% ($CCID_{50}$) dosage form and prepared by using conventional pharmaceutical techniques. For instance, the composition according to the invention may be prepared in dosage form containing 10 to $10^6$ $CCID_{50}$, or $10^3$ to $10^5$ $CCID_{50}$ of LAV or VDV, for instance a dose of 4±0.5 $\log_{10}$ $CCID_{50}$ of VDV2 strain for a monovalent composition. Where the composition is multivalent, to reduce the possibility of viral interference and thus to achieve a balanced immune response (i.e. an immune response against all the serotype contained in the composition), the amounts of each of the different dengue serotypes present in the administered vaccines may not be equal.

An "immunoeffective amount" is an amount which is capable of inducing a specific humoral immune response comprising neutralising antibodies in the serum of a vaccinee, as evaluated by the plaque reduction neutralization test as described in section 4.1.1.2.2; a serum being considered to be positive for the presence of neutralizing antibodies when the neutralizing antibody titer thus determined is at least superior or equal to 1:10.

The volume of administration may vary depending on the route of administration. Subcutaneous injections may range in volume from about 0.1 ml to 1.0 ml, preferably 0.5 ml.

The optimal time for administration of the composition is about one to three months before the initial exposure to the dengue virus. The vaccines of the invention can be administered as prophylactic agents in adults or children at risk of Dengue infection. The targeted population thus encompasses persons which are naïve as well as well as non-naïve with regards to dengue virus. The vaccines of the invention can be administered in a single dose or, optionally, administration can involve the use of a priming dose followed by a booster dose that is administered, e.g. 2-6 months later, as determined to be appropriate by those of skill in the art.

The invention will be further described in view of the following figures and examples.

FIGURES

Figure 3:
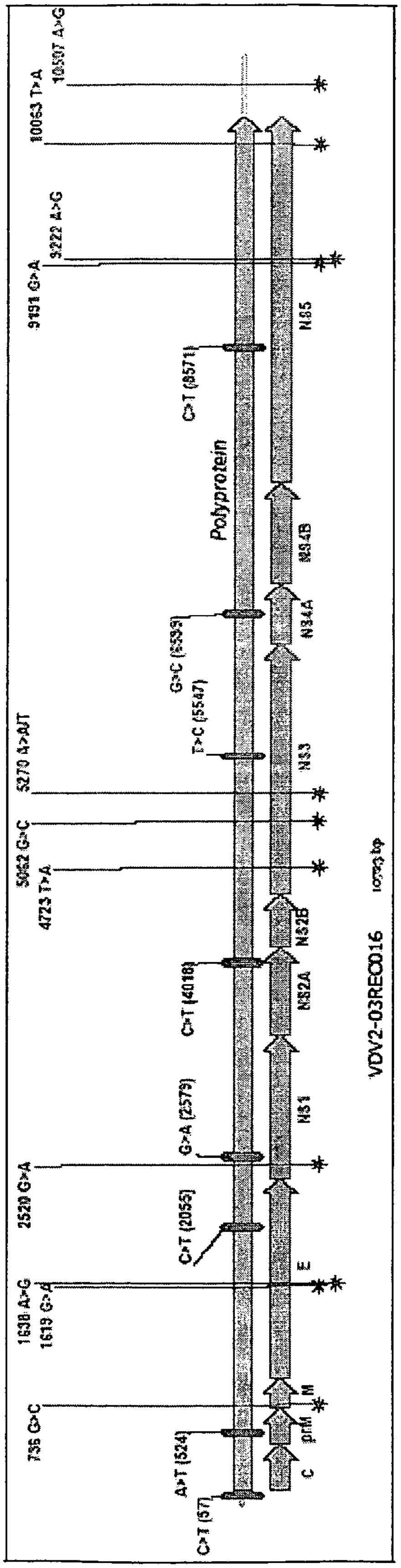

FIG. 3 is a diagrammatic representation of VDV2 genome map. The above arrow is the polyprotein coding sequence. The below arrows represent mature peptides coding sequence. The vertical bars symbolize the nucleotidic variations between wild-type dengue 2 strain 16681 and LAV2 strain. The stars designate the nucleotidic variations between LAV2 and VDV2.

Figure 4:
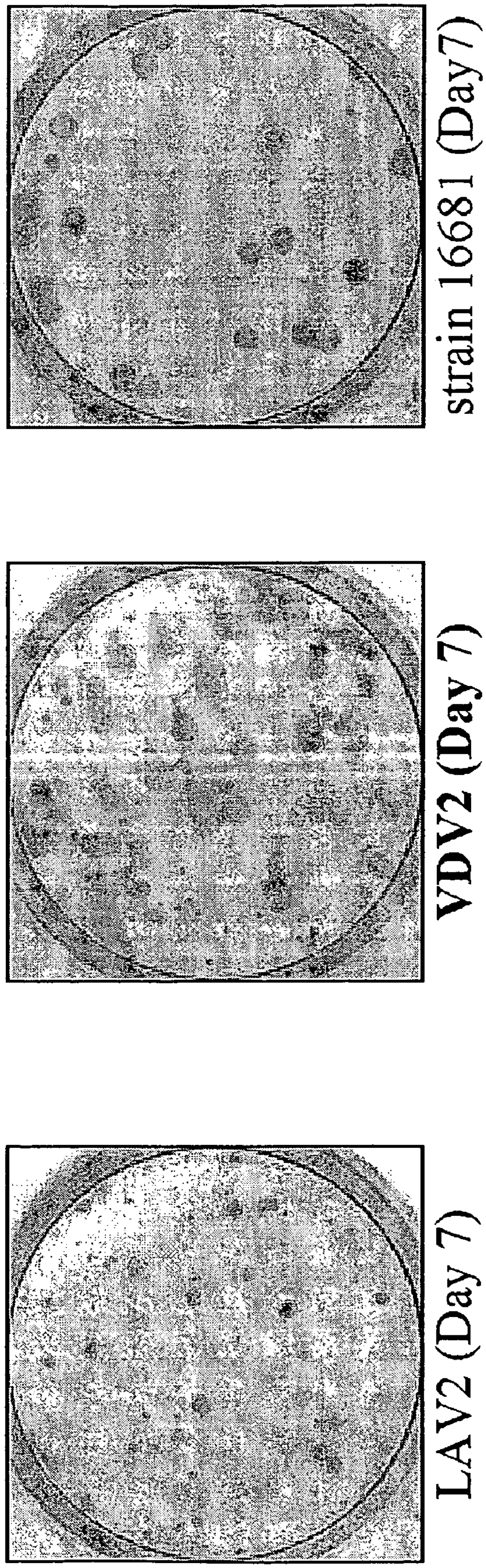

FIG. 4 shows plaque size analysis after 7 days of incubation at 37° C. for dengue-1 viruses LAV2, VDV2, and strain 16681.

Figure 5:
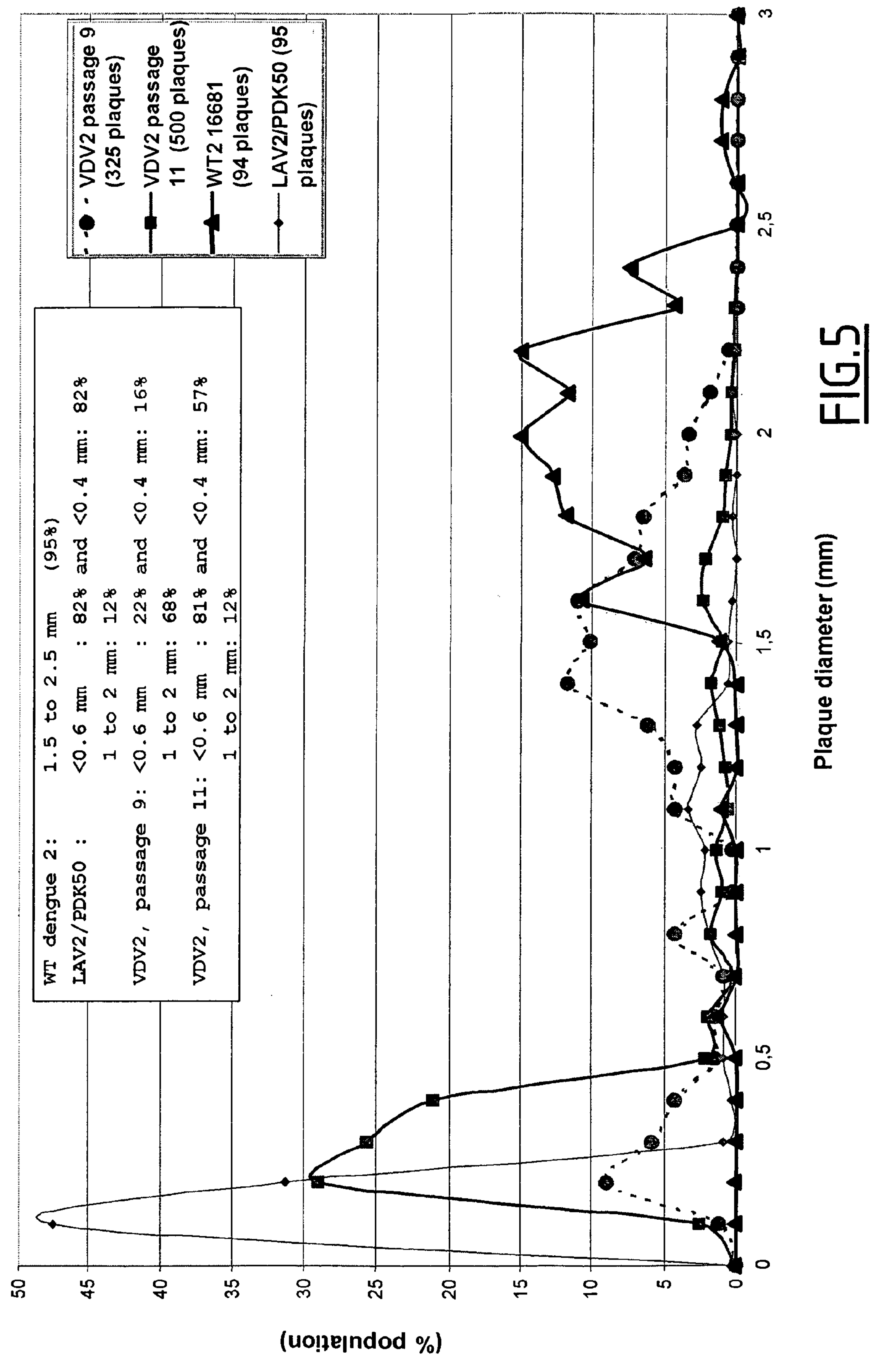

FIG. 5 is a graphic analysis showing plaque size distribution for dengue-2 viruses LAV2, VDV2, and strain 16681.

Figure 6:
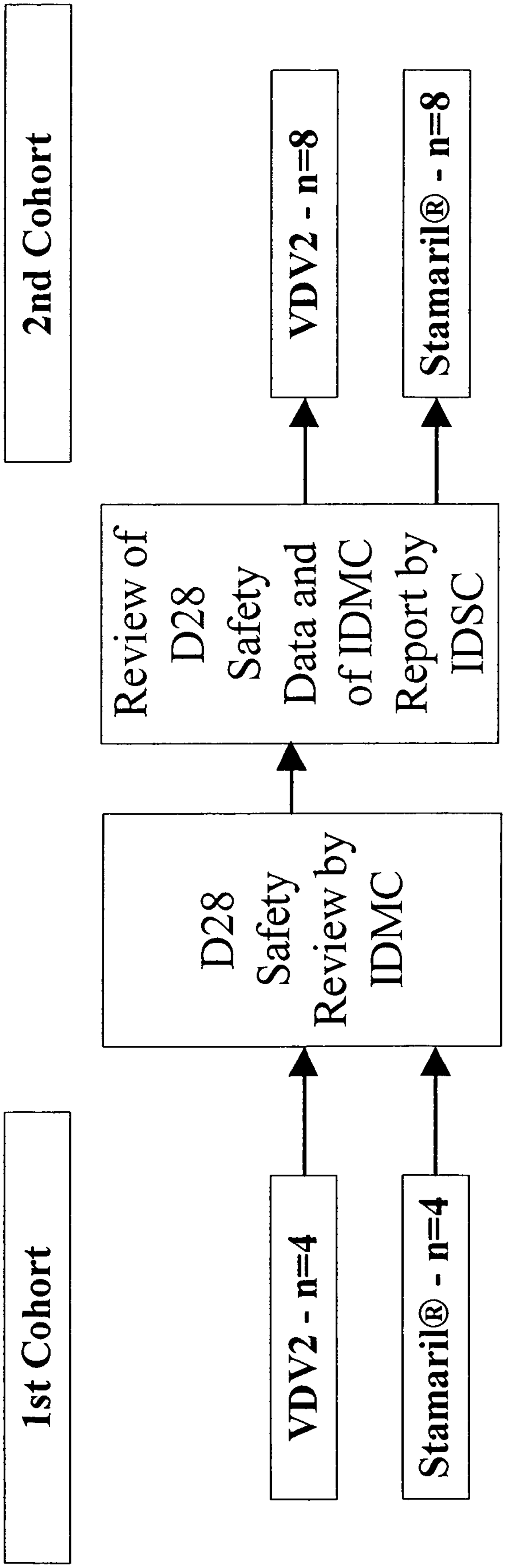

FIG. 6 is a summary of Trial Design for assessment of safety of VDV2 monovalent in healthy flavivirus-naïve adults.

EXAMPLES

Example 1

Sanitization 1.1 Viral RNA Purification

The RNA purification and transfection process was performed as follows. DEN-2/PDK50 suspension was resuspended in 0.5 ml of water and diluted in order to contain at least $3\times10^4$ and up to $3\times10^7$ $TCID_{50}$ or PFU of virus per milliliter. One unit of benzonase diluted in 0.01 ml of William's medium was added to 0.5 ml of virus, in order to digest DNA or RNA molecules from cellular origin, and the solution was incubated for 2 hours at 4° C. on an agitator. At the end of incubation step, 0.65 ml of a denaturing buffer containing guanidium chloride, detergent (SDS), and βmercaptoethanol (RTL-βmercaptoethanol buffer, provided in the kit RNeasy Mini kit, Qiagen Ref. 74104) were added and proteins were extracted once with phenol/chloroform (1/1) vol/vol and once with chloroform vol/vol, followed by centrifugation for 5 min at 14,000 rpm at room temperature. After each extraction, the aqueous phase was collected, taking care not to collect material (white precipitate) at the interface, and transferred to a clean 1 ml-Eppendorf tube. The RNA solution was then applied onto a QIAgen column following the recommendations of the manufacturer (RNeasy minikit, QIAgen), in order to remove traces of solvent, and eluted with 0.06 ml of nuclease-free H2O water. The presence of viral RNA was confirmed by quantitative RT-PCR, using a reference curve established with known quantities of virus, in $TCID_{50}$/ml.

1.2 Transfection of Vero Cells with Purified RNA

Transfection was performed using lipofectamine (LF2000 Reagent, Life Technologies), a mixture of cationic lipids that associate to RNA through charge interactions and allows transfer of the complexes into the cytoplasm of the cells by fusion with the cell membrane. The optimal quantity of LF2000 reagent was determined in a preliminary experiment by incubating Vero cells, plated 16 to 24 hours before (0.3-$0.5\times10^6$ cells per well in a 6 wells plate) with increasing doses (5 to 20 µl) of lipofectamine. Cells were then incubating 4 to 5 hours at 32° C., 5% $CO_2$, before replacing the medium by fresh culture medium without FCS, and the incubation was continued overnight at 32° C. Toxicity (round, refringent or floating cells, homogeneity of the cell monolayer) was checked regularly for 48 hours, under an inverted microscope. The highest dose of lipofectamine that was not toxic under these conditions was 10 µl and was chosen for RNA transfection.

Four transfections were carried out in parallel, using ¼ of the RNA preparation (about $2\times10^4$ log $eqTCID_{50}$, according to qRT-PCR). Twenty-five microliters of viral RNA solution were diluted in 500 µl of OptiMEM medium (GIBCO) containing 15 µl of LF2000 Reagent (a mixture of cationic lipids that associate to RNA through charge interactions, and allow transfer of the complexes into the cytoplasm of the cells by fusion with the cell membrane). 200 ng of yeast tRNA were added as carrier in 2 out of the 4 reactions.

The 4 transfection mixes were allowed to precipitate for 10 min at room temperature before addition to 6-wells plates of confluent Vero cells, and incubation at 36° C. After four hours, transfection mix was removed and cells were rinsed once in PBS. Three milliliters of post-transfection medium (Williams, GIBCO) were added, and incubation was continued for 5 days at 32° C. Culture medium was then replaced by 3 ml of Dengue infection medium (Williams supplemented with 10 mM $MgSO_4$).

A focus of cells presenting typical cytopathic effects (round, refringent cells) was detected at day 8 post-transfection in 1 out of the 2 wells transfected in presence of tRNA. Release of virus in the supernatant of these cells was confirmed by qRT-PCR. Eleven days post-transfection, marked cytopathic effects were detected in this only well, while the supernatant of the three other transfected-wells remained negative.

The viral solution recovered after transfection was re-named TV100 (instead of 16681 PDK50/Vero-2) and exhibited an infectious titer of 5.8 log $TCID_{50}$/ml after dilution at ½ in an aqueous buffered solution comprising cryoprotective agents (pH=7.5).

1.3 Characterization of Viruses Recovered after Transfection

Spot sequencing of specific loci important for attenuation was performed by R. Kinney (CDC, Fort Collins). Data are presented in Table 3.

TABLE 3

Sequencing of transfected virus at attenuation-specific positions

| Virus | 5'-NC-57 Nt 57 | NS1-53 Nt 2579 (aa) | NS3-250 Nt 5270 (aa) |
|---|---|---|---|
| DEN-2 16681 | C | G (Gly) | A (Glu) |
| DEN-2 PDK53 | T | A (Asp) | T/A (Val/Glu) |
| TV100 | T | A (Asp) | A (Glu) |

VDV2 has retained the important attenuating loci at 5'NC-57 and NS1-53, and the wild-type 16681 locus of the NS3-250-Glu variant in the PDK53 vaccine. The NS3-250-Glu/Val mix in the PDK53 vaccine was observed to be stable between passages PDK45 and PDK53 suggesting that selection has occurred in Vero cells. Previous analysis of DEN-2 vaccine isolated from serum of a vaccinee had demonstrated that this selection could also occur in humans.

Viral plaques diameters were measured in Vero cells. Briefly, Vero cells were plated at a density of 1.000.000 cells/$cm^2$ in culture medium containing 4% of FBS. After overnight incubation, the medium was removed and cells were infected with serial twofold or fivefold dilutions of virus. After 1.5 hour at 37° C. 5% $CO_2$, the inoculum was removed and cells were incubated at 37° C. 5% $CO_2$ in Minimal Eagle Medium (MEM) containing 1.26% methylcellulose and 10% FBS. After 11 days of incubation, plates were fixed 20 minutes in cold acetone at −20° C. and revealed by immunocoloration with a flavivirus-specific mAb, diluted at 2.5 µg/ml. Viral plaques were measured using an image analysis software (Saisam/Microvision).

VDV2 was compared to LAV2 16681/PDK50 seed (Table 4) and exhibited similar homogeneous small plaques of 1-3 mm diameter.

TABLE 4

Plaques size of LAV2 16681/PDK50 and VDV2

| Step | Virus | LP/MP | SP |
|---|---|---|---|
| Before transfection | LAV2 PDK50 | 0 | 319 |
| After transfection | Uncloned VDV2 | 0 | 183 |

LP/MP: Number of Large/Medium Plaques in 6 wells
SP: Number of Small Plaques in 6 wells 1.4 Plaque-Purifications Three additional amplification passages (P2 to P4) were performed on the virus recovered after transfection. Biological cloning by plaque-purification was performed on P3 and P4 passaged virus (named LST 003 and LST 007, respectively).

Briefly, Vero cells were plated in 6-well plates and infected with serial dilutions of virus, in order to get between 1 and 20 plaques by plate. After 1.5 hour at 37° C. 5% $CO_2$, the inoculum was removed and cells were incubated under 3 ml of solid medium composed of MEM-10% FCS pre-heated at 42° C. and mixed extemporaneally with 2% of melted agarose equilibrated at 42° C. The medium was allowed to solidify at room temperature for 30 min; under flow hood, and plates were incubated in inverted position for 10 days at 32° C.-5% $CO_2$. A second layer of the same medium supplemented with 0.01% of neutral red was then added and plates were incubated for an additional night at 32° C. Six well-isolated small plaques were picked under sterile conditions using a micropipet equipped with an 0.1 ml tip, and transferred into sterile tubes containing 0.2 ml of MEM-4% FCS: three from P3 passage (identified as clones 31, 32 and 33), and three from P4 passage (identified as clones 71, 72 and 73). The suspension was homogenised by vortexing, serially diluted in the same medium, and immediately used to infect 6-well plates of Vero cells. The protocol was repeated and a second picking of two SP was done on clones 32, 33, 71 and 72, and one SP on clone 31. Each picked plaque was diluted in 1 ml of medium, before amplification on Vero cells, in T25 $cm^2$ flasks. Culture medium was collected at day 6 post-infection, diluted with the same volume of an aqueous buffered solution comprising cryoprotective agent (pH 7.5) and frozen at −70° C. All these steps were performed at 32° C.

Plaque purified virus were named 311, 321, 322, 331, 332, 341, 342, 351, 352, 711, 712, 721 and 722, respectively.

Infectious titers were determined on Vero cells at the end of the first amplification (see below)

| | |
|---|---|
| Clone 311: 3.95 $LogCCID_{50}$/ml | |
| Clone 321: 5.20 $LogCCID_{50}$/ml | Clone 322: 5.45 $LogCCID_{50}$/ml |
| Clone 331: 5.55 $LogCCID_{50}$/ml | Clone 332: 4.95 $LogCCID_{50}$/ml |
| Clone 341: 2.80 $LogCCID_{50}$/ml | Clone 342: 4.85 $LogCCID_{50}$/ml |
| Clone 351: 5.35 $LogCCID_{50}$/ml | Clone 352: 5.50 $LogCCID_{50}$/ml |
| Clone 711: 5.45 $LogCCID_{50}$/ml | Clone 712: 5.65 $LogCCID_{50}$/ml |
| Clone 721: 5.30 $LogCCID_{50}$/ml | Clone 722: 5.60 $LogCCID_{50}$/ml |

A second amplification on Vero cells was carried out for three clones: clones 331, 352, and 722. Culture supernatants were collected at day 8 post-infection, diluted at ½ with an aqueous buffered solution comprising cryoprotective agent (pH 7.5) and named TV331, TV352 and TV722.

1.5 Characterization of Cloned Virus

After the $1^{st}$ amplification, all amplified viruses exhibited same plaque size phenotype and titers equivalent to, or higher than 5 log $CCID_{50}$/ml (except clones 311 and 341 which were significantly lower). Sequencing at attenuation-specific positions was performed on 6 clones from the $1^{st}$ amplification (clones 321, 331, 351, 352, 711, 721) and the three clones from the $2^{and}$ amplification, and revealed no mutation.

In absence of any significant difference between the clones, TV722 was selected and amplified in VERO cells in order to generate a VDV2 vaccine candidate strain.

In conclusion, a total number of 11 passages was necessary to obtain a biological clone of DEN-2 166681/PDK50 adapted on VERO cells.

Further characterizations have been performed then by determining VDV2 passage 11 complete sequence and phenotypic testing.

Example 2

Sequencing

The complete sequence of the virus was generated according to the following strategy. Viral genomic RNA was purified. The full genome was amplified by 16 overlapping RT-PCR reactions. Each PCR was designed so that sequencing tags were added on each DNA strand. This allowed simpler sequence reactions, all driven by a single pair of universal sequencing primers. Each PCR product was individually sequenced on both DNA strands. All results were reassembled to reconstruct the full VDV2 genome.

2.1 Materials 2.1.1 Viruses

The viruses to which it is referred here are DEN-2 16681; LAV-2/PDK53; VDV2, the sequences of which are given in the attached sequence listing.

The complete genome sequence of these viruses is 10723 nucleotides in length.

2.1.2 Primers

All primers have been designed in Seqweb bioinformatics package (Accelrys), primer design module (Table 6).

TABLE 5

Sequencing at attenuation-specific spots of DEN-2 viruses

| | | 5'-UTR | prM | E | NS1 | NS2a | N53 | | NS4A | N55 |
|---|---|---|---|---|---|---|---|---|---|---|
| Step/cell | Virus | 57 | 524 | 2055 | 2579 | 4018 | 5270 | 5547 | 6599 | 8571 |
| Wild-type/PGMK | 16681 | C | A | C | G | C | A | T | G | C |
| Vaccine/PDK | PDK53 | T | T | T | A | T | A/T | C | C | T |
| | TV 321 | T | T | T | A | T | A | C | C | T |
| | TV 331 | T | T | T | A | T | A | C | C | T |
| 2nd plaque- | TV 342 | T | T | T | A | T | A | C | C | I |
| purification/VERO | TV 352 | T | T | T | A | T | A | C | C | T |
| | TV 711 | T | T | T | A | T | A | C | C | T |
| | TV 722 | T | T | T | A | T | A | C | C | T |
| $2^{nd}$ amplification/VERO | TV 722PM | T | T | T | A | T | A | C | C | T |

Nucleotides position are indicated below each gene and referred to published sequence of DEN-2 16681 strain.

TABLE 6 list of RT-PCT and sequencing primers

| Name | Primers sequences | | NtStart | NtEnd | Primer length | RT-PCR length | Overlap |
|---|---|---|---|---|---|---|---|
| D2 01 + | GTTTTCCCAGTCACGACacgtggaccgacaaagacag | (SEQ ID No.4) | 13 | 32 | 37 | 978 | -31 |
| D2 01 − | AACAGCTATGACCATGttcctcctgaaacccccttcc | (SEQ ID No.5) | 991 | 972 | 36 | | 371 |
| D2 02 + | GTTTTCCCAGTCACGACatcacgtacaagtgtcccc | (SEQ ID No.6) | 583 | 601 | 36 | 949 | |
| D2 02 − | AACAGCTATGACCATGagcaacaccatctcattgaag | (SEQ ID No.7) | 1532 | 1512 | 37 | | 163 |
| D2 03 + | GTTTTCCCAGTCACGACtgcaaccagaaaacttggaatacac | (SEQ ID No.8) | 1325 | 1349 | 42 | 948 | |
| D2 03 − | AACAGCTATGACCATGgctccatagattgctccaaagac | (SEQ ID No.9) | 2273 | 2251 | 39 | | 203 |
| D2 04 + | GTTTTCCCAGTCACGACcccagtcaacatagaagcagaacc | (SEQ ID No.10) | 2025 | 2048 | 41 | 878 | |
| D2 04 − | AACAGCTATGACCATGccaaagccatagtcttcaacttcc | (SEQ ID No.11) | 2903 | 2880 | 40 | | 155 |
| D2 05 + | GTTTTCCCAGTCACGACatcatgcaggcaggaaaac | (SEQ ID No.12) | 2707 | 2725 | 36 | 949 | |
| D2 05 − | AACAGCTATGACCATGaccataaccatcactcttccc | (SEQ ID No.13) | 3656 | 3636 | 37 | | 240 |
| D2 06 + | AACAGCTATGACCATGaccataaccatcactcttccc | (SEQ ID No.14) | 3368 | 3386 | 36 | 930 | |
| D2 06 − | AACAGCTATGACCATGgctctctccagttccaaatc | (SEQ ID No.15) | 4298 | 4279 | 36 | | 146 |
| D2 07 + | GTTTTCCCAGTCACGACaagaaccagcaagaaaaggag | (SEQ ID No.16) | 4113 | 4133 | 38 | 868 | |
| D2 07 − | AACAGCTATGACCATGcaccattaccataaagacccac | (SEQ ID No.17) | 4981 | 4960 | 38 | | 226 |
| D2 08 + | GTTTTCCCAGTCACGACttgaaccatcatgggcggac | (SEQ ID No.18) | 4715 | 4734 | 37 | 910 | |
| D2 08 − | AACAGCTATGACCATGtcctgcttttatacttggaacgaac | (SEQ ID No.19) | 5625 | 5601 | 41 | | 208 |
| D2 09 + | GTTTTCCCAGTCACGACaaagcccatttcacagaccc | (SEQ ID No.20) | 5375 | 5393 | 36 | 920 | |
| D2 09 − | AACAGCTATGACCATGtcaatttcttcctttccccttc | (SEQ ID No.21) | 6295 | 6274 | 38 | | 158 |
| D2 10 + | GTTTTCCCAGTCACGACgagaggagaagcaaggaaaac | (SEQ ID No.22) | 6096 | 6116 | 38 | 923 | |
| D2 10 − | AACAGCTATGACCATGagggacacattcactgagg | (SEQ ID No.23) | 7019 | 7001 | 35 | | 233 |
| D2 11 + | GTTTTCCCAGTCACGACacagagaacaccccaagac | (SEQ ID No.24) | 6750 | 6768 | 36 | 929 | |
| D2 11 − | AACAGCTATGACCATGtccacttcctggattccac | (SEQ ID No.25) | 7679 | 7661 | 35 | | 308 |
| D2 12 + | GTTTTCCCAGTCACGACacaagtaatgctcctagtcctc | (SEQ ID No.26) | 7332 | 7353 | 39 | 935 | |
| D2 12 − | AACAGCTATGACCATGttcactgatgacactatgttcc | (SEQ ID No.27) | 8267 | 8246 | 38 | | 211 |
| D2 13 + | GTTTTCCCAGTCACGACgtcatcaccaaatcccacag | (SEQ ID No.28) | 8016 | 8035 | 37 | 937 | |
| D2 13 − | AACAGCTATGACCATGgcttcttctctctttttcccatc | (SEQ ID No.29) | 8953 | 8931 | 39 | | 140 |
| D2 14 + | GTTTTCCCAGTCACGACaaggtgagaagcaatgcag | (SEQ ID No.30) | 8773 | 8791 | 36 | 937 | |
| D2 14 − | AACAGCTATGACCATGtggaaatggtgtgaacagaag | (SEQ ID No.31) | 9710 | 9690 | 37 | | 209 |
| D2 15 + | GTTTTCCCAGTCACGACgcattcagcacctaacaatcac | (SEQ ID No.32) | 9641 | 9482 | 39 | 9335 | |
| D2 15 − | AACAGCTATGACCATGggcatttatgatggcctgac | (SEQ ID No.33) | 10396 | 10377 | 36 | | — |
| D2 16i+ | ccatggaagctgtacgc | (SEQ ID No.34) | 10480 | 10496 | 64 | 234 | |
| D2 16i − | AACAGCTATGACCATGtgattcaacagcaccattcc | (SEQ ID No.35) | 10714 | 10695 | 36 | | -28 |

2.2 Methods 2.2.1 Viral RNA Purification

From previous experience, a minimal of 1000 $DICC_{50}$ is required to get a positive RT-PCR reaction in the next steps. This means that a minimum virus titer of $10^4$ $DICC_{50}$/mL is necessary. Virus genomic RNA was purified using QIAamp viral RNA mini kit (Qiagen), according to the manufacturer's recommendations. Briefly, a volume of 140 µl from a crude viral sample was incubated in the presence of the lysis solution, and loaded onto a kit column. After washing steps, the purified viral RNA was eluted by 60 µl of sterile nuclease-free water containing 1 µl (40 units) of RNAse inhibitor (RNAse Out, Sigma).

2.2.2 Reverse Transcription

Viral RNA was reverse transcribed into cDNA by a reverse transcriptase (reverse iT) from ABGene. Again, standard operating conditions were applied, using 10 µl of purified RNA, in a final reaction volume of 20 µl. The reaction was initiated by hybridization of the minus strand primers. One RT reaction per PCR was performed. The cDNA synthesis was obtained by 45 min incubation at 47° C.

2.2.3 PCR

All PCR were performed with Expand High Fidelity PCR system (Roche diagnostics), using all 16 pairs of primers (+) and (−) from Table 6. PCR conditions were the following ones:

| | | | | | | |
|---|---|---|---|---|---|---|
| RT | 2 | µl | PCR program | | | |
| 10x buffer | 2.5 | µl | Denaturation | 94° C. | 2 min | |
| dNTP mix (10 mM) | 2 | µl | Denaturation | 94° C. | 15 sec | |
| Primers | 0.8 | µl each | Hybridization | 55° C. | 30 sec | 40 cycles |
| H2O | 16.4 | µl | Elongation | 68° C. | 1 min | |
| Enzyme | 0.5 | µl | Elongation | 68° C. | 5 min | |

All PCR products were controlled by electrophoresis on agarose gel.

2.2.4 Sequencing

The major part of the sequence reactions has been outsourced to Genome Express. Genome extremities, ambiguities, some inter-PCR junctions, and regions not sequenced by Genome Express for technical reasons were performed in-house.

Sequencing at Genome Express: PCR products were shipped at +4° C., and sequencing results were received as informatic sequence files. Text file, quality files and chromatograms are available for each individual sequence. After sequence alignment, all discrepancies were checked on the chromatogram, and corrected if identified as sequence algorithm errors.

In-house sequencing: Sequence reactions were performed on thermocycler PTC-200 (MJ Research), with Sequitherm Excell II LC kit (Epicentre). Each PCR product was sequenced on both strands independently in a single reaction. Reactions were loaded onto a sequence electrophoresis gel. Run and analysis of sequence were performed on the automated sequencer Gene ReadIR 4200 (Li-Cor).

Sequence reaction

| | | | | | | |
|---|---|---|---|---|---|---|
| DNA | up to 200/250 | ng | PCR program | | | |
| Reaction buffer | 7.2 | µl | Denaturation | 92° C. | 2 min | |
| Primers (1-2 pM) | 1.5 | µl each | Denaturation | 92° C. | 15 sec | |
| Enzyme | 1 | µl | Hybridization | 50° C. | 30 sec | 30 cycles |
| $H_2O$ | up to 20 | µl | Elongation | 70° C. | 1 min | |
| | | | Elongation | 70° C. | 10 sec | |

Addition of 3 µl of denaturating/loading buffer.

Denaturation of samples 3 min at 95° C. and ice cooling just before samples loading.

Sequence electrophoresis

| Electrophoresis parameters | | Gel parameters | |
|---|---|---|---|
| Voltage | 1500 V | Gel hight | 41 cm |
| Current | 35 mA | Gel thickness | 0.2 mm |
| Power | 40 W | Temperature | 45° C. |
| Run time | 9H00 | Scan speed | 3 |

2.3 Results

All PCR fragments were sequenced from both ends using a common PCR added tail, i.e. a specific motif which has been added at 5' end of all primers:

```
5' primers: M13SEQ-GTTTTCCCAGTCACGAC (SEQ ID No.36)

3' primers: M13REV-AACAGCTATGACCATG  (SEQ ID No.37)
```

M13-SEQ and -REV sequences correspond to universal M13 primers motifs (New England Biolabs references).

For final contig assembly, a quick analysis was performed in Vector NTi, in ContigExpress module (Informax). The LAV2 reference sequence was compared with all individual sequencing results. In such conditions, all results could be aligned at the right place on the complete genome, even when some regions were still missing contig assembly, giving a quick visualization of the overall genome alignment.

2.3.1 Complete VDV2 Sequence Assembly

The final sequence alignment was performed in Vector NTi, AlignX module (Informax). The classical multiple sequence alignment algorithm ClustalW (Thompson et al., 1994) was used by the software to build the global alignment. All the sequence results were aligned together with the LAV2 reference sequence, thus allowing for a better reconstruction of the genome. Any discrepancy in the sequence with regard to the reference required a confirmation on another independent sequence reaction. The complete sequence of VDV2 is shown in SEQ ID No. 1.

Some ambiguities are often found in single sequences, especially near sequence extremities. This is inherent to the somewhat poor quality of the reaction at both ends of any PCR fragment. Such poor quality sequences were excluded from the alignment, until two other independent sequence reactions were available from other PCR products. Discrepancy towards the reference was not taken into account in the final alignment when not confirmed in at least two independent other PCR sequences matching the consensus. Conversely, any discrepancy confirmed on two independent sequences was kept in the final sequence.

Table 7 summarizes the characteristics of each individual sequence reaction, indicating start, end and length. Overlaps between adjacent PCR are also indicated, as well as differences with regard to the reference sequence in the last column.

TABLE 7

Dengue VDV2 individual sequences characteristics

| Name | Start | End | Size | Overlap | Comments |
|---|---|---|---|---|---|
| D2 01+ | 33 | 365 | 332 | 0 | 2 sequences |
| D2 01− | 619 | 79 | 540 | 5 | 2 sequences |
| D2 02+ | 614 | 1334 | 720 | | 736 G > C (M9-G > R) |
| D2 02− | 1488 | 654 | 834 | 127 | 736 G > C (M9-G > R) |
| D2 03+ | 1361 | 2135 | 774 | | 1619 G > A (E228 G > E); 1638 A > G (E234K s) |
| D2 03− | 2227 | 1416 | 811 | 179 | 1619 G > A (E228 G > E); 1638 A > G (E234K s) |
| D2 04+ | 2048 | 2774 | 726 | | 2520 G > A (NS1-33K s) |
| D2 04− | 2866 | 2210 | 656 | 133 | 2520 G > A (NS1-33K s) |
| D2 05+ | 2733 | 3495 | 762 | | |
| D2 05− | 3619 | 2819 | 800 | 251 | |
| D2 06+ | 3393 | 4196 | 803 | | |
| D2 06− | 4257 | 3368 | 889 | 78 | |
| D2 07+ | 4179 | 4830 | 651 | | 4723 T > A (NS3-69 S > T) |
| D2 07− | 4851 | 4223 | 628 | 130 | 4723 T > A (NS3-69 S > T) |
| D2 08+ | 4742 | 5506 | 764 | | 5062 G > C (NS3-181 DD > H) |
| D2 08− | 5582 | 4721 | 861 | 188 | 5062 G > C (NS3-181 DD > H) |
| D2 09+ | 5394 | 6100 | 706 | | |
| D2 09− | 6669 | 5979 | 690 | 545 | |
| D2 10+ | 6124 | 6996 | 872 | | |
| D2 10− | 6983 | 6148 | 835 | 218 | |
| D2 11+ | 6778 | 7567 | 789 | | |
| D2 11− | 7649 | 6781 | 868 | 317 | |
| D2 12+ | 7365 | 8236 | 971 | | |
| D2 12− | 8241 | 7332 | 909 | 191 | |
| D2 13+ | 8050 | 8797 | 747 | | |
| D2 13− | 8819 | 8147 | 672 | 22 | |
| D2 14+ | 8707 | 9700 | 903 | | 9191 G > A (NS5-541 R > K); 9222 A > G (NS5-551E s) |
| D2 14− | 9654 | 8804 | 850 | 199 | 9191 G > A (NS5-541 R > K); 9222 A > G (NS5-551E s) |
| D2 15+ | 9501 | 10285 | 784 | | 10063 T > A (NS5-832 S > T) |
| D2 15− | 10347 | 9702 | 645 | 187 | 10063 T > A (NS5-832 S > T) |
| D2 16i+ | 10486 | 10687 | 201 | | 10507 A > G |
| D2 16i− | 10694 | 10160 | 534 | 0 | 10507 A > G |

The two extremities of the genome could not be sequenced from PCR amplification, because cDNA synthesis and PCR DNA reaction required oligonucleotides complementary to the ends of the genome. During the amplification step, these oligonucleotides are incorporated into the PCR fragment. The sequence result is that of the synthetic oligonucleotide, and not that of the virus itself. PCR from both ends of the virus genome did work properly, suggesting that the viral sequence was not significantly different from the oligonucleotide sequence (if it had been the case, PCR amplification should have failed or at least should have been of poor quality). We were not able to distinguish them from all other PCR amplifications. So, in the reconstructed genome, both genome ends were considered as identical to oligonucleotide sequences (and also identical to the reference). At 5' end, the sequence is that of nucleotides 1 to 32. At 3' end, the sequence is that of nucleotides 10695 to 10723.

2.3.2 Sequence Comparison

Ten nucleotide differences have been detected with regard to the parent LAV2 genomic sequence. VDV2 vaccine strain is derived from LAV2, through virus sanitization and passage from dog to monkey cells.

Differences between LAV2 and VDV2 can have several origins. First, cloning steps can select a viral subpopulation that is not 100% identical to the major sequence previously detected in LAV2. Second, LAV2 has been produced on PDK cells, whereas VDV2 has been made on Vero cells. Such passage from dog to monkey cells is known to potentially induce virus changes that reflect adaptation to the new cell line. Third, as for all RNA viruses, the lower viral RNA polymerase fidelity triggers a higher genomic mutation rate than DNA polymerases do.

In term of sequences, all 9 nucleotide positions which have been linked to viral attenuation of LAV2 are conserved in VDV2 passage 11.

Furthermore, sequence comparison between VDV2 passage 9 and passage 11 showed the occurrence of two mutations between passages 9 and 11 which are linked to differences in phenotype, viremia and immunogenicity.

TABLE 8

Sequence comparison between LAV2/PDK53 strain and VDV2 passages 9 and 11 strains

| Nucleotides | | | | Amino acids | | | | |
|---|---|---|---|---|---|---|---|---|
| | | VDV2 | | | | | VDV2 | |
| Position | LAV2 | Passage 9 | Passage 11 | Region | Position | LAV2 | Passage 9 | Passage 11 |
| 736 | G | **G** | **C** | M | 9 | G | **G** | **R** |
| 1619 | G | A | A | E | 228 | G | E | E |
| 1638 | A | G | G | E | 234 | K | K | K |
| 2520 | G | A | A | NS1 | 33 | K | K | K |
| 4723 | T | A | A | NS3 | 69 | S | T | T |
| 5062 | G | C | C | NS3 | 181 | D | H | H |
| 5270 | A/T | A | A | NS3 | 250 | E/V | V | V |
| 9191 | G | **G** | **A** | NS5 | 541 | R | **R** | **K** |
| 9222 | A | G | G | NS5 | 551 | E | E | E |
| 10063 | T | A | A | NS5 | 832 | S | T | T |
| 10507 | A | G | G | 3' nc | — | — | — | — |

Bold: sequence differences between VDV2 passage 9 and passage 11/

When performing sequence alignment between all available Genbank serotype 2 Dengue genomic sequences, it appears that only two positions are shared by other Dengue 2 strains (1638 and 2520), both silent at amino acid level. All other positions are specific to the VDV2 passage 11 strain, triggering an amino acid substitution (Table 8). Concerning amino acid changes, the four changes in non-structural peptides appear relatively conservative, from a biochemical point of view, whereas the two changes in M and in the envelope bring modification both in charge and hydrophobicity.

Example 3

Characterization

The objective of these studies was to assess whether changes in attenuation markers occurred through passages.

Figure 1:
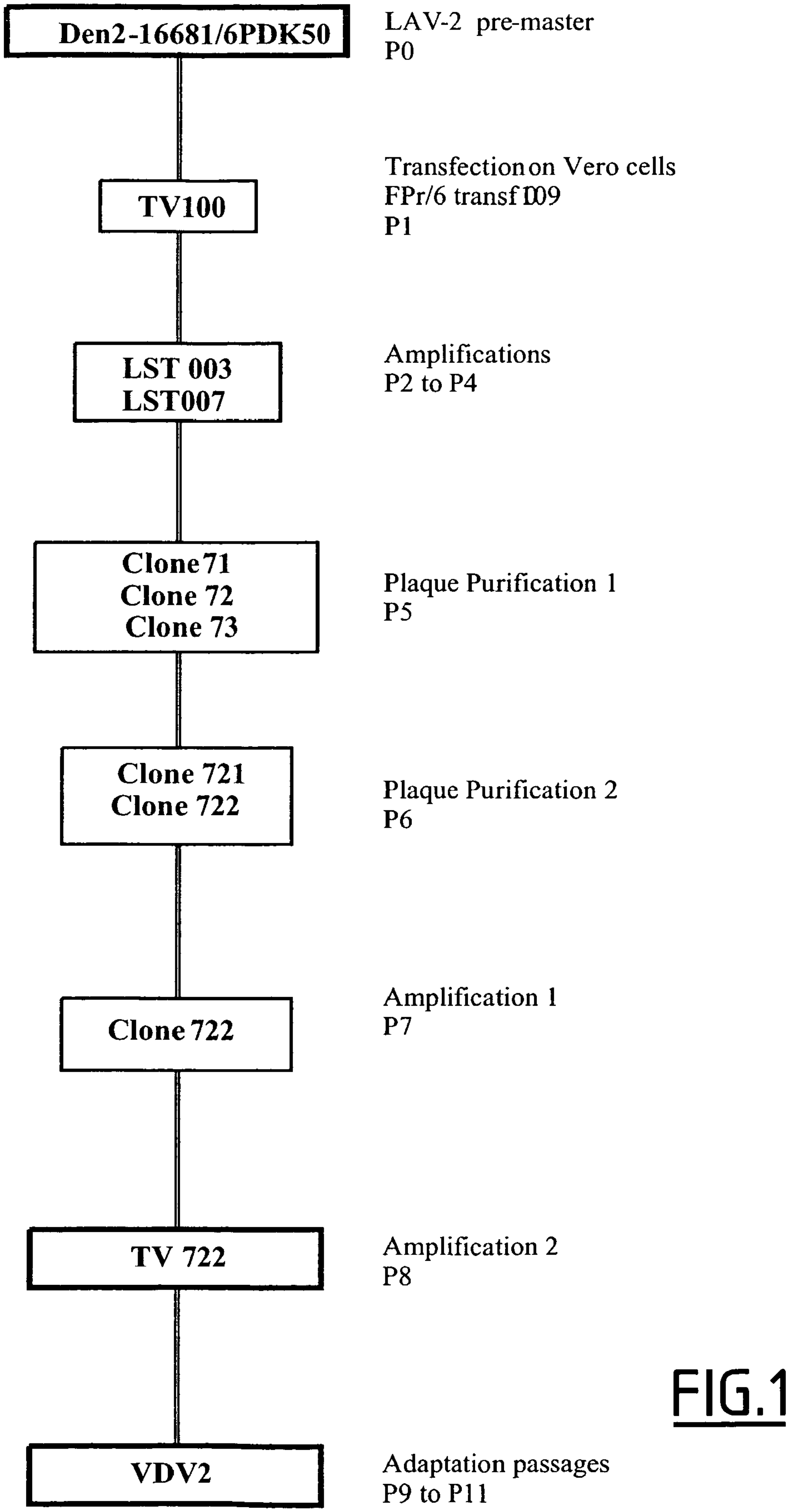
FIG. 1 is a summary of History of VDV2 seed.
Figure 2:
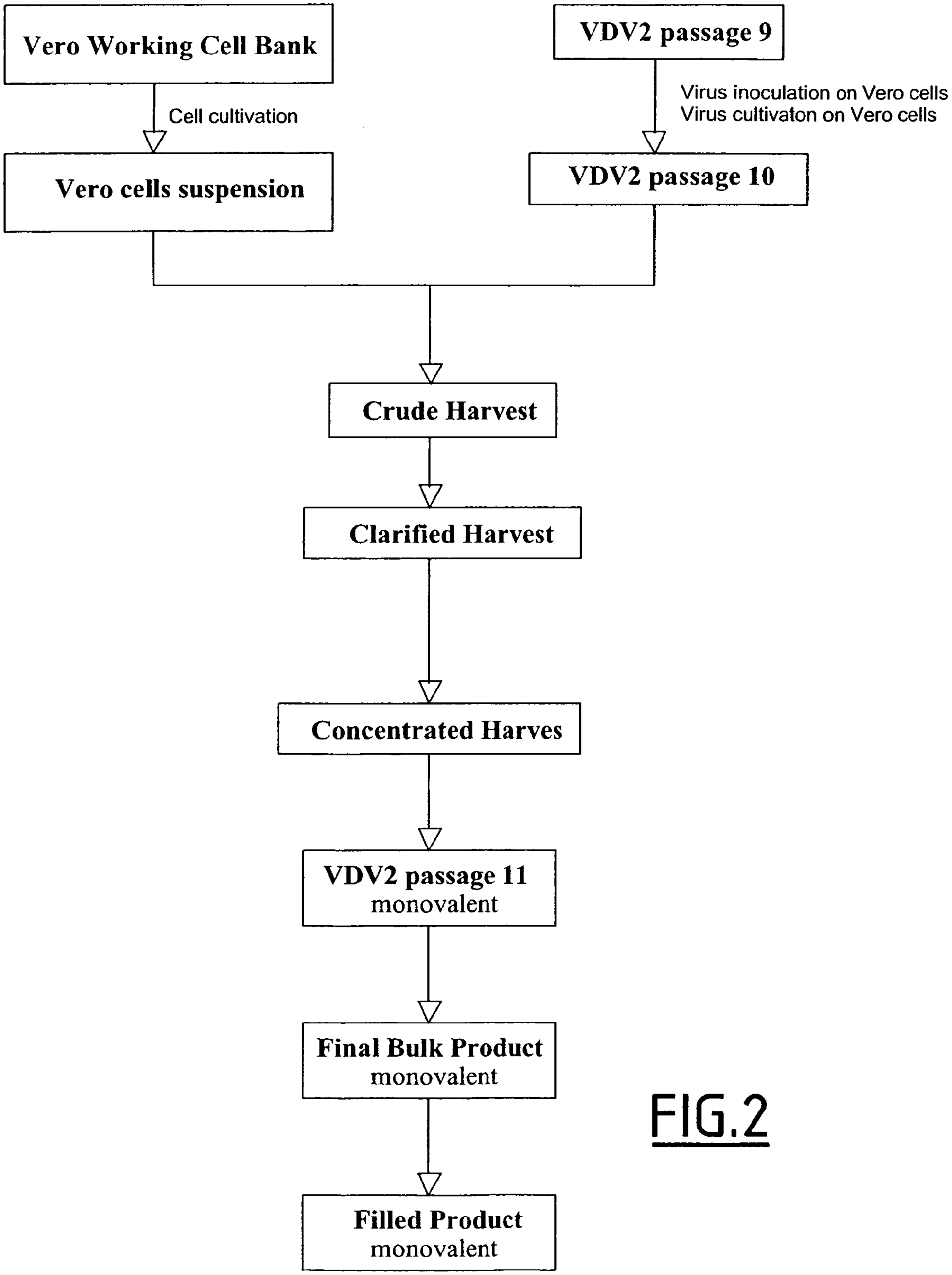
FIG. 2 is a flow chart that summarises the developed manufacturing process that gives rise to the Filled Product (monovalent), "ready to use" doses.

The flow chart shown on FIG. 2 summarises the developed manufacturing process that gives rise to the Filled Product (monovalent), "ready to use" doses.

Briefly, after 2 successive passages on Vero cells of the VDV2 passage 8, the respective working seeds were obtained. The final virus cultivations are also conducted by infection of a Vero cell suspension. The viruses produced are then harvested. DesoxyRiboNucleic Acid (DNA) is digested according to an enzymatic treatment. Impurities are removed by ultrafiltration. Infectious titers are enhanced by a concentration step. An aqueous buffered solution comprising cryoprotective agents (pH=7.5) is added and this 0.22-μm filtrated mixture is then diluted at the targeted dose within the same solution. The active substance is then filled into glass vials, freeze-dried, and stored before use.

3.1 Phenotypic Markers

Table 9 presents data from three phenotypic assays performed on DEN-2 16681 wt strain, DEN-2 16681/PDK53 vaccine strain, VDV2 passage 9 and VDV2 passage 11 (last adaptation passage): temperature-sensitivity (Ts), growth curves on monkey (Vero) and mosquito (C6/36) cells and neurovirulence in Newborn mice (data obtained at CDC). Reduced mouse neurovirulence (reduced mortality and longer average survival time (AST)), restricted-growth at 39° C. and restricted replication on C6/36 are currently accepted by the scientific community as attenuation criteria for Dengue viruses. Vero-adapted passages exhibit clear Ts profile, and are more restricted than DEN2/PDK53. Final adaptation passage is restricted by about 3 log in this assay. Temperature sensitivity was also confirmed by viral growth curves. On Vero cells, similar replication levels were observed with all tested viruses. On mosquito cells, viral growth of Vero-adapted viruses was clearly restricted (about 3 log) compared to wt DEN2, and slightly restricted (about 0.5 log) compared to DEN2-PDK53. Surprisingly, mouse neurovirulence of Vero-adapted viruses was close to neurovirulence of wt DEN2, and significantly higher than neurovirulence of DEN2/PDK53 vaccine. These data point out the low predictive value of this say, with regard to viral strain attenuation (cf clinical data).

Plaque size distribution of VDV2 passages 9 and 11, DEN2/PDK53 and wtDEN2 are compared to FIG. 5. Wt DEN2 exhibits heterogenous profile with 95% of plaques with a size homogeneous profile, with a major population (81%) of plaques<0.6 mm and a minor population (12%) of 1-2 mm plaques. This profile is close to, but distinct from DEN2-PDK53 profile. Noteworthy, the intermediate adaptation passage, VDV2 P9, exhibits a more heterogeneous profile, with a major population (70%) of 1-2 mm plaques, and a minor population (25%) of plaques<0.6 mm. These data demonstrate that VDV2 strain was not yet fully adapted at passage 9, and that the two additional passages were required for obtention of a homogeneous population replicating stably in Vero cells.

Example 4

Immunogenicity, Viremia, and Toxicology in Monkeys

The most solid and numerous data that can be obtained in monkeys concern immunogenicity and viremia. Viremia, in particular, has been identified as one of the factors associated with virulence and disease severity in humans, and then constitute an important parameter to consider. Obviously, immunogenicity is a key parameter when testing vaccines.

Inventors have established minimal/maximal values for viremia and immunogenicity.

TABLE 10

Minimal requirements for responses induced by Dengue vaccine candidates in monkeys, as measured in Vero or LLC-MK2 cells by plaque assay (these cells being considered equivalent in such an assay)

| Viremia mean duration (days) (all serotypes being considered) | Viremia mean peak titer (log 10 pfu) (all serotypes being considered) | Mean neutralizing titer Day 30 (for each serotype) PRNT 50 |
|---|---|---|
| ≦3 days | ≦1.5-2 | ≧80 |

pfu: plaque forming unit
PRNT 50: Plaque Reduction Neutralization Titer 50 (titre corresponding to a reduction of 50% of plaque number)

4.1 Pre-Clinical Pharmacology, Pharmacokinetics, and Product Metabolism in Animals 4.1.1 Material and Methods 4.1.1.1 Monkey Experiments Monkey experiments were carried out according to European guidelines regarding animal experiments.

Immunizations were performed on cynomolgus monkeys (*Macaca fascicularis*) originating from Mauritius (CRP Le Vallon). Monkeys were quarantined for 6 weeks in the animal facility of Sanofi Pasteur before immunization.

Monkeys were immunized by subcutaneous (SC) route in the arm with vaccines in a volume of 0.5 ml (see each respective section). After light anesthesia with ketamine (Imalgene, Merial), blood was collected by puncture of the inguinal or saphene veins. At days 0 and 28, 5 ml of blood were sampled for evaluating antibody responses while between days 2 and 10 only 1 ml of blood was sampled for evaluating viremia. Blood was collected on ice and kept on ice until serum sepa-

TABLE 9

Summary of DEN-2 viral phenotypes

| | Temperature sensitivity (Percent titer reduction at 39° C.)$_{Fold\text{-}reduction}$ | | | | | Growth curves (Peak $log_{10}$ pfu/ml) Vero-LS10 | | Neurovirulence in newborn Swiss Webster mice | |
|---|---|---|---|---|---|---|---|---|---|
| Virus | Score | Day 3 | Day 4 | Day 5 | Day 6 | Titer | at Day | Mortality$_n$ | AST (S.D.) |
| D2-16681 | + | n.d. | $92.7_{13.7}$ | n.d. | $92.2_{12.8}$ | 7.5 | 8 | $100.0\%_{16}$ | 12.2 (1.5) |
| D2-PDK53 | + | n.d. | $96.6_{29.4}$ | n.d. | $99.7_{333.3}$ | 7.3 | 8-10 | $43.75\%_{16}$ | 16.0 (2.4) |
| VDV2 P9 | + | n.d. | $99.94_{1666.7}$ | n.d. | $99.97_{3333.3}$ | 7.5 | 8-10 | $100.0\%_{16}$ | 10.9 (0.7) |
| VDV2 P11 | + | n.d. | $99.92_{1250.0}$ | n.d. | $99.88_{833}$ | 7.5 | 10 | $100.0\%_{16}$ | 10.9 (0.6) |

$_n$number of animals.

ration. To do so, blood was centrifuged for 20 minutes at 4° C., and serum collected and stored at −80° C. until testing in Rich Kinney's laboratory. Shipment to USA was performed in dry ice.

4.1.1.2 Viremia and Neutralizing Antibody Responses (Plaque Reduction Neutralization Test, PRNT)

All analyses were performed in the laboratory of R. Kinney in CDC, Fort Collins, USA. Serum samples were shipped and stored at −80° C. until the time of testing. At the time of first thawing, the samples were tested for viremia, and a 1:5 dilution of the serum was made. The 1:5 serum dilutions were inactivated for 30 min at 56° C. before testing for neutralizing antibodies.

4.1.1.2.1 Viremia 0.125 ml of serum was added to 0.125 ml of diluent (RPMI medium) in the first well of 96-well plate and serial 10-fold dilution series were done, transferring 0.025 ml into 0.225 ml of diluent for each dilution. 0.2 ml of $10^{0.3}$-$10^{5.3}$ dilution series was plated in 6-well plate of Vero cells (virus was adsorbed at 37° C. for 1.5 hour, overlayed with 4 ml of agarose lacking neutral red, overlayed 6-7 days later with 2 ml of agarose containing neutral red, and plaques counted). The limit of virus detection was =10 PFU/ml. For controls stock DEN-16681 PDK-53 (LAV2) vaccine was plated.

4.1.1.2.2 PRNT (Plaque Reduction Neutralization Test)

Neutralizing antibodies were quantified as described in Huang et al. (2000). Briefly, 0.2 ml of heat-inactivated, 1:5 dilution of serum was added to the first well of 96-well plate and serial 2-fold dilution series were made, transferring 0.1 ml into 0.1 ml of diluent (RPMI medium) for each dilution. This resulted in a 1:10-1:320 serum dilution series. 0.1 ml of DEN virus (60-160 PFU; parental DEN2 16681 virus) was added to each serum dilution well for a total of 0.2 ml of serum-virus mixture. 96-well plates were incubated overnight at 4° C. 0.1 ml of serum-virus mixtures (containing 30-80 PFU of input virus) were plated in 6-well Vero plates (as indicated above in the Viremia section) and plaques were counted after staining with neutral red. Multiple back titrations of the input viruses at 2-fold, 1-fold, and 0.5-fold test concentrations provided direct experimental determination of the input PFU, which was the basis for determining 50% ($PRNT_{50}$) and 70% ($PRNT_{70}$) endpoint antibody titers. A negative serum result should have a neutralizing antibody titer of <1:10. Sera showing neutralization titers of 320 were retested at dilutions 1:80-1:2560 for determination of endpoint titer.

4.1.2 Evaluation of Monovalent VDV2 Candidate at Passage 9 in Monkeys

Purification/selection of VDV2 candidate has been conducted as described in example 1. The selected clones (based on phenotypic markers and sequence) have been tested after 9 passages in cell culture in Sanofi Pasteur on male cynomolgus macaques (*Macaca fascicularis*, mean weight 3.1 kg) originating from CRP Le Vallon, Mauritius.

After immunization on D0, viremia was followed from D2 to D10, and immunogenicity measured at D0 and D28. All viruses and vaccines, when in liquid form, were kept at −70° C.

LAV2: titre: $10^{3.93}$ $DICC_{50}$/ml; lyophilized, resuspended in 0.5 ml of PBS (containing $Ca^{2+}$ and $Mg^{2+}$; $CaCl_2.2H_2O$ 0.133 g/l; $MgCl_2.6H_2O$, 0.1 g/l) and administered in totality.

Passage VDV2 DEN2-TV722 (2 plaque purifications+1 amplification): Titre: $10^{5.6}$ $DICC_{50}$/ml; liquid, diluted at $10^{5.3}$ pfu/ml in PBS (containing $Ca^{2+}$ and $Mg^{2+}$; $CaCl_2.2H_2O$ 0.133 g/l; $MgCl_2.6H_2O$, 0.1 g/l); 0.5 ml administered.

Injection was done by SC route in the arm with a 23G1 needle, at a $10^5$ $DICC_{50}$ dose for VDV2.

The results are as presented in Table 11. Titration at day 28 were carried out in triplicate for both $PRNT_{70}$ or and $PRNT_{50}$.

The comparison between VDV2 and LAV2 showed clear differences in viremia, with high viremia of short duration for VDV2 in ¾ monkeys compared to LAV2, and significant immunogenicity for both types (rather lower for VDV2). This viremia may be considered as too high for VDV2 at this pre-master level after only a few passages on Vero cells. However, wild type DEN-2 (and other types too) induce viremia of longer duration (6 to 7 days) and intensity (up to 5 logs plaque forming units [pfu]) (Monath et al., 2000; Bray et al., 1996).

TABLE 11

VDV2 passage 9 immunogenicity

| | | Neutralizing Antibody Titer | | | | Viremia (PFU/ml in Vero cells) | | | | | | | | | |
|---|---|---|---|---|---|---|---|---|---|---|---|---|---|---|---|
| | | Day (−15) | | Day 28 | | Day | Day | Day | Day | Day | Day | Day | Day | Day | Day |
| Serum | Group | $PRNT_{70}$ | $PRNT_{50}$ | $PRNT_{70}$ | $PRNT_{50}$ | −15 | 2 | 3 | 4 | 5 | 6 | 7 | 8 | 9 | 10 |
| AD 097 | LAV DEN-2 | <10 | <10 | 80/80/160 | 320/160/320 | 0 | 0 | 0 | 0 | 0 | 0 | 5 | 0 | 50 | 20 |
| AC 170 | | <10 | <10 | 160/80/320 | 320/160/640 | 0 | 0 | 0 | 0 | 0 | 5 | 5 | 0 | 0 | 0 |
| AD 677 | | <10 | <10 | 1280/640/2560 | 2560/1280/2560 | 0 | 5 | 0 | 0 | 10 | 50 | 0 | 5 | 0 | 0 |
| AC 182 | | <10 | <10 | 320/320/320 | 640/1280/1280 | 0 | 0 | 5 | 0 | 15 | 5 | 0 | 5 | 0 | 0 |
| AC 658 | VDV DEN-2 | <10 | <10 | 160/160/160 | 320/160/640 | 0 | 550 | 35 | 0 | 0 | 0 | 0 | 0 | 0 | 0 |
| AC 512 | | <10 | <10 | 160/80/160 | 160/160/160 | 0 | 1650 | 35 | 0 | 5 | 0 | 0 | 0 | 0 | 0 |
| AD 608 | | <10 | <10 | 160/320/160 | 320/320/320 | 0 | 1700 | 60 | 100 | 0 | 0 | 0 | 0 | 0 | 0 |
| AD 132 | | <10 | <10 | 80/80/80 | 80/160/160 | 0 | 70 | 10 | 0 | 50 | 10 | 100 | 0 | 0 | 0 |
| Virus DEN-2 | Exp#1 60PFU | Exp#2 54PFU | Exp#3 46PFU | | | | | | | | | | | | |

4.1.3 Evaluation of Monovalent VDV2 Candidate at Passage 11

As immunogenicity of the vaccines had been tested at the passage 9, a further experiment was designed to test the monovalent passage after two additional passages (passage 10).

TABLE 12 passage 11 VDV2 immunogenicity and viremia

| | | Neutralizing Antibody Titer | | | | Viremia (PFU/ml in Vero cells) | | | | | | | | |
|---|---|---|---|---|---|---|---|---|---|---|---|---|---|---|
| | | Day (−14) | | Day 29 | | Day | Day | Day | Day | Day | Day | Day | Day | Day |
| Monkey | Group | $PRNT_{50}$ | $PRNT_{70}$ | $PRNT_{50}$ | $PRNT_{50}$ | −14 | 3 | 4 | 5 | 6 | 7 | 8 | 9 | 10 |
| AE 971 | VDV DEN-2 | — | — | 180 | 80 | 0 | 0 | 0 | 0 | 0 | 0 | 0 | 0 | 0 |
| AE 990 | | — | — | 160 | 50 | 0 | 15 | 0 | 0 | 5 | 0 | 0 | 0 | 0 |
| AE 998 | | — | — | 905 | 508 | 0 | 0 | 0 | 0 | 0 | 0 | 0 | 0 | 0 |
| AF 182 | | — | — | 285 | 101 | 0 | 0 | 0 | 0 | 0 | 0 | 0 | 0 | 0 |
| Geo Mean | homologous | — | — | 293 | 119 | | | | | | | | | |
| AE 538 | Placebo | —/—/—/— | —/—/—/— | 2.5/—/2/2 | —/—/—/— | 0 | 0 | 0 | 0 | 0 | 0 | 0 | 0 | 0 |
| AE 548 | | —/—/—/— | —/—/—/— | —/—/1/2 | —/—/—/— | 0 | 0 | 0 | 0 | 0 | 0 | 0 | 0 | 0 |
| AE 556 | | —/—/1.5/2 | —/—/—/— | 1/—/—/— | —/—/—/— | 0 | 0 | 0 | 0 | 0 | 0 | 0 | 0 | 0 |
| AE 572 | | —/—/1.5/5 | —/—/1.5/2 | 5/—/—/2 | —/—/—/— | 0 | 0 | 0 | 0 | 0 | 0 | 0 | 0 | 0 |
| Geo Mean | | —/—/1.2/3 | —/—/1/1 | 2/—/ 1.2/1.6 | —/—/—/— | | | | | | | | | |
| | | D1/D2/D3/ D4 | D1/D2/D3/ D4 | D1/D2/D3/ D4 | D1/D2/D3/ D4 | | | | | | | | | |

Male *Macaca fascicularis* monkeys were used as before, originating from C.R.P. Le Vallon, Ile Maurice (24 monkeys, mean weight 3.4 kg).

Passage 11 VDV2; Batch: Titre: 8.07 log 10 $DICC_{50}$/ml

Placebo: PBS with $Ca^{2+}$ and $Mg^{2+}$

VDV3: VERO-Derived Vaccine Dengue serotype 3 strain, obtained by sanitization of LAV3 on Vero cells.

VDV4: VERO-Derived Vaccine Dengue serotype 4 strain, obtained by sanitization of LAV4 on Vero cells.

Vaccines were diluted at $10^{5.3}$ $DICC_{50}$/ml in PBS (containing $Ca^{2+}$ and $Mg^{2+}$; $CaCl_2.2H_2O$ 0.133 g/l; $MgCl_2.6H_2O$, 0.1 g/l); 0.5 ml administered by SC route in the arm with a 23G1 needle, corresponding to a dose of $10^5$ $DICC_{50}$.

Viremia and immunogenicity have been measured as usual in CDC by R Kinney. The results are shown in Table 12.

VDV2 passage 11 monovalent vaccine induced a significant immune response, while viremia was low or absent. The absent/low VDV2-induced viremia is to be considered in light of the previous experiment in which the passage 9 VDV2 induced high early viremia. Some evolution between passages 9 and 11 suppressed this high viremia while immunogenicity was maintained. VDV2 therefore constitutes an acceptable candidate.

It is to be noted that in the same experiment, 4 monkeys were vaccinated with a tetravalent formulation involving the same VDV2 passage 11 vaccine; no viremia was detected for VDV1 and VDV2 while VDV3 and VDV4 induced viremia.

Two other experiments involved the administration of VDV2, alone or in combination with the other serotypes.

In the first one (tetravalent study; 5-log of each serotype), no viremia was detected for VDV2, and VDV1, while high levels of viremia were detected for VDV3 and VDV4.

In the second experiment, VDV2 passage 11 was administered alone or within a tetravalent combination including VDV1. When administered alone, VDV2 passage 11 induced a low viremia (peak 40) in only 1 out of 4 monkeys while the 3 others were negative. When present within tetravalent formulations, VDV2 induced no or dramatically lower viremia than VDV3 and VDV4, even though VDV2 was administered at 4 log while VDV3 and VDV4 were administered at 2 log. This demonstrates the higher safety of VDV2, as far as viremia is concerned. Monovalent VDV2 thus fulfilled the success criteria initially defined in monkeys.

4.2 Toxicology of VDV2

4.2.1 Neurovirulence Tests in Monkeys

The objective of this test was to demonstrate the lack of neurotropic properties in monkeys (Ph. Eur. 2.6.18) of the attenuated 2 dengue virus seed produced by Sanofi Pasteur.

10 cynomolgus monkeys from Mauritius were inoculated with VDV2 passage 9 by the intracerebral route ($10^{7.10}$ $CCID_{50}$/ in the thalamus of each hemisphere). At the end of the test, the monkeys were sacrificed and perfused with formaline solution. Tissue samples were taken from the brain of each monkey (medulla oblongata, pons and cerebellum, midbrain, thalamus including the left and the right parts, the left and the right of the cerebral cortex). Sections were cut at a thickness of 8 μm and stained by eosin and gallocyanin.

No histopathological signs of pathogenicity were observed in the monkey brains injected with serotype 2 primary virus seed.

4.2.2 GLP Toxicity Study in the Cynomolgus Monkey after 1 Subcutaneous Administration of VDV2 Followed by a 28-Day Observation Period The objective of this GLP study was to assess the interactions between VDV2 passage 9 and other Dengue vaccine candidates. The 1st step of the study was to assess the safety and immunogenicity of VDV2 prior to the administration of another vaccine candidate.

One human dose of VDV2 (approximately $10^4$ $CCID_{50}$ per dose) was administered subcutaneously on Day 0 to cynomolgus monkeys (4 males and 4 females). A control group of 2 males and 2 females received the vehicle (4% NaCl).

Mortality, clinical condition, body weight, and food consumption were monitored throughout the study. Body temperature was taken once pre-test, daily from the day of each administration and during 2 days after. Blood samples were taken for clinical laboratory determinations once pre-test and on Days 8 and 27.

There were no effects on clinical signs, body weight, food consumption, dermal reactions, body temperature, haematology, clinical chemistry, or organ weights. No deaths were reported during the study.

In conclusion, the subcutaneous administration of VDV2 to the cynomolgus monkey (*Macaca fascicularis*) at the test doses did not adversely affect the health of the monkeys as assessed by in-life clinical observations and clinical pathology.

Example 5

Safety of Monovalent VDV2 in Healthy, Flavivirus-Naive Adults Aged 18 to 40 Years The aim of this phase 1 trial is to document the safety, viremia, and immunogenicity profiles of monovalent VDV2 passage 11 at a virus concentration of $10^4$ $CCID_{50}$ compared to Stamaril® (used as control group) in flavivirus-naive adults. Single injections are given, with follow-up at 6 and 12 months. For safety precaution, sequential inclusions are performed in the study.

Enrollment and vaccinations are therefore staggered; a 1st cohort (n=4 per group, total n=12) have been vaccinated. The safety data collected up to Day 28 have been reviewed by an Independent Data Monitoring Committee (IDMC) and by the Royal Adelaide Hospital Investigational Drugs Subcommittee (IDSC) before deciding to proceed with the vaccination of the remaining subjects (n=8 per group, total n=16). A schematic representation of the trial design is provided in FIG. 6.

After administration of the vaccine the patient are regularly submitted to various clinical examination and testing. A summary of this follow up is given in Table 13 below.

The enrolled population consists of adults aged 18 to 40 years (i.e. the day of the 18th birthday to the day before the 41st birthday) on day of inclusion who are flaviviruses-naïve [persons presenting vaccination against flavivirus diseases (e.g. yellow fever, Japanese encephalitis, dengue fever); or history of flavivirus infection (confirmed either clinically, serologically or microbiologically) or previous residence in or travel to areas with high dengue infection endemicity (whatever the duration), or residence in or travel to North Queensland for 2 weeks or more) were excluded]

TABLE 13

Flow chart for follow up

| | Visit Number | | | | | | | | | | | |
|---|---|---|---|---|---|---|---|---|---|---|---|---|
| | V 01 | V 02 | V 03 | V 04 | V 05 | V 06 | V 07 | V 08 | V 09 | V 10 | V 11 | V 12 |
| | Trial timelines[□] | | | | | | | | | | | |
| | D 0 | D 2 | D 4 | D 6 | D 8 | D 10 | D 12 | D 14 | D 16 | D 28 | D 180 | D 365 |
| | Time Windows | | | | | | | | | | | |
| | | | | | | ±1 d | ±1 d | | | ±4 d | ±15 d | ±30 d |
| Clinical Examination | √ | √ | √ | √ | √ | √ | √ | √ | √ | √ | √ | √ |
| Vital signs (BP, pulse rate) | √ | | | | | | | | | | | |
| Oral temperature | √ | √ | √ | √ | √ | √ | √ | √ | √ | √ | | |
| Blood Sampling: | | | | | | | | | | | | |
| Serology HBV/HCV/HIV | √ | | √ | | √ | | √ | | √ | √ | | |
| Biological Safety | √ | √ | √ | √ | √ | √ | √ | √ | √ | | | |
| Viremia | √ | | | | | | | | √ | √ | √ | √ |
| Immunogenicity | √ | √ | √ | √ | √ | √ | √ | √ | √ | √ | | |
| Cytokines in serum | √ | | | | | | | | | √ | | |
| PBMCs for T cell (subset) | √ | | | | | | | | | √ | | |
| immediate surveillance | √ | | | | | | | | | | | |
| Local & systemic events | √ | √ | √ | √ | √ | √ | √ | √ | √ | √ | √ | √ |

V: visit
D: day
[□]Time intervals between visits will be calculated from the date of study vaccination which might differ from the date of visit (e.g. in case a temporary exclusion criterion is met). V06 and V07 must be done with at least 1-day interval.

The products tested are:

The vaccine evaluated is a lyophilised product in a vial that is reconstituted extemporaneously with the diluent provided separately:

Active ingredient: 4±0.5 $\log_{10}$ $CCID_{50}$ of monovalent Vero dengue virus serotype 2 (VDV2 passage 11) per 0.5 mL dose;

Diluent: Sterile NaCl 4% solution for vaccine reconstitution.

The reconstituted vaccine, i.e 0.5 mL of NaCl 4% solution of monovalent VDV2, should be used immediately or be maintained until use +2° C. and +8° C.

The 0.5 mL vaccine dose is administered subcutaneously in the deltoid region.

The control vaccine Stamaril®, is a yellow fever vaccine produced by Aventis Pasteur. Stamaril® is presented as a lyophilised, avian-leukosis-free, stabilised product to be reconstituted with a diluent immediately before use. (Active ingredient: Live attenuated yellow fever virus (17D strain): ≧1,000 mouse Lethal Dose 50% ($LD_{50}$)/Diluent: Sterile NaCl 4% solution).

The control vaccine is administered subcutaneously in the deltoid region.

No subject had clinically significant syndrome related to vaccination. One subject had a transient fever (<38° C.). One subject had a local reaction (induration). No serious adverse event related to vaccination was observed.

All subjects have antibodies response 28 days after vaccination against dengue 2 (titer between 1888 and 6393)

REFERENCES

Bhamarapravati, N and Yoksan S. (1997). Dengue and Dengue Hemorrhagic Fever. Live attenuated tetravalent dengue vaccines, CABI Publishing, 367-379.

Burke D S and Monath T P. Flaviviruses (2001) In Knipe D M and Howley P M, eds. Fields Virology 4th ed. Vol 1, 1043-1125

DeFraites R F, Smoak B L, Trofa A F, Hoke C H, Kanesathasan N, King A, MacArthy P O, et al. Dengue fever among U.S. military personnel—Haiti, September-November, 1994. MMWR 1994; 43: 845-848.

Dunnen and Antonarakis (2000) Mutation nomenclature extensions and suggestions to describe complex mutations: a discussion. Hum Mutation. 15:7-12; Erratum in: Hum Mutat 2002; 20(5):403

Gubler D J. Dengue. (1988) In: Epidemiology of arthropod-borne viral disease. Monath T P M, editor, Boca Raton (Fla.): CRC Press: 223-60

Gubler D J, Kuno G. Dengue and Dengue Hemorrhagic Fever. CAB International Publishing 1997

Gubler D. Epidemic dengue/dengue hemorrhagic fever as a public health, social and economic problem in the 21st century. (2002) TRENDS in Microbiology. 10:100-103

Halstead S B and Simasthien P (1970). Observations related to pathogenesis of Dengue haemorrhagic fever. II. Antigenic and biological properties of dengue viruses and their association with disease response in the host. Yale J. Biol. Med; 42: 261-275.

Huang et al. (2000). J. Virol 74; 3020-3028.

Jirakanjanakit N, Khin M M, Yoksan S, Bhamarapravati N. (1999) Dynamics of susceptibility and transmissibility of the live, attenuated, candidate vaccines dengue-1 PDK13, dengue-3 PGMK30F3, and dengue-4 PDK48 after oral infection in *Aedes aegypti*. Am J Trop Med Hyg., 61(4): 672-676

Kautner I, Robinson M J, Kubnle U. (1997) Dengue Virus infection: Epidemiology, pathogenesis, clinical presentation, diagnosis, and prevention. J of Pediatrics; 131:516-524

Monath, T P. (1994) Dengue: the risk to developed and developing countries. Proc Natl Acad Sci; 91: 2395-2400.

Monath T P, Levenbook I, Soike K, Zhang Z X, Ratterree M, Draper K et al. (2000) Chimeric yellow fever virus 17D-Japanese encephalitis virus vaccine: dose-response effectiveness and extended safety testing in rhesus monkeys. Journal of Virology; 74(4):1742-1751

Bray M, Men R, Lai C J. (1996) Monkeys immunized with intertypic chimeric dengue viruses are protected against wild-type virus challenge. J Virol; 70(6):4162-4166

Rigau-Pérez J G, Clark G G, Gubler D J, Reiter P, Sanders E J, Vorndam A V. (1998) Dengue and dengue haemorrhagic fever. Lancet; 352: 971-977.

Rothman A L, Ennis F A. (1999) Immunopathogenesis of dengue hemorrhagic fever. Virology; 257: 1-6

Sabin A B. (1952) Research on dengue during World War II. Am J Trop Med Hyg; 1: 30-50

Shirtcliffe P, Cameron E, Nicholson K G, Wiselka M J. (1998) Don't forget dengue! Clinical features of dengue fever in returning travellers. J Roy Coll Phys Lond.; 32: 235-237.

Thompson J D, Higgins D G, and Gibson T J. (1994) CLUSTAL W: improving the sensitivity of progressive multiple sequence alignment through sequence weighting, position-specific gap penalties and weight matrix choice. Nucl. Acids. Res., 22 (22), 4673-4680

Vaughn D W, Green S, Kalayanarooj S, Innis B L, Nimmannitya S, Suntayakorn S, Rothman A L, Ennis F A, Nisalak A. (1997) Dengue in the early febrile phase: viremia and antibody response. J Infect Dis; 176: 322-30.

Vaughn D W, Green S, Kalayanarooj S, Innis B L, Nimmannitya S, Suntayakorn S, Endy T P, Raengsakulrach B, Rothman A L, Ennis F A, Nisalak A. (2000) Dengue viremia titer, antibody response pattern, and virus serotype correlate with disease severity. J Inf Dis; 181: 2-9.

WHO Technical Guide, 1986. Dengue haemorrhagic fever: diagnosis, treatment and control, p1-2. World Health Organization, Geneva, Switzerland Wu S, Grouard-Vogel G, Sun W, Mascola J, Brachtel E, Putvatana R. (2000) Human skin Langerhans cells are targets of dengue virus infection. Nature Med; 7:816-820

Khin M M, Jirakanjanakit N, Yoksan S, Bhamarapravati N. (1994) Infection, dissemination, transmission, and biological attributes of dengue-2 PDK53 candidate vaccine virus after oral infection in *Aedes aegypti*. Am J Trop Med Hyg., 51(6): 864-869

The invention claimed is:

1. A live attenuated dengue-2 virus strain which comprises sequence SEQ ID NO: 38 wherein at least nucleotides at positions 736, 1619, 4723, 5062, 9191, 10063, and 10507, are mutated, with the proviso that the following nucleotides are not mutated: 57, 524, 2055, 2579, 4018, 5547, 6599, and 8571.

2. The dengue-2 virus strain according to claim 1, wherein at least a nucleotide is further mutated at a position selected from the group consisting of positions 1638, 2520, 9222, and 10361.

3. The dengue-2 virus strain according to claim 1, wherein SEQ ID NO: 38 comprises the mutations 736 G>C, 1619 G>A, 1638 A>G, 2520 G>A, 4723 T>A, 5062 G>C, 9191 G>A, 9222 A>G, 10063 T>A, and 10507 A>G.

4. The dengue-2 virus strain according to claim 1, which further comprise a substitution of one or more nucleotides in a given codon position which results in no alteration in the amino acid encoded at that position.

5. The dengue-2 virus strain according to claim 1, which comprises SEQ ID NO: 1.

6. An immunogenic composition comprising a live attenuated dengue-2 virus strain which comprises sequence SEQ ID NO: 38 wherein at least nucleotides at positions 736, 1619, 4723, 5062, 9191, 10063, and 10507, are mutated, with the proviso that the following nucleotides are not mutated: 57, 524, 2055, 2579, 4018, 5547, 6599, and 8571, in a pharmaceutically acceptable carrier.

7. The immunogenic composition according to claim 6, wherein said live attenuated dengue-2 virus strain comprises SEQ ID NO: 38 in which C at position 736 is substituted for G, A at position 1619 is substituted for G, A at position 4723 is substituted for T, C at position 5062 is substituted for G, A at position 9191 is substituted for G, A at position 10063 is substituted for T, and G at position 10507 is substituted for A.

8. The immunogenic composition according to claim 6, wherein said live attenuated dengue-2 virus strain further comprises a substitution of one or more nucleotides in a given codon position which results in no alteration in the amino acid encoded at that position.

9. The immunogenic composition according to claim 6, wherein said live attenuated dengue-2 virus strain comprises SEQ ID NO: 1.

10. The immunogenic composition according to claim 6, which further comprises at least one live attenuated dengue virus selected from the group consisting of serotype 1, serotype 3, and serotype 4.

* * * * *

UNITED STATES PATENT AND TRADEMARK OFFICE

CERTIFICATE OF CORRECTION

PATENT NO. : 7,641,908 B2
APPLICATION NO. : 11/453344
DATED : January 5, 2010
INVENTOR(S) : Kinney et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 350 days.

Signed and Sealed this

Sixteenth Day of November, 2010

David J. Kappos

*Director of the United States Patent and Trademark Office*

SEQUENCE LISTING

```
<160> NUMBER OF SEQ ID NOS: 42

<210> SEQ ID NO 1
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: VDV2
<220> FEATURE:
<221> NAME/KEY: CDS
<222> LOCATION: (97)..(10272)
<220> FEATURE:
<221> NAME/KEY: misc_feature
<222> LOCATION: (10361)..(10361)
<223> OTHER INFORMATION: unknown

<400> SEQUENCE: 1
```

-continued

```
agttgttagt ctacgtggac cgacaaagac agattctttg agggagctaa gctcaatgta     60

gttctaacag ttttttaatt agagagcaga tctctg atg aat aac caa cgg aaa      114
                                        Met Asn Asn Gln Arg Lys
                                        1               5

aag gcg aaa aac acg cct ttc aat atg ctg aaa cgc gag aga aac cgc      162
Lys Ala Lys Asn Thr Pro Phe Asn Met Leu Lys Arg Glu Arg Asn Arg
            10                  15                  20

gtg tcg act gtg caa cag ctg aca aag aga ttc tca ctt gga atg ctg      210
Val Ser Thr Val Gln Gln Leu Thr Lys Arg Phe Ser Leu Gly Met Leu
        25                  30                  35

cag gga cga gga cca tta aaa ctg ttc atg gcc ctg gtg gcg ttc ctt      258
Gln Gly Arg Gly Pro Leu Lys Leu Phe Met Ala Leu Val Ala Phe Leu
    40                  45                  50

cgt ttc cta aca atc cca cca aca gca ggg ata ttg aag aga tgg gga      306
Arg Phe Leu Thr Ile Pro Pro Thr Ala Gly Ile Leu Lys Arg Trp Gly
55                  60                  65                  70

aca att aaa aaa tca aaa gct att aat gtt ttg aga ggg ttc agg aaa      354
Thr Ile Lys Lys Ser Lys Ala Ile Asn Val Leu Arg Gly Phe Arg Lys
                75                  80                  85

gag att gga agg atg ctg aac atc ttg aat agg aga cgc aga tct gca      402
Glu Ile Gly Arg Met Leu Asn Ile Leu Asn Arg Arg Arg Arg Ser Ala
            90                  95                  100

ggc atg atc att atg ctg att cca aca gtg atg gcg ttc cat tta acc      450
Gly Met Ile Ile Met Leu Ile Pro Thr Val Met Ala Phe His Leu Thr
        105                 110                 115

aca cgt aac gga gaa cca cac atg atc gtc agc aga caa gag aaa ggg      498
Thr Arg Asn Gly Glu Pro His Met Ile Val Ser Arg Gln Glu Lys Gly
    120                 125                 130

aaa agt ctt ctg ttt aaa aca gag gtt ggc gtg aac atg tgt acc ctc      546
Lys Ser Leu Leu Phe Lys Thr Glu Val Gly Val Asn Met Cys Thr Leu
135                 140                 145                 150

atg gcc atg gac ctt ggt gaa ttg tgt gaa gac aca atc acg tac aag      594
Met Ala Met Asp Leu Gly Glu Leu Cys Glu Asp Thr Ile Thr Tyr Lys
                155                 160                 165

tgt ccc ctt ctc agg cag aat gag cca gaa gac ata gac tgt tgg tgc      642
Cys Pro Leu Leu Arg Gln Asn Glu Pro Glu Asp Ile Asp Cys Trp Cys
            170                 175                 180

aac tct acg tcc acg tgg gta act tat ggg acg tgt acc acc atg gga      690
Asn Ser Thr Ser Thr Trp Val Thr Tyr Gly Thr Cys Thr Thr Met Gly
        185                 190                 195

gaa cat aga aga gaa aaa aga tca gtg gca ctc gtt cca cat gtg cga      738
Glu His Arg Arg Glu Lys Arg Ser Val Ala Leu Val Pro His Val Arg
    200                 205                 210

atg gga ctg gag aca cga act gaa aca tgg atg tca tca gaa ggg gcc      786
Met Gly Leu Glu Thr Arg Thr Glu Thr Trp Met Ser Ser Glu Gly Ala
215                 220                 225                 230

tgg aaa cat gtc cag aga att gaa act tgg atc ttg aga cat cca ggc      834
Trp Lys His Val Gln Arg Ile Glu Thr Trp Ile Leu Arg His Pro Gly
                235                 240                 245

ttc acc atg atg gca gca atc ctg gca tac acc ata gga acg aca cat      882
Phe Thr Met Met Ala Ala Ile Leu Ala Tyr Thr Ile Gly Thr Thr His
            250                 255                 260

ttc caa aga gcc ctg att ttc atc tta ctg aca gct gtc act cct tca      930
Phe Gln Arg Ala Leu Ile Phe Ile Leu Leu Thr Ala Val Thr Pro Ser
        265                 270                 275

atg aca atg cgt tgc ata gga atg tca aat aga gac ttt gtg gaa ggg      978
Met Thr Met Arg Cys Ile Gly Met Ser Asn Arg Asp Phe Val Glu Gly
    280                 285                 290
```

-continued

```
gtt tca gga gga agc tgg gtt gac ata gtc tta gaa cat gga agc tgt      1026
Val Ser Gly Gly Ser Trp Val Asp Ile Val Leu Glu His Gly Ser Cys
295                 300                 305                 310

gtg acg acg atg gca aaa aac aaa cca aca ttg gat ttt gaa ctg ata      1074
Val Thr Thr Met Ala Lys Asn Lys Pro Thr Leu Asp Phe Glu Leu Ile
                315                 320                 325

aaa aca gaa gcc aaa cag cct gcc acc cta agg aag tac tgt ata gag      1122
Lys Thr Glu Ala Lys Gln Pro Ala Thr Leu Arg Lys Tyr Cys Ile Glu
            330                 335                 340

gca aag cta acc aac aca aca aca gaa tct cgc tgc cca aca caa ggg      1170
Ala Lys Leu Thr Asn Thr Thr Thr Glu Ser Arg Cys Pro Thr Gln Gly
        345                 350                 355

gaa ccc agc cta aat gaa gag cag gac aaa agg ttc gtc tgc aaa cac      1218
Glu Pro Ser Leu Asn Glu Glu Gln Asp Lys Arg Phe Val Cys Lys His
    360                 365                 370

tcc atg gta gac aga gga tgg gga aat gga tgt gga cta ttt gga aag      1266
Ser Met Val Asp Arg Gly Trp Gly Asn Gly Cys Gly Leu Phe Gly Lys
375                 380                 385                 390

gga ggc att gtg acc tgt gct atg ttc aga tgc aaa aag aac atg gaa      1314
Gly Gly Ile Val Thr Cys Ala Met Phe Arg Cys Lys Lys Asn Met Glu
                395                 400                 405

gga aaa gtt gtg caa cca gaa aac ttg gaa tac acc att gtg ata aca      1362
Gly Lys Val Val Gln Pro Glu Asn Leu Glu Tyr Thr Ile Val Ile Thr
            410                 415                 420

cct cac tca ggg gaa gag cat gca gtc gga aat gac aca gga aaa cat      1410
Pro His Ser Gly Glu Glu His Ala Val Gly Asn Asp Thr Gly Lys His
        425                 430                 435

ggc aag gaa atc aaa ata aca cca cag agt tcc atc aca gaa gca gaa      1458
Gly Lys Glu Ile Lys Ile Thr Pro Gln Ser Ser Ile Thr Glu Ala Glu
    440                 445                 450

ttg aca ggt tat ggc act gtc aca atg gag tgc tct cca aga acg ggc      1506
Leu Thr Gly Tyr Gly Thr Val Thr Met Glu Cys Ser Pro Arg Thr Gly
455                 460                 465                 470

ctc gac ttc aat gag atg gtg ttg ctg cag atg gaa aat aaa gct tgg      1554
Leu Asp Phe Asn Glu Met Val Leu Leu Gln Met Glu Asn Lys Ala Trp
                475                 480                 485

ctg gtg cac agg caa tgg ttc cta gac ctg ccg tta cca tgg ttg ccc      1602
Leu Val His Arg Gln Trp Phe Leu Asp Leu Pro Leu Pro Trp Leu Pro
            490                 495                 500

gga gcg gac aca caa gag tca aat tgg ata cag aag gag aca ttg gtc      1650
Gly Ala Asp Thr Gln Glu Ser Asn Trp Ile Gln Lys Glu Thr Leu Val
        505                 510                 515

act ttc aaa aat ccc cat gcg aag aaa cag gat gtt gtt gtt tta gga      1698
Thr Phe Lys Asn Pro His Ala Lys Lys Gln Asp Val Val Val Leu Gly
    520                 525                 530

tcc caa gaa ggg gcc atg cac aca gca ctt aca ggg gcc aca gaa atc      1746
Ser Gln Glu Gly Ala Met His Thr Ala Leu Thr Gly Ala Thr Glu Ile
535                 540                 545                 550

caa atg tca tca gga aac tta ctc ttc aca gga cat ctc aag tgc agg      1794
Gln Met Ser Ser Gly Asn Leu Leu Phe Thr Gly His Leu Lys Cys Arg
                555                 560                 565

ctg aga atg gac aag cta cag ctc aaa gga atg tca tac tct atg tgc      1842
Leu Arg Met Asp Lys Leu Gln Leu Lys Gly Met Ser Tyr Ser Met Cys
            570                 575                 580

aca gga aag ttt aaa gtt gtg aag gaa ata gca gaa aca caa cat gga      1890
Thr Gly Lys Phe Lys Val Val Lys Glu Ile Ala Glu Thr Gln His Gly
        585                 590                 595

aca ata gtt atc aga gtg caa tat gaa ggg gac ggc tct cca tgc aag      1938
Thr Ile Val Ile Arg Val Gln Tyr Glu Gly Asp Gly Ser Pro Cys Lys
    600                 605                 610
```

-continued

```
atc cct ttt gag ata atg gat ttg gaa aaa aga cat gtc tta ggt cgc      1986
Ile Pro Phe Glu Ile Met Asp Leu Glu Lys Arg His Val Leu Gly Arg
615                 620                 625                 630

ctg att aca gtc aac cca att gtg aca gaa aaa gat agc cca gtc aac      2034
Leu Ile Thr Val Asn Pro Ile Val Thr Glu Lys Asp Ser Pro Val Asn
                635                 640                 645

ata gaa gca gaa cct cca ttt gga gac agc tac atc atc ata gga gta      2082
Ile Glu Ala Glu Pro Pro Phe Gly Asp Ser Tyr Ile Ile Ile Gly Val
            650                 655                 660

gag ccg gga caa ctg aag ctc aac tgg ttt aag aaa gga agt tct atc      2130
Glu Pro Gly Gln Leu Lys Leu Asn Trp Phe Lys Lys Gly Ser Ser Ile
        665                 670                 675

ggc caa atg ttt gag aca aca atg agg ggg gcg aag aga atg gcc att      2178
Gly Gln Met Phe Glu Thr Thr Met Arg Gly Ala Lys Arg Met Ala Ile
    680                 685                 690

tta ggt gac aca gcc tgg gat ttt gga tcc ttg gga gga gtg ttt aca      2226
Leu Gly Asp Thr Ala Trp Asp Phe Gly Ser Leu Gly Gly Val Phe Thr
695                 700                 705                 710

tct ata gga aag gct ctc cac caa gtc ttt gga gca atc tat gga gct      2274
Ser Ile Gly Lys Ala Leu His Gln Val Phe Gly Ala Ile Tyr Gly Ala
                715                 720                 725

gcc ttc agt ggg gtt tca tgg act atg aaa atc ctc ata gga gtc att      2322
Ala Phe Ser Gly Val Ser Trp Thr Met Lys Ile Leu Ile Gly Val Ile
            730                 735                 740

atc aca tgg ata gga atg aat tca cgc agc acc tca ctg tct gtg aca      2370
Ile Thr Trp Ile Gly Met Asn Ser Arg Ser Thr Ser Leu Ser Val Thr
        745                 750                 755

cta gta ttg gtg gga att gtg aca ctg tat ttg gga gtc atg gtg cag      2418
Leu Val Leu Val Gly Ile Val Thr Leu Tyr Leu Gly Val Met Val Gln
    760                 765                 770

gcc gat agt ggt tgc gtt gtg agc tgg aaa aac aaa gaa ctg aaa tgt      2466
Ala Asp Ser Gly Cys Val Val Ser Trp Lys Asn Lys Glu Leu Lys Cys
775                 780                 785                 790

ggc agt ggg att ttc atc aca gac aac gtg cac aca tgg aca gaa caa      2514
Gly Ser Gly Ile Phe Ile Thr Asp Asn Val His Thr Trp Thr Glu Gln
                795                 800                 805

tac aaa ttc caa cca gaa tcc cct tca aaa cta gct tca gct atc cag      2562
Tyr Lys Phe Gln Pro Glu Ser Pro Ser Lys Leu Ala Ser Ala Ile Gln
            810                 815                 820

aaa gcc cat gaa gag gac att tgt gga atc cgc tca gta aca aga ctg      2610
Lys Ala His Glu Glu Asp Ile Cys Gly Ile Arg Ser Val Thr Arg Leu
        825                 830                 835

gag aat ctg atg tgg aaa caa ata aca cca gaa ttg aat cac att cta      2658
Glu Asn Leu Met Trp Lys Gln Ile Thr Pro Glu Leu Asn His Ile Leu
    840                 845                 850

tca gaa aat gag gtg aag tta act att atg aca gga gac atc aaa gga      2706
Ser Glu Asn Glu Val Lys Leu Thr Ile Met Thr Gly Asp Ile Lys Gly
855                 860                 865                 870

atc atg cag gca gga aaa cga tct ctg cgg cct cag ccc act gag ctg      2754
Ile Met Gln Ala Gly Lys Arg Ser Leu Arg Pro Gln Pro Thr Glu Leu
                875                 880                 885

aag tat tca tgg aaa aca tgg ggc aaa gca aaa atg ctc tct aca gag      2802
Lys Tyr Ser Trp Lys Thr Trp Gly Lys Ala Lys Met Leu Ser Thr Glu
            890                 895                 900

tct cat aac cag acc ttt ctc att gat ggc ccc gaa aca gca gaa tgc      2850
Ser His Asn Gln Thr Phe Leu Ile Asp Gly Pro Glu Thr Ala Glu Cys
        905                 910                 915

ccc aac aca aat aga gct tgg aat tcg ttg gaa gtt gaa gac tat ggc      2898
Pro Asn Thr Asn Arg Ala Trp Asn Ser Leu Glu Val Glu Asp Tyr Gly
```

-continued

```
    920                 925                 930

ttt gga gta ttc acc acc aat ata tgg cta aaa ttg aaa gaa aaa cag     2946
Phe Gly Val Phe Thr Thr Asn Ile Trp Leu Lys Leu Lys Glu Lys Gln
935                 940                 945                 950

gat gta ttc tgc gac tca aaa ctc atg tca gcg gcc ata aaa gac aac     2994
Asp Val Phe Cys Asp Ser Lys Leu Met Ser Ala Ala Ile Lys Asp Asn
                955                 960                 965

aga gcc gtc cat gcc gat atg ggt tat tgg ata gaa agt gca ctc aat     3042
Arg Ala Val His Ala Asp Met Gly Tyr Trp Ile Glu Ser Ala Leu Asn
            970                 975                 980

gac aca tgg aag ata gag aaa gcc tct ttc att gaa gtt aaa aac tgc     3090
Asp Thr Trp Lys Ile Glu Lys Ala Ser Phe Ile Glu Val Lys Asn Cys
        985                 990                 995

cac tgg  cca aaa tca cac acc  ctc tgg agc aat gga  gtg cta gaa      3135
His Trp  Pro Lys Ser His Thr  Leu Trp Ser Asn Gly  Val Leu Glu
    1000                 1005                 1010

agt gag  atg ata att cca aag  aat ctc gct gga cca  gtg tct caa      3180
Ser Glu  Met Ile Ile Pro Lys  Asn Leu Ala Gly Pro  Val Ser Gln
    1015                 1020                 1025

cac aac  tat aga cca ggc tac  cat aca caa ata aca  gga cca tgg      3225
His Asn  Tyr Arg Pro Gly Tyr  His Thr Gln Ile Thr  Gly Pro Trp
    1030                 1035                 1040

cat cta  ggt aag ctt gag atg  gac ttt gat ttc tgt  gat gga aca      3270
His Leu  Gly Lys Leu Glu Met  Asp Phe Asp Phe Cys  Asp Gly Thr
    1045                 1050                 1055

aca gtg  gta gtg act gag gac  tgc gga aat aga gga  ccc tct ttg      3315
Thr Val  Val Val Thr Glu Asp  Cys Gly Asn Arg Gly  Pro Ser Leu
    1060                 1065                 1070

aga aca  acc act gcc tct gga  aaa ctc ata aca gaa  tgg tgc tgc      3360
Arg Thr  Thr Thr Ala Ser Gly  Lys Leu Ile Thr Glu  Trp Cys Cys
    1075                 1080                 1085

cga tct  tgc aca tta cca ccg  cta aga tac aga ggt  gag gat ggg      3405
Arg Ser  Cys Thr Leu Pro Pro  Leu Arg Tyr Arg Gly  Glu Asp Gly
    1090                 1095                 1100

tgc tgg  tac ggg atg gaa atc  aga cca ttg aag gag  aaa gaa gag      3450
Cys Trp  Tyr Gly Met Glu Ile  Arg Pro Leu Lys Glu  Lys Glu Glu
    1105                 1110                 1115

aat ttg  gtc aac tcc ttg gtc  aca gct gga cat ggg  cag gtc gac      3495
Asn Leu  Val Asn Ser Leu Val  Thr Ala Gly His Gly  Gln Val Asp
    1120                 1125                 1130

aac ttt  tca cta gga gtc ttg  gga atg gca ttg ttc  ctg gag gaa      3540
Asn Phe  Ser Leu Gly Val Leu  Gly Met Ala Leu Phe  Leu Glu Glu
    1135                 1140                 1145

atg ctt  agg acc cga gta gga  acg aaa cat gca ata  cta cta gtt      3585
Met Leu  Arg Thr Arg Val Gly  Thr Lys His Ala Ile  Leu Leu Val
    1150                 1155                 1160

gca gtt  tct ttt gtg aca ttg  atc aca ggg aac atg  tcc ttt aga      3630
Ala Val  Ser Phe Val Thr Leu  Ile Thr Gly Asn Met  Ser Phe Arg
    1165                 1170                 1175

gac ctg  gga aga gtg atg gtt  atg gta ggc gcc act  atg acg gat      3675
Asp Leu  Gly Arg Val Met Val  Met Val Gly Ala Thr  Met Thr Asp
    1180                 1185                 1190

gac ata  ggt atg ggc gtg act  tat ctt gcc cta cta  gca gcc ttc      3720
Asp Ile  Gly Met Gly Val Thr  Tyr Leu Ala Leu Leu  Ala Ala Phe
    1195                 1200                 1205

aaa gtc  aga cca act ttt gca  gct gga cta ctc ttg  aga aag ctg      3765
Lys Val  Arg Pro Thr Phe Ala  Ala Gly Leu Leu Leu  Arg Lys Leu
    1210                 1215                 1220

acc tcc  aag gaa ttg atg atg  act act ata gga att  gta ctc ctc      3810
```

-continued

```
Thr Ser  Lys Glu Leu Met Met  Thr Thr Ile Gly Ile  Val Leu Leu
    1225                 1230                 1235

tcc cag  agc acc ata cca gag  acc att ctt gag ttg  act gat gcg      3855
Ser Gln  Ser Thr Ile Pro Glu  Thr Ile Leu Glu Leu  Thr Asp Ala
    1240                 1245                 1250

tta gcc  tta ggc atg atg gtc  ctc aaa atg gtg aga  aat atg gaa      3900
Leu Ala  Leu Gly Met Met Val  Leu Lys Met Val Arg  Asn Met Glu
    1255                 1260                 1265

aag tat  caa ttg gca gtg act  atc atg gct atc ttg  tgc gtc cca      3945
Lys Tyr  Gln Leu Ala Val Thr  Ile Met Ala Ile Leu  Cys Val Pro
    1270                 1275                 1280

aac gca  gtg ata tta caa aac  gca tgg aaa gtg agt  tgc aca ata      3990
Asn Ala  Val Ile Leu Gln Asn  Ala Trp Lys Val Ser  Cys Thr Ile
    1285                 1290                 1295

ttg gca  gtg gtg tcc gtt tcc  cca ctg ttc tta aca  tcc tca cag      4035
Leu Ala  Val Val Ser Val Ser  Pro Leu Phe Leu Thr  Ser Ser Gln
    1300                 1305                 1310

caa aaa  aca gat tgg ata cca  tta gca ttg acg atc  aaa ggt ctc      4080
Gln Lys  Thr Asp Trp Ile Pro  Leu Ala Leu Thr Ile  Lys Gly Leu
    1315                 1320                 1325

aat cca  aca gct att ttt cta  aca acc ctc tca aga  acc agc aag      4125
Asn Pro  Thr Ala Ile Phe Leu  Thr Thr Leu Ser Arg  Thr Ser Lys
    1330                 1335                 1340

aaa agg  agc tgg cca tta aat  gag gct atc atg gca  gtc ggg atg      4170
Lys Arg  Ser Trp Pro Leu Asn  Glu Ala Ile Met Ala  Val Gly Met
    1345                 1350                 1355

gtg agc  att tta gcc agt tct  ctc cta aaa aat gat  att ccc atg      4215
Val Ser  Ile Leu Ala Ser Ser  Leu Leu Lys Asn Asp  Ile Pro Met
    1360                 1365                 1370

aca gga  cca tta gtg gct gga  ggg ctc ctc act gtg  tgc tac gtg      4260
Thr Gly  Pro Leu Val Ala Gly  Gly Leu Leu Thr Val  Cys Tyr Val
    1375                 1380                 1385

ctc act  gga cga tcg gcc gat  ttg gaa ctg gag aga  gca gcc gat      4305
Leu Thr  Gly Arg Ser Ala Asp  Leu Glu Leu Glu Arg  Ala Ala Asp
    1390                 1395                 1400

gtc aaa  tgg gaa gac cag gca  gag ata tca gga agc  agt cca atc      4350
Val Lys  Trp Glu Asp Gln Ala  Glu Ile Ser Gly Ser  Ser Pro Ile
    1405                 1410                 1415

ctg tca  ata aca ata tca gaa  gat ggt agc atg tcg  ata aaa aat      4395
Leu Ser  Ile Thr Ile Ser Glu  Asp Gly Ser Met Ser  Ile Lys Asn
    1420                 1425                 1430

gaa gag  gaa gaa caa aca ctg  acc ata ctc att aga  aca gga ttg      4440
Glu Glu  Glu Glu Gln Thr Leu  Thr Ile Leu Ile Arg  Thr Gly Leu
    1435                 1440                 1445

ctg gtg  atc tca gga ctt ttt  cct gta tca ata cca  atc acg gca      4485
Leu Val  Ile Ser Gly Leu Phe  Pro Val Ser Ile Pro  Ile Thr Ala
    1450                 1455                 1460

gca gca  tgg tac ctg tgg gaa  gtg aag aaa caa cgg  gcc gga gta      4530
Ala Ala  Trp Tyr Leu Trp Glu  Val Lys Lys Gln Arg  Ala Gly Val
    1465                 1470                 1475

ttg tgg  gat gtt cct tca ccc  cca ccc atg gga aag  gct gaa ctg      4575
Leu Trp  Asp Val Pro Ser Pro  Pro Pro Met Gly Lys  Ala Glu Leu
    1480                 1485                 1490

gaa gat  gga gcc tat aga att  aag caa aaa ggg att  ctt gga tat      4620
Glu Asp  Gly Ala Tyr Arg Ile  Lys Gln Lys Gly Ile  Leu Gly Tyr
    1495                 1500                 1505

tcc cag  atc gga gcc gga gtt  tac aaa gaa gga aca  ttc cat aca      4665
Ser Gln  Ile Gly Ala Gly Val  Tyr Lys Glu Gly Thr  Phe His Thr
    1510                 1515                 1520
```

-continued

```
atg tgg  cat gtc aca cgt ggc  gct gtt cta atg cat  aaa gga aag      4710
Met Trp  His Val Thr Arg Gly  Ala Val Leu Met His  Lys Gly Lys
    1525                 1530                 1535

agg att  gaa cca aca tgg gcg  gac gtc aag aaa gac  cta ata tca      4755
Arg Ile  Glu Pro Thr Trp Ala  Asp Val Lys Lys Asp  Leu Ile Ser
    1540                 1545                 1550

tat gga  gga ggc tgg aag tta  gaa gga gaa tgg aag  gaa gga gaa      4800
Tyr Gly  Gly Gly Trp Lys Leu  Glu Gly Glu Trp Lys  Glu Gly Glu
    1555                 1560                 1565

gaa gtc  cag gta ttg gca ctg  gag cct gga aaa aat  cca aga gcc      4845
Glu Val  Gln Val Leu Ala Leu  Glu Pro Gly Lys Asn  Pro Arg Ala
    1570                 1575                 1580

gtc caa  acg aaa cct ggt ctt  ttc aaa acc aac gcc  gga aca ata      4890
Val Gln  Thr Lys Pro Gly Leu  Phe Lys Thr Asn Ala  Gly Thr Ile
    1585                 1590                 1595

ggt gct  gta tct ctg gac ttt  tct cct gga acg tca  gga tct cca      4935
Gly Ala  Val Ser Leu Asp Phe  Ser Pro Gly Thr Ser  Gly Ser Pro
    1600                 1605                 1610

att atc  gac aaa aaa gga aaa  gtt gtg ggt ctt tat  ggt aat ggt      4980
Ile Ile  Asp Lys Lys Gly Lys  Val Val Gly Leu Tyr  Gly Asn Gly
    1615                 1620                 1625

gtt gtt  aca agg agt gga gca  tat gtg agt gct ata  gcc cag act      5025
Val Val  Thr Arg Ser Gly Ala  Tyr Val Ser Ala Ile  Ala Gln Thr
    1630                 1635                 1640

gaa aaa  agc att gaa gac aac  cca gag atc gaa gat  cac att ttc      5070
Glu Lys  Ser Ile Glu Asp Asn  Pro Glu Ile Glu Asp  His Ile Phe
    1645                 1650                 1655

cga aag  aga aga ctg acc atc  atg gac ctc cac cca  gga gcg gga      5115
Arg Lys  Arg Arg Leu Thr Ile  Met Asp Leu His Pro  Gly Ala Gly
    1660                 1665                 1670

aag acg  aag aga tac ctt ccg  gcc ata gtc aga gaa  gct ata aaa      5160
Lys Thr  Lys Arg Tyr Leu Pro  Ala Ile Val Arg Glu  Ala Ile Lys
    1675                 1680                 1685

cgg ggt  ttg aga aca tta atc  ttg gcc ccc act aga  gtt gtg gca      5205
Arg Gly  Leu Arg Thr Leu Ile  Leu Ala Pro Thr Arg  Val Val Ala
    1690                 1695                 1700

gct gaa  atg gag gaa gcc ctt  aga gga ctt cca ata  aga tac cag      5250
Ala Glu  Met Glu Glu Ala Leu  Arg Gly Leu Pro Ile  Arg Tyr Gln
    1705                 1710                 1715

acc cca  gcc atc aga gct gag  cac acc ggg cgg gag  att gtg gac      5295
Thr Pro  Ala Ile Arg Ala Glu  His Thr Gly Arg Glu  Ile Val Asp
    1720                 1725                 1730

cta atg  tgt cat gcc aca ttt  acc atg agg ctg cta  tca cca gtt      5340
Leu Met  Cys His Ala Thr Phe  Thr Met Arg Leu Leu  Ser Pro Val
    1735                 1740                 1745

aga gtg  cca aac tac aac ctg  att atc atg gac gaa  gcc cat ttc      5385
Arg Val  Pro Asn Tyr Asn Leu  Ile Ile Met Asp Glu  Ala His Phe
    1750                 1755                 1760

aca gac  cca gca agt ata gca  gct aga gga tac atc  tca act cga      5430
Thr Asp  Pro Ala Ser Ile Ala  Ala Arg Gly Tyr Ile  Ser Thr Arg
    1765                 1770                 1775

gtg gag  atg ggt gag gca gct  ggg att ttt atg aca  gcc act ccc      5475
Val Glu  Met Gly Glu Ala Ala  Gly Ile Phe Met Thr  Ala Thr Pro
    1780                 1785                 1790

ccg gga  agc aga gac cca ttt  cct cag agc aat gca  cca atc ata      5520
Pro Gly  Ser Arg Asp Pro Phe  Pro Gln Ser Asn Ala  Pro Ile Ile
    1795                 1800                 1805

gat gaa  gaa aga gaa atc cct  gaa cgc tcg tgg aat  tcc gga cat      5565
Asp Glu  Glu Arg Glu Ile Pro  Glu Arg Ser Trp Asn  Ser Gly His
    1810                 1815                 1820
```

-continued

```
gaa tgg gtc acg gat ttt aaa ggg aag act gtt tgg ttc gtt cca      5610
Glu Trp Val Thr Asp Phe Lys Gly Lys Thr Val Trp Phe Val Pro
    1825                1830                1835

agt ata aaa gca gga aat gat ata gca gct tgc ctg agg aaa aat      5655
Ser Ile Lys Ala Gly Asn Asp Ile Ala Ala Cys Leu Arg Lys Asn
    1840                1845                1850

gga aag aaa gtg ata caa ctc agt agg aag acc ttt gat tct gag      5700
Gly Lys Lys Val Ile Gln Leu Ser Arg Lys Thr Phe Asp Ser Glu
    1855                1860                1865

tat gtc aag act aga acc aat gat tgg gac ttc gtg gtt aca act      5745
Tyr Val Lys Thr Arg Thr Asn Asp Trp Asp Phe Val Val Thr Thr
    1870                1875                1880

gac att tca gaa atg ggt gcc aat ttc aag gct gag agg gtt ata      5790
Asp Ile Ser Glu Met Gly Ala Asn Phe Lys Ala Glu Arg Val Ile
    1885                1890                1895

gac ccc aga cgc tgc atg aaa cca gtc ata cta aca gat ggt gaa      5835
Asp Pro Arg Arg Cys Met Lys Pro Val Ile Leu Thr Asp Gly Glu
    1900                1905                1910

gag cgg gtg att ctg gca gga cct atg cca gtg acc cac tct agt      5880
Glu Arg Val Ile Leu Ala Gly Pro Met Pro Val Thr His Ser Ser
    1915                1920                1925

gca gca caa aga aga ggg aga ata gga aga aat cca aaa aat gag      5925
Ala Ala Gln Arg Arg Gly Arg Ile Gly Arg Asn Pro Lys Asn Glu
    1930                1935                1940

aat gac cag tac ata tac atg ggg gaa cct ctg gaa aat gat gaa      5970
Asn Asp Gln Tyr Ile Tyr Met Gly Glu Pro Leu Glu Asn Asp Glu
    1945                1950                1955

gac tgt gca cac tgg aaa gaa gct aaa atg ctc cta gat aac atc      6015
Asp Cys Ala His Trp Lys Glu Ala Lys Met Leu Leu Asp Asn Ile
    1960                1965                1970

aac acg cca gaa gga atc att cct agc atg ttc gaa cca gag cgt      6060
Asn Thr Pro Glu Gly Ile Ile Pro Ser Met Phe Glu Pro Glu Arg
    1975                1980                1985

gaa aag gtg gat gcc att gat ggc gaa tac cgc ttg aga gga gaa      6105
Glu Lys Val Asp Ala Ile Asp Gly Glu Tyr Arg Leu Arg Gly Glu
    1990                1995                2000

gca agg aaa acc ttt gta gac tta atg aga aga gga gac cta cca      6150
Ala Arg Lys Thr Phe Val Asp Leu Met Arg Arg Gly Asp Leu Pro
    2005                2010                2015

gtc tgg ttg gcc tac aga gtg gca gct gaa ggc atc aac tac gca      6195
Val Trp Leu Ala Tyr Arg Val Ala Ala Glu Gly Ile Asn Tyr Ala
    2020                2025                2030

gac aga agg tgg tgt ttt gat gga gtc aag aac aac caa atc cta      6240
Asp Arg Arg Trp Cys Phe Asp Gly Val Lys Asn Asn Gln Ile Leu
    2035                2040                2045

gaa gaa aac gtg gaa gtt gaa atc tgg aca aaa gaa ggg gaa agg      6285
Glu Glu Asn Val Glu Val Glu Ile Trp Thr Lys Glu Gly Glu Arg
    2050                2055                2060

aag aaa ttg aaa ccc aga tgg ttg gat gct agg atc tat tct gac      6330
Lys Lys Leu Lys Pro Arg Trp Leu Asp Ala Arg Ile Tyr Ser Asp
    2065                2070                2075

cca ctg gcg cta aaa gaa ttt aag gaa ttt gca gcc gga aga aag      6375
Pro Leu Ala Leu Lys Glu Phe Lys Glu Phe Ala Ala Gly Arg Lys
    2080                2085                2090

tct ctg acc ctg aac cta atc aca gaa atg ggt agg ctc cca acc      6420
Ser Leu Thr Leu Asn Leu Ile Thr Glu Met Gly Arg Leu Pro Thr
    2095                2100                2105

ttc atg act cag aag gca aga gac gca ctg gac aac tta gca gtg      6465
Phe Met Thr Gln Lys Ala Arg Asp Ala Leu Asp Asn Leu Ala Val
```

-continued

```
    2110                2115                2120

ctg cac  acg gct gag gca ggt  gga agg gcg tac aac  cat gct ctc      6510
Leu His  Thr Ala Glu Ala Gly  Gly Arg Ala Tyr Asn  His Ala Leu
    2125                2130                2135

agt gaa  ctg ccg gag acc ctg  gag aca ttg ctt tta  ctg aca ctt      6555
Ser Glu  Leu Pro Glu Thr Leu  Glu Thr Leu Leu Leu  Leu Thr Leu
    2140                2145                2150

ctg gct  aca gtc acg gga ggg  atc ttt tta ttc ttg  atg agc gca      6600
Leu Ala  Thr Val Thr Gly Gly  Ile Phe Leu Phe Leu  Met Ser Ala
    2155                2160                2165

agg ggc  ata ggg aag atg acc  ctg gga atg tgc tgc  ata atc acg      6645
Arg Gly  Ile Gly Lys Met Thr  Leu Gly Met Cys Cys  Ile Ile Thr
    2170                2175                2180

gct agc  atc ctc cta tgg tac  gca caa ata cag cca  cac tgg ata      6690
Ala Ser  Ile Leu Leu Trp Tyr  Ala Gln Ile Gln Pro  His Trp Ile
    2185                2190                2195

gca gct  tca ata ata ctg gag  ttt ttt ctc ata gtt  ttg ctt att      6735
Ala Ala  Ser Ile Ile Leu Glu  Phe Phe Leu Ile Val  Leu Leu Ile
    2200                2205                2210

cca gaa  cct gaa aaa cag aga  aca ccc caa gac aac  caa ctg acc      6780
Pro Glu  Pro Glu Lys Gln Arg  Thr Pro Gln Asp Asn  Gln Leu Thr
    2215                2220                2225

tac gtt  gtc ata gcc atc ctc  aca gtg gtg gcc gca  acc atg gca      6825
Tyr Val  Val Ile Ala Ile Leu  Thr Val Val Ala Ala  Thr Met Ala
    2230                2235                2240

aac gag  atg ggt ttc cta gaa  aaa acg aag aaa gat  ctc gga ttg      6870
Asn Glu  Met Gly Phe Leu Glu  Lys Thr Lys Lys Asp  Leu Gly Leu
    2245                2250                2255

gga agc  att gca acc cag caa  ccc gag agc aac atc  ctg gac ata      6915
Gly Ser  Ile Ala Thr Gln Gln  Pro Glu Ser Asn Ile  Leu Asp Ile
    2260                2265                2270

gat cta  cgt cct gca tca gca  tgg acg ctg tat gcc  gtg gcc aca      6960
Asp Leu  Arg Pro Ala Ser Ala  Trp Thr Leu Tyr Ala  Val Ala Thr
    2275                2280                2285

aca ttt  gtt aca cca atg ttg  aga cat agc att gaa  aat tcc tca      7005
Thr Phe  Val Thr Pro Met Leu  Arg His Ser Ile Glu  Asn Ser Ser
    2290                2295                2300

gtg aat  gtg tcc cta aca gct  ata gcc aac caa gcc  aca gtg tta      7050
Val Asn  Val Ser Leu Thr Ala  Ile Ala Asn Gln Ala  Thr Val Leu
    2305                2310                2315

atg ggt  ctc ggg aaa gga tgg  cca ttg tca aag atg  gac atc gga      7095
Met Gly  Leu Gly Lys Gly Trp  Pro Leu Ser Lys Met  Asp Ile Gly
    2320                2325                2330

gtt ccc  ctt ctc gcc att gga  tgc tac tca caa gtc  aac ccc ata      7140
Val Pro  Leu Leu Ala Ile Gly  Cys Tyr Ser Gln Val  Asn Pro Ile
    2335                2340                2345

act ctc  aca gca gct ctt ttc  tta ttg gta gca cat  tat gcc atc      7185
Thr Leu  Thr Ala Ala Leu Phe  Leu Leu Val Ala His  Tyr Ala Ile
    2350                2355                2360

ata ggg  cca gga ctc caa gca  aaa gca acc aga gaa  gct cag aaa      7230
Ile Gly  Pro Gly Leu Gln Ala  Lys Ala Thr Arg Glu  Ala Gln Lys
    2365                2370                2375

aga gca  gcg gcg ggc atc atg  aaa aac cca act gtc  gat gga ata      7275
Arg Ala  Ala Ala Gly Ile Met  Lys Asn Pro Thr Val  Asp Gly Ile
    2380                2385                2390

aca gtg  att gac cta gat cca  ata cct tat gat cca  aag ttt gaa      7320
Thr Val  Ile Asp Leu Asp Pro  Ile Pro Tyr Asp Pro  Lys Phe Glu
    2395                2400                2405

aag cag  ttg gga caa gta atg  ctc cta gtc ctc tgc  gtg act caa      7365
```

-continued

```
Lys Gln Leu Gly Gln Val Met Leu Leu Val Leu Cys Val Thr Gln
    2410                2415                2420

gta ttg atg atg agg act aca tgg gct ctg tgt gag gct tta acc      7410
Val Leu Met Met Arg Thr Thr Trp Ala Leu Cys Glu Ala Leu Thr
    2425                2430                2435

tta gct acc ggg ccc atc tcc aca ttg tgg gaa gga aat cca ggg      7455
Leu Ala Thr Gly Pro Ile Ser Thr Leu Trp Glu Gly Asn Pro Gly
    2440                2445                2450

agg ttt tgg aac act acc att gcg gtg tca atg gct aac att ttt      7500
Arg Phe Trp Asn Thr Thr Ile Ala Val Ser Met Ala Asn Ile Phe
    2455                2460                2465

aga ggg agt tac ttg gcc gga gct gga ctt ctc ttt tct att atg      7545
Arg Gly Ser Tyr Leu Ala Gly Ala Gly Leu Leu Phe Ser Ile Met
    2470                2475                2480

aag aac aca acc aac aca aga agg gga act ggc aac ata gga gag      7590
Lys Asn Thr Thr Asn Thr Arg Arg Gly Thr Gly Asn Ile Gly Glu
    2485                2490                2495

acg ctt gga gag aaa tgg aaa agc cga ttg aac gca ttg gga aaa      7635
Thr Leu Gly Glu Lys Trp Lys Ser Arg Leu Asn Ala Leu Gly Lys
    2500                2505                2510

agt gaa ttc cag atc tac aag aaa agt gga atc cag gaa gtg gat      7680
Ser Glu Phe Gln Ile Tyr Lys Lys Ser Gly Ile Gln Glu Val Asp
    2515                2520                2525

aga acc tta gca aaa gaa ggc att aaa aga gga gaa acg gac cat      7725
Arg Thr Leu Ala Lys Glu Gly Ile Lys Arg Gly Glu Thr Asp His
    2530                2535                2540

cac gct gtg tcg cga ggc tca gca aaa ctg aga tgg ttc gtt gag      7770
His Ala Val Ser Arg Gly Ser Ala Lys Leu Arg Trp Phe Val Glu
    2545                2550                2555

aga aac atg gtc aca cca gaa ggg aaa gta gtg gac ctc ggt tgt      7815
Arg Asn Met Val Thr Pro Glu Gly Lys Val Val Asp Leu Gly Cys
    2560                2565                2570

ggc aga gga ggc tgg tca tac tat tgt gga gga cta aag aat gta      7860
Gly Arg Gly Gly Trp Ser Tyr Tyr Cys Gly Gly Leu Lys Asn Val
    2575                2580                2585

aga gaa gtc aaa ggc cta aca aaa gga gga cca gga cac gaa gaa      7905
Arg Glu Val Lys Gly Leu Thr Lys Gly Gly Pro Gly His Glu Glu
    2590                2595                2600

ccc atc ccc atg tca aca tat ggg tgg aat cta gtg cgt ctt caa      7950
Pro Ile Pro Met Ser Thr Tyr Gly Trp Asn Leu Val Arg Leu Gln
    2605                2610                2615

agt gga gtt gac gtt ttc ttc atc ccg cca gaa aag tgt gac aca      7995
Ser Gly Val Asp Val Phe Phe Ile Pro Pro Glu Lys Cys Asp Thr
    2620                2625                2630

tta ttg tgt gac ata ggg gag tca tca cca aat ccc aca gtg gaa      8040
Leu Leu Cys Asp Ile Gly Glu Ser Ser Pro Asn Pro Thr Val Glu
    2635                2640                2645

gca gga cga aca ctc aga gtc ctt aac tta gta gaa aat tgg ttg      8085
Ala Gly Arg Thr Leu Arg Val Leu Asn Leu Val Glu Asn Trp Leu
    2650                2655                2660

aac aac aac act caa ttt tgc ata aag gtt ctc aac cca tat atg      8130
Asn Asn Asn Thr Gln Phe Cys Ile Lys Val Leu Asn Pro Tyr Met
    2665                2670                2675

ccc tca gtc ata gaa aaa atg gaa gca cta caa agg aaa tat gga      8175
Pro Ser Val Ile Glu Lys Met Glu Ala Leu Gln Arg Lys Tyr Gly
    2680                2685                2690

gga gcc tta gtg agg aat cca ctc tca cga aac tcc aca cat gag      8220
Gly Ala Leu Val Arg Asn Pro Leu Ser Arg Asn Ser Thr His Glu
    2695                2700                2705
```

-continued

```
atg tac  tgg gta tcc aat gct  tcc ggg aac ata gtg  tca tca gtg      8265
Met Tyr  Trp Val Ser Asn Ala  Ser Gly Asn Ile Val  Ser Ser Val
    2710                2715                 2720

aac atg  att tca agg atg ttg  atc aac aga ttt aca  atg aga tac      8310
Asn Met  Ile Ser Arg Met Leu  Ile Asn Arg Phe Thr  Met Arg Tyr
    2725                2730                 2735

aag aaa  gcc act tac gag ccg  gat gtt gac ctc gga  agc gga acc      8355
Lys Lys  Ala Thr Tyr Glu Pro  Asp Val Asp Leu Gly  Ser Gly Thr
    2740                2745                 2750

cgt aac  atc ggg att gaa agt  gag ata cca aac cta  gat ata att      8400
Arg Asn  Ile Gly Ile Glu Ser  Glu Ile Pro Asn Leu  Asp Ile Ile
    2755                2760                 2765

ggg aaa  aga ata gaa aaa ata  aag caa gag cat gaa  aca tca tgg      8445
Gly Lys  Arg Ile Glu Lys Ile  Lys Gln Glu His Glu  Thr Ser Trp
    2770                2775                 2780

cac tat  gac caa gac cac cca  tac aaa acg tgg gca  tac cat ggt      8490
His Tyr  Asp Gln Asp His Pro  Tyr Lys Thr Trp Ala  Tyr His Gly
    2785                2790                 2795

agc tat  gaa aca aaa cag act  gga tca gca tca tcc  atg gtc aac      8535
Ser Tyr  Glu Thr Lys Gln Thr  Gly Ser Ala Ser Ser  Met Val Asn
    2800                2805                 2810

gga gtg  gtc agg ctg ctg aca  aaa cct tgg gac gtt  gtc ccc atg      8580
Gly Val  Val Arg Leu Leu Thr  Lys Pro Trp Asp Val  Val Pro Met
    2815                2820                 2825

gtg aca  cag atg gca atg aca  gac acg act cca ttt  gga caa cag      8625
Val Thr  Gln Met Ala Met Thr  Asp Thr Thr Pro Phe  Gly Gln Gln
    2830                2835                 2840

cgc gtt  ttt aaa gag aaa gtg  gac acg aga acc caa  gaa ccg aaa      8670
Arg Val  Phe Lys Glu Lys Val  Asp Thr Arg Thr Gln  Glu Pro Lys
    2845                2850                 2855

gaa ggc  acg aag aaa cta atg  aaa ata aca gca gag  tgg ctt tgg      8715
Glu Gly  Thr Lys Lys Leu Met  Lys Ile Thr Ala Glu  Trp Leu Trp
    2860                2865                 2870

aaa gaa  tta ggg aag aaa aag  aca ccc agg atg tgc  acc aga gaa      8760
Lys Glu  Leu Gly Lys Lys Lys  Thr Pro Arg Met Cys  Thr Arg Glu
    2875                2880                 2885

gaa ttc  aca aga aag gtg aga  agc aat gca gcc ttg  ggg gcc ata      8805
Glu Phe  Thr Arg Lys Val Arg  Ser Asn Ala Ala Leu  Gly Ala Ile
    2890                2895                 2900

ttc act  gat gag aac aag tgg  aag tcg gca cgt gag  gct gtt gaa      8850
Phe Thr  Asp Glu Asn Lys Trp  Lys Ser Ala Arg Glu  Ala Val Glu
    2905                2910                 2915

gat agt  agg ttt tgg gag ctg  gtt gac aag gaa agg  aat ctc cat      8895
Asp Ser  Arg Phe Trp Glu Leu  Val Asp Lys Glu Arg  Asn Leu His
    2920                2925                 2930

ctt gaa  gga aag tgt gaa aca  tgt gtg tac aac atg  atg gga aaa      8940
Leu Glu  Gly Lys Cys Glu Thr  Cys Val Tyr Asn Met  Met Gly Lys
    2935                2940                 2945

aga gag  aag aag cta ggg gaa  ttc ggc aag gca aaa  ggc agc aga      8985
Arg Glu  Lys Lys Leu Gly Glu  Phe Gly Lys Ala Lys  Gly Ser Arg
    2950                2955                 2960

gcc ata  tgg tac atg tgg ctt  gga gca cgc ttc tta  gag ttt gaa      9030
Ala Ile  Trp Tyr Met Trp Leu  Gly Ala Arg Phe Leu  Glu Phe Glu
    2965                2970                 2975

gcc cta  gga ttc tta aat gaa  gat cac tgg ttc tcc  aga gag aac      9075
Ala Leu  Gly Phe Leu Asn Glu  Asp His Trp Phe Ser  Arg Glu Asn
    2980                2985                 2990

tcc ctg  agt gga gtg gaa gga  gaa ggg ctg cac aag  cta ggt tac      9120
Ser Leu  Ser Gly Val Glu Gly  Glu Gly Leu His Lys  Leu Gly Tyr
    2995                3000                 3005
```

-continued

```
att cta  aga gac gtg agc aag  aaa gag gga gga gca  atg tat gcc      9165
Ile Leu  Arg Asp Val Ser Lys  Lys Glu Gly Gly Ala  Met Tyr Ala
    3010                 3015                 3020

gat gac  acc gca gga tgg gat  aca aaa atc aca cta  gaa gac cta      9210
Asp Asp  Thr Ala Gly Trp Asp  Thr Lys Ile Thr Leu  Glu Asp Leu
    3025                 3030                 3035

aaa aat  gaa gag atg gta aca  aac cac atg gaa gga  gaa cac aag      9255
Lys Asn  Glu Glu Met Val Thr  Asn His Met Glu Gly  Glu His Lys
    3040                 3045                 3050

aaa cta  gcc gag gcc att ttc  aaa cta acg tac caa  aac aag gtg      9300
Lys Leu  Ala Glu Ala Ile Phe  Lys Leu Thr Tyr Gln  Asn Lys Val
    3055                 3060                 3065

gtg cgt  gtg caa aga cca aca  cca aga ggc aca gta  atg gac atc      9345
Val Arg  Val Gln Arg Pro Thr  Pro Arg Gly Thr Val  Met Asp Ile
    3070                 3075                 3080

ata tcg  aga aga gac caa aga  ggt agt gga caa gtt  ggc acc tat      9390
Ile Ser  Arg Arg Asp Gln Arg  Gly Ser Gly Gln Val  Gly Thr Tyr
    3085                 3090                 3095

gga ctc  aat act ttc acc aat  atg gaa gcc caa cta  atc aga cag      9435
Gly Leu  Asn Thr Phe Thr Asn  Met Glu Ala Gln Leu  Ile Arg Gln
    3100                 3105                 3110

atg gag  gga gaa gga gtc ttt  aaa agc att cag cac  cta aca atc      9480
Met Glu  Gly Glu Gly Val Phe  Lys Ser Ile Gln His  Leu Thr Ile
    3115                 3120                 3125

aca gaa  gaa atc gct gtg caa  aac tgg tta gca aga  gtg ggg cgc      9525
Thr Glu  Glu Ile Ala Val Gln  Asn Trp Leu Ala Arg  Val Gly Arg
    3130                 3135                 3140

gaa agg  tta tca aga atg gcc  atc agt gga gat gat  tgt gtt gtg      9570
Glu Arg  Leu Ser Arg Met Ala  Ile Ser Gly Asp Asp  Cys Val Val
    3145                 3150                 3155

aaa cct  tta gat gac agg ttc  gca agc gct tta aca  gct cta aat      9615
Lys Pro  Leu Asp Asp Arg Phe  Ala Ser Ala Leu Thr  Ala Leu Asn
    3160                 3165                 3170

gac atg  gga aag att agg aaa  gac ata caa caa tgg  gaa cct tca      9660
Asp Met  Gly Lys Ile Arg Lys  Asp Ile Gln Gln Trp  Glu Pro Ser
    3175                 3180                 3185

aga gga  tgg aat gat tgg aca  caa gtg ccc ttc tgt  tca cac cat      9705
Arg Gly  Trp Asn Asp Trp Thr  Gln Val Pro Phe Cys  Ser His His
    3190                 3195                 3200

ttc cat  gag tta atc atg aaa  gac ggt cgc gta ctc  gtt gtt cca      9750
Phe His  Glu Leu Ile Met Lys  Asp Gly Arg Val Leu  Val Val Pro
    3205                 3210                 3215

tgt aga  aac caa gat gaa ctg  att ggc aga gcc cga  atc tcc caa      9795
Cys Arg  Asn Gln Asp Glu Leu  Ile Gly Arg Ala Arg  Ile Ser Gln
    3220                 3225                 3230

gga gca  ggg tgg tct ttg cgg  gag acg gcc tgt ttg  ggg aag tct      9840
Gly Ala  Gly Trp Ser Leu Arg  Glu Thr Ala Cys Leu  Gly Lys Ser
    3235                 3240                 3245

tac gcc  caa atg tgg agc ttg  atg tac ttc cac aga  cgc gac ctc      9885
Tyr Ala  Gln Met Trp Ser Leu  Met Tyr Phe His Arg  Arg Asp Leu
    3250                 3255                 3260

agg ctg  gcg gca aat gct att  tgc tcg gca gta cca  tca cat tgg      9930
Arg Leu  Ala Ala Asn Ala Ile  Cys Ser Ala Val Pro  Ser His Trp
    3265                 3270                 3275

gtt cca  aca agt cga aca acc  tgg tcc ata cat gct  aaa cat gaa      9975
Val Pro  Thr Ser Arg Thr Thr  Trp Ser Ile His Ala  Lys His Glu
    3280                 3285                 3290

tgg atg  aca acg gaa gac atg  ctg aca gtc tgg aac  agg gtg tgg     10020
Trp Met  Thr Thr Glu Asp Met  Leu Thr Val Trp Asn  Arg Val Trp
```

-continued

```
    3295                3300                3305

att caa  gaa aac cca tgg atg  gaa gac aaa act cca  gtg gaa aca     10065
Ile Gln  Glu Asn Pro Trp Met  Glu Asp Lys Thr Pro  Val Glu Thr
    3310                3315                3320

tgg gag  gaa atc cca tac ttg  ggg aaa aga gaa gac  caa tgg tgc     10110
Trp Glu  Glu Ile Pro Tyr Leu  Gly Lys Arg Glu Asp  Gln Trp Cys
    3325                3330                3335

ggc tca  ttg att ggg tta aca  agc agg gcc acc tgg  gca aag aac     10155
Gly Ser  Leu Ile Gly Leu Thr  Ser Arg Ala Thr Trp  Ala Lys Asn
    3340                3345                3350

atc caa  gca gca ata aat caa  gtt aga tcc ctt ata  ggc aat gaa     10200
Ile Gln  Ala Ala Ile Asn Gln  Val Arg Ser Leu Ile  Gly Asn Glu
    3355                3360                3365

gaa tac  aca gat tac atg cca  tcc atg aaa aga ttc  aga aga gaa     10245
Glu Tyr  Thr Asp Tyr Met Pro  Ser Met Lys Arg Phe  Arg Arg Glu
    3370                3375                3380

gag gaa  gaa gca gga gtt ctg  tgg tag aaagcaaaac taacatgaaa       10292
Glu Glu  Glu Ala Gly Val Leu  Trp
    3385                3390

caaggctaga agtcaggtcg gattaagcca tagtacggaa aaaactatgc tacctgtgag  10352

ccccgtccaa ggacgttaaa agaagtcagg ccatcataaa tgccatagct tgagtaaact  10412

atgcagcctg tagctccacc tgagaaggtg taaaaaatcc gggaggccac aaaccatgga  10472

agctgtacgc atggcgtagt ggactagcgg ttaggggaga cccctccctt acaaatcgca  10532

gcaacaatgg gggcccaagg cgagatgaag ctgtagtctc gctggaagga ctagaggtta  10592

gaggagaccc ccccgaaaca aaaaacagca tattgacgct gggaaagacc agagatcctg  10652

ctgtctcctc agcatcattc caggcacaga acgccagaaa atggaatggt gctgttgaat  10712

caacaggttc t                                                       10723


<210> SEQ ID NO 2
<211> LENGTH: 3391
<212> TYPE: PRT
<213> ORGANISM: Dengue virus

<400> SEQUENCE: 2

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160
```

-continued

```
Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Arg Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Glu Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575
```

-continued

```
Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
```

-continued

```
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395
```

-continued

```
Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Thr Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  His Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Glu  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785
```

-continued

```
Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
```

-continued

```
    2180                2185                2190

Gln Pro His Trp Ile Ala Ala Ser Ile Ile Leu Glu Phe Phe Leu
    2195                2200                2205

Ile Val Leu Leu Ile Pro Glu Pro Glu Lys Gln Arg Thr Pro Gln
    2210                2215                2220

Asp Asn Gln Leu Thr Tyr Val Val Ile Ala Ile Leu Thr Val Val
    2225                2230                2235

Ala Ala Thr Met Ala Asn Glu Met Gly Phe Leu Glu Lys Thr Lys
    2240                2245                2250

Lys Asp Leu Gly Leu Gly Ser Ile Ala Thr Gln Gln Pro Glu Ser
    2255                2260                2265

Asn Ile Leu Asp Ile Asp Leu Arg Pro Ala Ser Ala Trp Thr Leu
    2270                2275                2280

Tyr Ala Val Ala Thr Thr Phe Val Thr Pro Met Leu Arg His Ser
    2285                2290                2295

Ile Glu Asn Ser Ser Val Asn Val Ser Leu Thr Ala Ile Ala Asn
    2300                2305                2310

Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
    2330                2335                2340

Gln Val Asn Pro Ile Thr Leu Thr Ala Ala Leu Phe Leu Leu Val
    2345                2350                2355

Ala His Tyr Ala Ile Ile Gly Pro Gly Leu Gln Ala Lys Ala Thr
    2360                2365                2370

Arg Glu Ala Gln Lys Arg Ala Ala Ala Gly Ile Met Lys Asn Pro
    2375                2380                2385

Thr Val Asp Gly Ile Thr Val Ile Asp Leu Asp Pro Ile Pro Tyr
    2390                2395                2400

Asp Pro Lys Phe Glu Lys Gln Leu Gly Gln Val Met Leu Leu Val
    2405                2410                2415

Leu Cys Val Thr Gln Val Leu Met Met Arg Thr Thr Trp Ala Leu
    2420                2425                2430

Cys Glu Ala Leu Thr Leu Ala Thr Gly Pro Ile Ser Thr Leu Trp
    2435                2440                2445

Glu Gly Asn Pro Gly Arg Phe Trp Asn Thr Thr Ile Ala Val Ser
    2450                2455                2460

Met Ala Asn Ile Phe Arg Gly Ser Tyr Leu Ala Gly Ala Gly Leu
    2465                2470                2475

Leu Phe Ser Ile Met Lys Asn Thr Thr Asn Thr Arg Arg Gly Thr
    2480                2485                2490

Gly Asn Ile Gly Glu Thr Leu Gly Glu Lys Trp Lys Ser Arg Leu
    2495                2500                2505

Asn Ala Leu Gly Lys Ser Glu Phe Gln Ile Tyr Lys Lys Ser Gly
    2510                2515                2520

Ile Gln Glu Val Asp Arg Thr Leu Ala Lys Glu Gly Ile Lys Arg
    2525                2530                2535

Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580
```

-continued

```
Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
    2885                 2890                 2895

Ala Leu  Gly Ala Ile Phe Thr  Asp Glu Asn Lys Trp  Lys Ser Ala
    2900                 2905                 2910

Arg Glu  Ala Val Glu Asp Ser  Arg Phe Trp Glu Leu  Val Asp Lys
    2915                 2920                 2925

Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970
```

-continued

```
Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Lys Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Thr Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
```

-continued 3365 3370 3375

Arg Phe Arg Arg Glu Glu Glu Glu Ala Gly Val Leu Trp
3380 3385 3390

<210> SEQ ID NO 3
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: Wild-type DEN2 strain 16681

<400> SEQUENCE: 3
agttgttagt ctacgtggac cgacaaagac agattctttg agggagctaa gctcaacgta 60
gttctaacag tttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggatggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgggaat gggactggag acacgaactg aaacatggat gtcatcagaa 780
ggggcctgga aacatgtcca gagaattgaa acttggatct tgagacatcc aggcttcacc 840
atgatggcag caatcctggc atacaccata ggaacgacac atttccaaag agccctgatt 900
ttcatcttac tgacagctgt cactccttca atgacaatgc gttgcatagg aatgtcaaat 960
agagactttg tggaaggggt ttcaggagga agctgggttg acatagtctt agaacatgga 1020
agctgtgtga cgacgatggc aaaaaacaaa ccaacattgg attttgaact gataaaaaca 1080
gaagccaaac agcctgccac cctaaggaag tactgtatag aggcaaagct aaccaacaca 1140
acaacagaat ctcgctgccc aacacaaggg gaacccagcc taaatgaaga gcaggacaaa 1200
aggttcgtct gcaaacactc catggtagac agaggatggg gaaatggatg tggactattt 1260
ggaaagggag gcattgtgac ctgtgctatg ttcagatgca aaaagaacat ggaaggaaaa 1320
gttgtgcaac cagaaaactt ggaatacacc attgtgataa cacctcactc aggggaagag 1380
catgcagtcg gaaatgacac aggaaaacat ggcaaggaaa tcaaaataac accacagagt 1440
tccatcacag aagcagaatt gacaggttat ggcactgtca caatggagtg ctctccaaga 1500
acgggcctcg acttcaatga gatggtgttg ctgcagatgg aaaataaagc ttggctggtg 1560
cacaggcaat ggttcctaga cctgccgtta ccatggttgc ccggagcgga cacacaaggg 1620
tcaaattgga tacagaaaga gacattggtc actttcaaaa atccccatgc gaagaaacag 1680
gatgttgttg ttttaggatc ccaagaaggg gccatgcaca cagcacttac aggggccaca 1740
gaaatccaaa tgtcatcagg aaacttactc ttcacaggac atctcaagtg caggctgaga 1800
atggacaagc tacagctcaa aggaatgtca tactctatgt gcacaggaaa gtttaaagtt 1860

-continued

```
gtgaaggaaa tagcagaaac acaacatgga acaatagtta tcagagtgca atatgaaggg   1920

gacggctctc catgcaagat ccccttttgag ataatggatt tggaaaaaag acatgtctta   1980

ggtcgcctga ttacagtcaa cccaattgtg acagaaaaag atagcccagt caacatagaa   2040

gcagaacctc cattcggaga cagctacatc atcataggag tagagccggg acaactgaag   2100

ctcaactggt ttaagaaagg aagttctatc ggccaaatgt ttgagacaac aatgaggggg   2160

gcgaagagaa tggccatttt aggtgacaca gcctgggatt ttggatcctt gggaggagtg   2220

tttacatcta taggaaaggc tctccaccaa gtctttggag caatctatgg agctgccttc   2280

agtggggttt catggactat gaaaatcctc ataggagtca ttatcacatg gataggaatg   2340

aattcacgca gcacctcact gtctgtgaca ctagtattgg tgggaattgt gacactgtat   2400

ttgggagtca tggtgcaggc cgatagtggt tgcgttgtga gctggaaaaa caaagaactg   2460

aaatgtggca gtgggatttt catcacagac aacgtgcaca catggacaga acaatacaag   2520

ttccaaccag aatccccttc aaaactagct tcagctatcc agaaagccca tgaagagggc   2580

atttgtggaa tccgctcagt aacaagactg gagaatctga tgtggaaaca aataacacca   2640

gaattgaatc acattctatc agaaaatgag gtgaagttaa ctattatgac aggagacatc   2700

aaaggaatca tgcaggcagg aaaacgatct ctgcggcctc agcccactga gctgaagtat   2760

tcatggaaaa catggggcaa agcaaaaatg ctctctacag agtctcataa ccagaccttt   2820

ctcattgatg gccccgaaac agcagaatgc cccaacacaa atagagcttg gaattcgttg   2880

gaagttgaag actatggctt tggagtattc accaccaata tatggctaaa attgaaagaa   2940

aaacaggatg tattctgcga ctcaaaactc atgtcagcgg ccataaaaga caacagagcc   3000

gtccatgccg atatgggtta ttggatagaa agtgcactca atgacacatg gaagatagag   3060

aaagcctctt tcattgaagt taaaaactgc cactggccaa aatcacacac cctctggagc   3120

aatggagtgc tagaaagtga gatgataatt ccaaagaatc tcgctggacc agtgtctcaa   3180

cacaactata gaccaggcta ccatacacaa ataacaggac catggcatct aggtaagctt   3240

gagatggact ttgatttctg tgatggaaca acagtggtag tgactgagga ctgcggaaat   3300

agaggaccct ctttgagaac aaccactgcc tctggaaaac tcataacaga atggtgctgc   3360

cgatcttgca cattaccacc gctaagatac agaggtgagg atgggtgctg gtacgggatg   3420

gaaatcagac cattgaagga gaaagaagag aatttggtca actccttggt cacagctgga   3480

catgggcagg tcgacaactt ttcactagga gtcttgggaa tggcattgtt cctggaggaa   3540

atgcttagga cccgagtagg aacgaaacat gcaatactac tagttgcagt ttcttttgtg   3600

acattgatca cagggaacat gtcctttaga gacctgggaa gagtgatggt tatggtaggc   3660

gccactatga cggatgacat aggtatgggc gtgacttatc ttgccctact agcagccttc   3720

aaagtcagac caacttttgc agctggacta ctcttgagaa agctgacctc caaggaattg   3780

atgatgacta ctataggaat tgtactcctc tcccagagca ccataccaga gaccattctt   3840

gagttgactg atgcgttagc cttaggcatg atggtcctca aaatggtgag aaatatggaa   3900

aagtatcaat tggcagtgac tatcatggct atcttgtgcg tcccaaacgc agtgatatta   3960

caaaacgcat ggaaagtgag ttgcacaata ttggcagtgg tgtccgtttc cccactgctc   4020

ttaacatcct cacagcaaaa aacagattgg ataccattag cattgacgat caaaggtctc   4080

aatccaacag ctatttttct aacaaccctc tcaagaacca gcaagaaaag gagctggcca   4140

ttaaatgagg ctatcatggc agtcgggatg gtgagcattt tagccagttc tctcctaaaa   4200

aatgatattc ccatgacagg accattagtg gctggagggc tcctcactgt gtgctacgtg   4260
```

-continued

```
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgttcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattctt gatgagcgga   6600
```

-continued

```
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
```

-continued

```
tggcttggag cacgcttctt agagtttgaa gccctaggat tcttaaatga agatcactgg   9060

ttctccagag agaactccct gagtggagtg gaaggagaag ggctgcacaa gctaggttac   9120

attctaagag acgtgagcaa gaaagaggga ggagcaatgt atgccgatga caccgcagga   9180

tgggatacaa gaatcacact agaagaccta aaaaatgaag aaatggtaac aaaccacatg   9240

gaaggagaac acaagaaact agccgaggcc attttcaaac taacgtacca aaacaaggtg   9300

gtgcgtgtgc aaagaccaac accaagaggc acagtaatgg acatcatatc gagaagagac   9360

caaagaggta gtggacaagt tggcacctat ggactcaata ctttcaccaa tatggaagcc   9420

caactaatca gacagatgga gggagaagga gtctttaaaa gcattcagca cctaacaatc   9480

acagaagaaa tcgctgtgca aaactggtta gcaagagtgg ggcgcgaaag gttatcaaga   9540

atggccatca gtggagatga ttgtgttgtg aaacctttag atgacaggtt cgcaagcgct   9600

ttaacagctc taaatgacat gggaaagatt aggaaagaca tacaacaatg ggaaccttca   9660

agaggatgga atgattggac acaagtgccc ttctgttcac accatttcca tgagttaatc   9720

atgaaagacg gtcgcgtact cgttgttcca tgtagaaacc aagatgaact gattggcaga   9780

gcccgaatct cccaaggagc agggtggtct ttgcgggaga cggcctgttt ggggaagtct   9840

tacgcccaaa tgtggagctt gatgtacttc cacagacgcg acctcaggct ggcggcaaat   9900

gctatttgct cggcagtacc atcacattgg gttccaacaa gtcgaacaac ctggtccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 4
<211> LENGTH: 37
<212> TYPE: DNA
<213> ORGANISM: Artificial sequence
<220> FEATURE:
<223> OTHER INFORMATION: primer

<400> SEQUENCE: 4

```
gttttcccag tcacgacacg tggaccgaca aagacag                              37
```

<210> SEQ ID NO 5
<211> LENGTH: 36
<212> TYPE: DNA
<213> ORGANISM: Artificial sequence
<220> FEATURE:
<223> OTHER INFORMATION: primer -continued

<400> SEQUENCE: 5
aacagctatg accatgttcc tcctgaaacc ccttcc 36

<210> SEQ ID NO 6
<211> LENGTH: 36
<212> TYPE: DNA
<213> ORGANISM: Artificial sequence
<220> FEATURE:
<223> OTHER INFORMATION: primer

<400> SEQUENCE: 6
gttttcccag tcacgacatc acgtacaagt gtcccc 36

<210> SEQ ID NO 7
<211> LENGTH: 37
<212> TYPE: DNA
<213> ORGANISM: Artificial sequence
<220> FEATURE:
<223> OTHER INFORMATION: primer

<400> SEQUENCE: 7
aacagctatg accatgagca acaccatctc attgaag 37

<210> SEQ ID NO 8
<211> LENGTH: 42
<212> TYPE: DNA
<213> ORGANISM: Artificial
<220> FEATURE:
<223> OTHER INFORMATION: primer

<400> SEQUENCE: 8
gttttcccag tcacgactgc aaccagaaaa cttggaatac ac 42

<210> SEQ ID NO 9
<211> LENGTH: 39
<212> TYPE: DNA
<213> ORGANISM: Artificial sequence
<220> FEATURE:
<223> OTHER INFORMATION: primer

<400> SEQUENCE: 9
aacagctatg accatggctc catagattgc tccaaagac 39

<210> SEQ ID NO 10
<211> LENGTH: 41
<212> TYPE: DNA
<213> ORGANISM: Artificial sequence
<220> FEATURE:
<223> OTHER INFORMATION: primer

<400> SEQUENCE: 10
gttttcccag tcacgacccc agtcaacata gaagcagaac c 41

<210> SEQ ID NO 11
<211> LENGTH: 40
<212> TYPE: DNA
<213> ORGANISM: Artificial sequence
<220> FEATURE:
<223> OTHER INFORMATION: primer

<400> SEQUENCE: 11
aacagctatg accatgccaa agccatagtc ttcaacttcc 40

<210> SEQ ID NO 12
<211> LENGTH: 36

-continued

<212> TYPE: DNA
<213> ORGANISM: Artificial sequence
<220> FEATURE:
<223> OTHER INFORMATION: primer

<400> SEQUENCE: 12
gttttcccag tcacgacatc atgcaggcag gaaaac 36

<210> SEQ ID NO 13
<211> LENGTH: 37
<212> TYPE: DNA
<213> ORGANISM: Artificial sequence
<220> FEATURE:
<223> OTHER INFORMATION: primer

<400> SEQUENCE: 13
aacagctatg accatgacca taaccatcac tcttccc 37

<210> SEQ ID NO 14
<211> LENGTH: 37
<212> TYPE: DNA
<213> ORGANISM: Artificial sequence
<220> FEATURE:
<223> OTHER INFORMATION: primer

<400> SEQUENCE: 14
aacagctatg accatgacca taaccatcac tcttccc 37

<210> SEQ ID NO 15
<211> LENGTH: 36
<212> TYPE: DNA
<213> ORGANISM: Artificial sequence
<220> FEATURE:
<223> OTHER INFORMATION: primer

<400> SEQUENCE: 15
aacagctatg accatggctc tctccagttc caaatc 36

<210> SEQ ID NO 16
<211> LENGTH: 38
<212> TYPE: DNA
<213> ORGANISM: Artificial sequence
<220> FEATURE:
<223> OTHER INFORMATION: priemr

<400> SEQUENCE: 16
gttttcccag tcacgacaag aaccagcaag aaaaggag 38

<210> SEQ ID NO 17
<211> LENGTH: 38
<212> TYPE: DNA
<213> ORGANISM: Artificial sequence
<220> FEATURE:
<223> OTHER INFORMATION: primer

<400> SEQUENCE: 17
aacagctatg accatgcacc attaccataa agacccac 38

<210> SEQ ID NO 18
<211> LENGTH: 37
<212> TYPE: DNA
<213> ORGANISM: Artificial sequence
<220> FEATURE:
<223> OTHER INFORMATION: primer

<400> SEQUENCE: 18

-continued gttttcccag tcacgacttg aaccatcatg ggcggac 37

<210> SEQ ID NO 19
<211> LENGTH: 41
<212> TYPE: DNA
<213> ORGANISM: Artificial sequence
<220> FEATURE:
<223> OTHER INFORMATION: primer

<400> SEQUENCE: 19
aacagctatg accatgtcct gcttttatac ttggaacgaa c 41

<210> SEQ ID NO 20
<211> LENGTH: 36
<212> TYPE: DNA
<213> ORGANISM: Artificial sequence
<220> FEATURE:
<223> OTHER INFORMATION: primer

<400> SEQUENCE: 20
gttttcccag tcacgacaag cccatttcac agaccc 36

<210> SEQ ID NO 21
<211> LENGTH: 38
<212> TYPE: DNA
<213> ORGANISM: Artificial sequence
<220> FEATURE:
<223> OTHER INFORMATION: primer

<400> SEQUENCE: 21
aacagctatg accatgtcaa tttcttcctt tccccttc 38

<210> SEQ ID NO 22
<211> LENGTH: 38
<212> TYPE: DNA
<213> ORGANISM: Artificial sequence
<220> FEATURE:
<223> OTHER INFORMATION: primer

<400> SEQUENCE: 22
gttttcccag tcacgacgag aggagaagca aggaaaac 38

<210> SEQ ID NO 23
<211> LENGTH: 35
<212> TYPE: DNA
<213> ORGANISM: Artificial sequence
<220> FEATURE:
<223> OTHER INFORMATION: primer

<400> SEQUENCE: 23
aacagctatg accatgaggg acacattcac tgagg 35

<210> SEQ ID NO 24
<211> LENGTH: 36
<212> TYPE: DNA
<213> ORGANISM: Artificial sequence
<220> FEATURE:
<223> OTHER INFORMATION: primer

<400> SEQUENCE: 24
gttttcccag tcacgacaca gagaacaccc caagac 36

<210> SEQ ID NO 25
<211> LENGTH: 35
<212> TYPE: DNA
<213> ORGANISM: Artificial sequence -continued
<220> FEATURE:
<223> OTHER INFORMATION: primer

<400> SEQUENCE: 25
aacagctatg accatgtcca cttcctggat tccac 35

<210> SEQ ID NO 26
<211> LENGTH: 39
<212> TYPE: DNA
<213> ORGANISM: Artificial sequence
<220> FEATURE:
<223> OTHER INFORMATION: primer

<400> SEQUENCE: 26
gttttcccag tcacgacaca agtaatgctc ctagtcctc 39

<210> SEQ ID NO 27
<211> LENGTH: 38
<212> TYPE: DNA
<213> ORGANISM: Artificial sequence
<220> FEATURE:
<223> OTHER INFORMATION: primer

<400> SEQUENCE: 27
aacagctatg accatgttca ctgatgacac tatgttcc 38

<210> SEQ ID NO 28
<211> LENGTH: 37
<212> TYPE: DNA
<213> ORGANISM: Artificial sequence
<220> FEATURE:
<223> OTHER INFORMATION: primer

<400> SEQUENCE: 28
gttttcccag tcacgacgtc atcaccaaat cccacag 37

<210> SEQ ID NO 29
<211> LENGTH: 39
<212> TYPE: DNA
<213> ORGANISM: Artificial sequence
<220> FEATURE:
<223> OTHER INFORMATION: priemr

<400> SEQUENCE: 29
aacagctatg accatggctt cttctctctt tttcccatc 39

<210> SEQ ID NO 30
<211> LENGTH: 36
<212> TYPE: DNA
<213> ORGANISM: Artificial sequence
<220> FEATURE:
<223> OTHER INFORMATION: primer

<400> SEQUENCE: 30
gttttcccag tcacgacaag gtgagaagca atgcag 36

<210> SEQ ID NO 31
<211> LENGTH: 37
<212> TYPE: DNA
<213> ORGANISM: Artificial sequence
<220> FEATURE:
<223> OTHER INFORMATION: primer

<400> SEQUENCE: 31
aacagctatg accatgtgga aatggtgtga acagaag 37

-continued

<210> SEQ ID NO 32
<211> LENGTH: 39
<212> TYPE: DNA
<213> ORGANISM: Artificial sequence
<220> FEATURE:
<223> OTHER INFORMATION: primer

<400> SEQUENCE: 32
gttttcccag tcacgacgca ttcagcacct aacaatcac 39

<210> SEQ ID NO 33
<211> LENGTH: 35
<212> TYPE: DNA
<213> ORGANISM: Artificial sequence
<220> FEATURE:
<223> OTHER INFORMATION: primer

<400> SEQUENCE: 33
aacagctatg accatgggca tttatgatgg cctga 35

<210> SEQ ID NO 34
<211> LENGTH: 17
<212> TYPE: DNA
<213> ORGANISM: Artificial sequence
<220> FEATURE:
<223> OTHER INFORMATION: primer

<400> SEQUENCE: 34
ccatggaagc tgtacgc 17

<210> SEQ ID NO 35
<211> LENGTH: 36
<212> TYPE: DNA
<213> ORGANISM: Artificial sequence
<220> FEATURE:
<223> OTHER INFORMATION: primer

<400> SEQUENCE: 35
aacagctatg accatgtgat tcaacagcac cattcc 36

<210> SEQ ID NO 36
<211> LENGTH: 17
<212> TYPE: DNA
<213> ORGANISM: Artificial sequence
<220> FEATURE:
<223> OTHER INFORMATION: primer tail

<400> SEQUENCE: 36
gttttcccag tcacgac 17

<210> SEQ ID NO 37
<211> LENGTH: 16
<212> TYPE: DNA
<213> ORGANISM: Artificial sequence
<220> FEATURE:
<223> OTHER INFORMATION: primer tail

<400> SEQUENCE: 37
aacagctatg accatg 16

<210> SEQ ID NO 38
<211> LENGTH: 10723
<212> TYPE: DNA
<213> ORGANISM: Dengue virus
<220> FEATURE:
<221> NAME/KEY: misc_feature -continued

<222> LOCATION: (1)..(10723)
<223> OTHER INFORMATION: LAV2

<400> SEQUENCE: 38
agttgttagt ctacgtggac cgacaaagac agattctttg agggagctaa gctcaatgta 60
gttctaacag tttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggttggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgggaat gggactggag acacgaactg aaacatggat gtcatcagaa 780
ggggcctgga aacatgtcca gagaattgaa acttggatct tgagacatcc aggcttcacc 840
atgatggcag caatcctggc atacaccata ggaacgacac atttccaaag agccctgatt 900
ttcatcttac tgacagctgt cactccttca atgacaatgc gttgcatagg aatgtcaaat 960
agagactttg tggaaggggt ttcaggagga agctgggttg acatagtctt agaacatgga 1020
agctgtgtga cgacgatggc aaaaaacaaa ccaacattgg attttgaact gataaaaaca 1080
gaagccaaac agcctgccac cctaaggaag tactgtatag aggcaaagct aaccaacaca 1140
acaacagaat ctcgctgccc aacacaaggg gaacccagcc taaatgaaga gcaggacaaa 1200
aggttcgtct gcaaacactc catggtagac agaggatggg gaaatggatg tggactattt 1260
ggaaagggag gcattgtgac ctgtgctatg ttcagatgca aaaagaacat ggaaggaaaa 1320
gttgtgcaac cagaaaactt ggaatacacc attgtgataa cacctcactc aggggaagag 1380
catgcagtcg gaaatgacac aggaaaacat ggcaaggaaa tcaaaataac accacagagt 1440
tccatcacag aagcagaatt gacaggttat ggcactgtca caatggagtg ctctccaaga 1500
acgggcctcg acttcaatga gatggtgttg ctgcagatgg aaaataaagc ttggctggtg 1560
cacaggcaat ggttcctaga cctgccgtta ccatggttgc ccggagcgga cacacaaggg 1620
tcaaattgga tacagaaaga gacattggtc actttcaaaa atccccatgc gaagaaacag 1680
gatgttgttg ttttaggatc ccaagaaggg gccatgcaca cagcacttac aggggccaca 1740
gaaatccaaa tgtcatcagg aaacttactc ttcacaggac atctcaagtg caggctgaga 1800
atggacaagc tacagctcaa aggaatgtca tactctatgt gcacaggaaa gtttaaagtt 1860
gtgaaggaaa tagcagaaac acaacatgga acaatagtta tcagagtgca atatgaaggg 1920
gacggctctc catgcaagat cccttttgag ataatggatt tggaaaaaag acatgtctta 1980
ggtcgcctga ttacagtcaa cccaattgtg acagaaaaag atagcccagt caacatagaa 2040
gcagaacctc catttggaga cagctacatc atcataggag tagagccggg acaactgaag 2100
ctcaactggt ttaagaaagg aagttctatc ggccaaatgt ttgagacaac aatgaggggg 2160
gcgaagagaa tggccatttt aggtgacaca gcctgggatt ttggatcctt gggaggagtg 2220

-continued

```
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc ccccactgttc  4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
```

-continued

```
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgw gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600
aggggcatag ggaagatgac cctgggaatg tgctgcataa tcacggctag catcctccta   6660
tggtacgcac aaatacagcc acactggata gcagcttcaa taatactgga gtttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
```

-continued

```
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt tgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
```

-continued caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 39
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: VDV1

<400> SEQUENCE: 39
agttgttagt ctacgtggac cgacaagaac agtttcgaat cggaagcttg cttaacgtag 60
ttctaacagt tttttattag agagcagatc tctgatgatc aaccaacgaa aaaagacggg 120
tcgaccgtct ttcaatatgc tgaaacgcgc gagaaaccgc gtgtcaactg tttcacagtt 180
ggcgaagaga ttctcaaaag gattgctctc aggccaagga cccatgaaat tggtgatggc 240
tttcatagca ttcttaagat ttctagccat acccccaaca gcaggaattt tggctagatg 300
gggctcattc aagaagaatg gagcgattaa agtgttacgg ggtttcaaga gagaaatctc 360
aaacatgcta aacataatga acaggaggaa aagatccgtg accatgctcc ttatgctgct 420
gcccacagcc ctggcgttcc atctgacgac acgagggggga gagccgcata tgatagttag 480
caagcaggaa agaggaaagt cacttttgtt caagacctct gcaggtgtca acatgtgcac 540
cctcattgcg atggatttgg gagagttgtg tgaggacacg atgacctaca aatgccccccg 600

-continued gatcactgag gcggaaccag atgacgttga ctgttggtgc aatgccacgg acacatgggt 660
gacctatgga acgtgctctc aaactggcga acaccgacga gacaaacgtt ccgtcgcatt 720
ggccccacac gtggggcttg gcctagaaac aagagccgaa acgtggatgt cctctgaagg 780
tgcttggaaa cagatacaaa aagtagagac ttgggctctg agacatccag gattcacggt 840
gatagccctt tttctagcac atgccatagg aacatccatc acccagaaag ggatcatttt 900
cattttgctg atgctggtaa caccatctat ggccatgcga tgcgtgggaa taggcaacag 960
agacttcgtg gaaggactgt caggagcaac atgggtggat gtggtactgg agcatggaag 1020
ttgcgtcacc accatggcaa aaaacaaacc aacactggac attgaactct tgaagacgga 1080
ggtcacaaac cctgcagttc tgcgtaaatt gtgcattgaa gctaaaatat caaacaccac 1140
caccgattcg agatgtccaa cacaaggaga agccacactg gtggaagaac aagacgcgaa 1200
ctttgtgtgc cgacgaacgt tcgtggacag aggctggggc aatggctgtg ggctattcgg 1260
aaaaggtagt ctaataacgt gtgccaagtt taagtgtgtg acaaaactag aaggaaagat 1320
agctcaatat gaaaacctaa aatattcagt gatagtcacc gtccacactg gagatcagca 1380
ccaggtggga aatgagacta cagaacatgg aacaactgca accataacac ctcaagctcc 1440
tacgtcggaa atacagctga ccgactacgg aacccttaca ttagattgtt cacctaggac 1500
agggctagat tttaacgaga tggtgttgct gacaatgaaa aagaaatcat ggcttgtcca 1560
caaacagtgg tttctagact taccactgcc ttggacctct ggggctttaa catcccaaga 1620
gacttggaac agacaagatt tactggtcac atttaagaca gctcatgcaa agaagcagga 1680
agtagtcgta ctaggatcac aagaaggagc aatgcacact gcgctgactg gagcgacaga 1740
aatccaaacg tcaggaacga caacaatttt cgcaggacac ctaaaatgca gactaaaaat 1800
ggacaaacta actttaaaag ggatgtcata tgtgatgtgc acaggctcat tcaagttaga 1860
gaaagaagtg gctgagaccc agcatggaac tgttctggtg caggttaaat atgaaggaac 1920
agacgcacca tgcaagattc ccttttcgac ccaagatgag aaaggagcaa cccagaatgg 1980
gagattaata acagccaacc ccatagtcac tgacaaagaa aaaccagtca atattgaggc 2040
agaaccaccc tttggtgaga gctacatcgt ggtaggagca ggtgaaaaag ctttgaaact 2100
aagctggttc aagaaaggaa gcagcatagg gaaaatgttt gaagcaactg cccgaggagc 2160
acgaaggatg gccattctgg gagacaccgc atgggacttc ggttctatag gaggagtgtt 2220
cacgtctatg ggaaaactgg tacaccaggt ttttggaact gcatatggag ttttgtttag 2280
cggagtttct tggaccatga aaataggaat agggattctg ctgacatggc taggattaaa 2340
ttcaaggaac acgtcccttt cggtgatgtg catcgcagtt ggcatggtca cactgtacct 2400
aggagtcatg gttcaggcag attcgggatg tgtaatcaac tggaaaggca gagaacttaa 2460
atgtggaagc ggcatttttg tcactaatga agttcacact tggacagagc aatacaaatt 2520
ccaggctgac tcccccaaga gactatcagc agccattggg aaggcatggg aggagggtgt 2580
gtgtggaatc cgatcagcca ctcgtctcga gaacatcatg tggaaacaaa tatcaaatga 2640
attgaaccac atcctacttg aaaatgacat gaaatttaca gtggtcgtgg gagacgttag 2700
tggaatcttg gcccaaggaa aaaaaatgat taggccacaa cccatggaac acaaatactc 2760
gtggaaaagc tggggaaaag ctaaaatcat aggagcggat gtacagaaca ccaccttcat 2820
catcgacggc ccaaacaccc cagaatgccc tgacaatcaa agagcatgga atatttggga 2880
agtagaggac tatggatttg ggattttcac gacaaacata tggttgaaat tgcgtgactc 2940

-continued

```
ctacacccaa gtatgtgacc accggctgat gtcagctgcc attaaggaca gcaaggcagt   3000
ccatgctgac atggggtact ggatagaaag tgaaaagaac gagacatgga agttggcgag   3060
agcctccttt atagaagtta agacatgcat ctggccaaaa tcccacactc tatggagcaa   3120
tggagttctg gaaagtgaaa tgataattcc aaagatatat ggaggaccaa tatctcagca   3180
caactacaga ccaggatatt tcacacaaac agcagggccg tggcacctag gcaagttgga   3240
actagatttc gatttttgtg aaggtaccac agttgttgtg gatgaacatt gtggaaatcg   3300
aggaccatct ctcagaacca caacagtcac aggaaagata atccatgaat ggtgctgcag   3360
atcttgtacg ctaccccccc tacgtttcaa aggggaagac gggtgttggt acggcatgga   3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctgggggat ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta taacagaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc ctttttgtgt ggtatttttg   4500
gcagaaaaag aaacagagat caggagtgct atgggacaca cccagccccc cagaagtgga   4560
aagagcagtt cttgatgatg gcatctatag aattttgcaa agaggactgt tgggcaggtc   4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
```

-continued

```
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa aaaatgatga ggaccacgct cattggacag aagcaaagat   6000
gctccttgac aatataaaca caccagaagg gattatccca gccctctttg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcgtgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacag ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
```

-continued

```
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaggct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac accctttgga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatggggaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca aacttggata   9120
catactcaga gacatatcaa ggattccagg ggggaacatg tatgcagatg acacagccgg   9180
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtctgaggg aatcttttta cccagcgaat tggaaacccc   9480
aaatctagcc ggaagagttc tcgactggtt ggaaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaaagt aagaaaagac ataccacaat gggaaccttc   9660
aaaaggatgg aatgattggc aacaagtgcc tttctgttca caccacttcc accagctaat   9720
tatgaaggat gggagggaga tagtggtgcc atgccgcaac caagatgaac ttgtggggag   9780
ggccagagta tcacaaggcg ccggatggag cctgagagaa accgcatgcc taggcaagtc   9840
atatgcacaa atgtggcagc tgatgtattt ccacaggaga gacctgagac tggcggctaa   9900
cgctatttgt tcagccgttc cagttgattg ggtcccaacc agccgcacca cctggtcgat   9960
ccatgcccat caccaatgga tgacaacaga agacatgtta tcagtatgga atagggtctg  10020
gatagaggaa aacccatgga tggaggataa gactcatgtg tccagttggg aagaagttcc  10080
```

-continued

```
atacctagga aagagggaag atcagtggtg tggatccctg ataggcttaa cagcaagggc  10140

cacctgggcc actaatatac aagtggccat aaaccaagtg agaaggctca ttgggaatga  10200

gaattatcta gattacatga catcaatgaa gagattcaag aatgagagtg atcccgaagg  10260

ggcactctgg taagtcaaca cattcacaaa ataaaggaaa ataaaaaatc aaatgaggca  10320

agaagtcagg ccagattaag ccatagtacg gtaagagcta tgctgcctgt gagccccgtc  10380

caaggacgta aaatgaagtc aggccgaaag ccacggtttg agcaagccgt gctgcctgtg  10440

gctccatcgt ggggatgtaa aaacccggga ggctgcaacc catggaagct gtacgcatgg  10500

ggtagcagac tagtggttag aggagacccc tcccaagaca caacgcagca gcggggccca  10560

acaccagggg aagctgtacc ctggtggtaa ggactagagg ttagaggaga ccccccgcgt  10620

aacaataaac agcatattga cgctgggaga gaccagagat cctgctgtct ctacagcatc  10680

attccaggca cagaacgcca gaaaatggaa tggtgctgtt gaatcaacag gttct       10735
```

```
<210> SEQ ID NO 40
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: LAV1/PDK13

<400> SEQUENCE: 40
```

```
agttgttagt ctacgtggac cgacaagaac agtttcgaat cggaagcttg cttaacgtag     60

ttctaacagt tttttattag agagcagatc tctgatgatc aaccaacgaa aaaagacggg    120

tcgaccgtct ttcaatatgc tgaaacgcgc gagaaaccgc gtgtcaactg tttcacagtt    180

ggcgaagaga ttctcaaaag gattgctctc aggccaagga cccatgaaat tggtgatggc    240

tttcatagca ttcttaagat ttctagccat acccccaaca gcaggaattt tggctagatg    300

gggctcattc aagaagaatg gagcgattaa agtgttacgg ggtttcaaga gagaaatctc    360

aaacatgcta aacataatga acaggaggaa aagatccgtg accatgctcc ttatgctgct    420

gcccacagcc ctggcgttcc atctgacgac acgaggggga gagccgcata tgatagttag    480

caagcaggaa agaggaaagt cacttttgtt caagacctct gcaggtgtca acatgtgcac    540

cctcattgcg atggatttgg gagagttgtg tgaggacacg atgacctaca aatgcccccg    600

gatcactgag gcggaaccag atgacgttga ctgttggtgc aatgccacgg acacatgggt    660

gacctatgga acgtgctctc aaactggcga acaccgacga gacaaacgtt ccgtcgcatt    720

ggccccacac gtggggcttg gcctagaaac aagagccgaa acgtggatgt cctctgaagg    780

tgcttggaaa cagatacaaa aagtagagac ttgggctctg agacatccag gattcacggt    840

gatagccctt tttctagcac atgccatagg aacatccatc acccagaaag ggatcatttt    900

cattttgctg atgctggtaa caccatctat ggccatgcga tgcgtgggaa taggcaacag    960

agacttcgtg gaaggactgt caggagcaac atgggtggat gtggtactgg agcatggaag   1020

ttgcgtcacc accatggcaa aaaacaaacc aacactggac attgaactct tgaagacgga   1080

ggtcacaaac cctgcagttc tgcgtaaatt gtgcattgaa gctaaaatat caaacaccac   1140

caccgattcg agatgtccaa cacaaggaga agccacactg gtggaagaac aagacgcgaa   1200

ctttgtgtgc cgacgaacgt tcgtggacag aggctggggc aatggctgtg ggctattcgg   1260

aaaaggtagt ctaataacgt gtgccaagtt taagtgtgtg acaaaactag aaggaaagat   1320
```

-continued

```
agctcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa aagaaatcat ggcttgtcca   1560
caaacagtgg tttctagact taccactgcc ttggacctct ggggctttaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
cacgtctatg ggaaaactgg tacaccaggt ttttggaact gcatatggag ttttgtttag   2280
cggagtttct tggaccatga aaataggaat agggattctg ctgacatggc taggattaaa   2340
ttcaaggaac acgtcccttt cggtgatgtg catcgcagtt ggcatggtca cactgtacct   2400
aggagtcatg gttcaggcag attcgggatg tgtaatcaac tggaaaggca gagaacttaa   2460
atgtggaagc ggcatttttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
attgaaccac atcctacttg aaaatgacat gaaatttaca gtggtcgtgg gagacgttag   2700
tggaatcttg gcccaaggga aaaaaatgat taggccacaa cccatggaac acaaatactc   2760
gtggaaaagc tggggaaaag ctaaaatcat aggagcggat gtacagaaca ccaccttcat   2820
catcgacggc ccaaacaccc cagaatgccc tgacaatcaa agagcatgga atatttggga   2880
agtagaggac tatggatttg ggattttcac gacaaacata tggttgaaat tgcgtgactc   2940
ctacacccaa gtatgtgacc accggctgat gtcagctgcc attaaggaca gcaaggcagt   3000
ccatgctgac atggggtact ggatagaaag tgaaaagaac gagacatgga agttggcgag   3060
agcctccttt atagaagtta agacatgcat ctggccaaaa tcccacactc tatggagcaa   3120
tggagttctg gaaagtgaaa tgataattcc aaagatatat ggaggaccaa tatctcagca   3180
caactacaga ccaggatatt tcacacaaac agcagggccg tggcacctag gcaagttgga   3240
actagatttc gatttttgtg aaggtaccac agttgttgtg gatgaacatt gtggaaatcg   3300
aggaccatct ctcagaacca caacagtcac aggaaagata atccatgaat ggtgctgcag   3360
atcttgtacg ctacccccc tacgtttcaa aggggaagac gggtgttggt acggcatgga   3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
```

-continued

```
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctgggggat ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta taacagaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc ctttttgtgt ggtatttttg   4500
gcagaaaaag aaacagagat caggagtgct atgggacaca cccagccccc cagaagtgga   4560
aagagcagtt cttgatgatg gcatctatag aattttgcaa agaggactgt tgggcaggtc   4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa acaatgatga ggaccacgct cattggacag aagcaaagat   6000
gctccttgac aatataaaca caccagaagg gattatccca gccctctttg agccggagag   6060
```

-continued

```
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact cccacaggaca accagctagc   6780
atatgtggtg ataggtctgt tattcgtgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacag ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaagct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
```

-continued

```
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac accctttgga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatggggaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca aacttggata   9120
catactcaga gacatatcaa ggattccagg ggggaacatg tatgcagatg acacagccgg   9180
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtctgaggg aatcttttta cccagcgaat tggaaacccc   9480
aaatctagcc ggaagagttc tcgactggtt ggaaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaaagt aagaaaagac ataccacaat gggaaccttc   9660
aaaaggatgg aatgattggc aacaagtgcc tttctgttca caccacttcc accagctaat   9720
tatgaaggat gggagggaga tagtggtgcc atgccgcaac caagatgaac ttgtggggag   9780
ggccagagta tcacaaggcg ccggatggag cctgagagaa accgcatgcc taggcaagtc   9840
atatgcacaa atgtggcagc tgatgtattt ccacaggaga gacctgagac tggcggctaa   9900
cgctatttgt tcagccgttc cagttgattg ggtcccaacc agccgcacca cctggtcgat   9960
ccatgcccat caccaatgga tgacaacaga agacatgtta tcagtatgga atagggtctg  10020
gatagaggaa aacccatgga tggaggataa gactcatgtg tccagttggg aagaagttcc  10080
atacctagga aagagggaag atcagtggtg tggatccctg ataggcttaa cagcaagggc  10140
cacctgggcc actaatatac aagtggccat aaaccaagtg agaaggctca ttgggaatga  10200
gaattatcta gattacatga catcaatgaa gagattcaag aatgagagtg atcccgaagg  10260
ggcactctgg taagtcaaca cattcacaaa ataaaggaaa ataaaaaatc aaatgaggca  10320
agaagtcagg ccagattaag ccatagtacg gtaagagcta tgctgcctgt gagccccgtc  10380
caaggacgta aaatgaagtc aggccgaaag ccacggtttg agcaagccgt gctgcctgtg  10440
gctccatcgt ggggatgtaa aaacccggga ggctgcaacc catggaagct gtacgcatgg  10500
ggtagcagac tagtggttag aggagacccc tcccaagaca caacgcagca gcggggccca  10560
acaccagggg aagctgtacc ctggtggtaa ggactagagg ttagaggaga ccccccgcgt  10620
aacaataaac agcatattga cgctgggaga gaccagagat cctgctgtct ctacagcatc  10680
attccaggca cagaacgcca gaaaatggaa tggtgctgtt gaatcaacag gttct       10735
```

<210> SEQ ID NO 41

-continued

<211> LENGTH: 10699
<212> TYPE: DNA
<213> ORGANISM: Dengue virus
<220> FEATURE:
<221> NAME/KEY: misc_feature
<222> LOCATION: (1)..(10699)
<223> OTHER INFORMATION: LAV3

<400> SEQUENCE: 41
agttgttagt ctacgtggac cgacaagaac agtttcgact cggaagcttg cttaacgtag 60
tgctgacagt tttttattag agagcagatc tctgatgaac aaccaacgga aaaagacggg 120
aaaaccgtct atcaatatgc tgaaacgcgt gagaaaccgt gtgtcaactg gatcacagtt 180
ggcgaagaga ttctcaagag gattgctgaa cggccaagga ccaatgaaat tggttatggc 240
atttatagct ttcctcagat ttctagccat tccaccgaca gcaggagtct tggctagatg 300
gggtaccttt aagaagtcgg gggctattaa ggtcttaaaa ggcttcaaga aggagatctc 360
aaacatgctg agcattatca acaaacggaa aaagacatcg ctctgtctca tgatgatgtt 420
accagcaaca cttgctttcc acttaacttc acgagatgga gagccgcgca tgattgtggg 480
gaagaatgaa agaggaaaat ccctactttt caagacagcc tctggaatca acatgtgcac 540
actcatagct atggatctgg gagagatgtg tgatgacacg gtcacttaca aatgccccca 600
cattaccgaa gtggagcctg aagacattga ctgctggtgc aaccttacat cgacatgggt 660
gacttatgga acatgcaatc aagctggaga gcatagacgc gataagagat cagtggcgtt 720
agctccccat gttggcatgg gactggacac acgcactcaa acctggatgt cggctgaagg 780
agcttggaga caagtcgaga aggtagagac atgggccctt aggcacccag ggtttaccat 840
actagcccta tttcttgccc attacatagg cacttccttg acccagaaag tggttatttt 900
tatactatta atgctggtta ccccatccat gacaatgaga tgtgtaggag taggaaacag 960
agattttgtg gaaggcctat cgggagctac gtgggttgac gtggtgctcg agcacggtgg 1020
gtgtgtgact accatggcta agaacaagcc cacgctggac atagagcttc agaagaccga 1080
ggccacccaa ctggcgaccc taaggaagct atgcattgag ggaaaaatta ccaacataac 1140
aaccgactca agatgtccca cccaagggga agcgatttta cctgaggagc aggaccagaa 1200
ctacgtgtgt aagcatacat acgtggacag aggctgggga aacggttgtg gtttgtttgg 1260
caagggaagc ttggtgacat gcgcgaaatt tcaatgttta gaatcaatag agggaaaagt 1320
ggtgcaacat gagaacctca aatacaccgt catcatcaca gtgcacacag gagaccaaca 1380
ccaggtggga aatgaaacgc agggagtcac ggctgagata acaccccagg catcaaccgc 1440
tgaagccatt ttacctgaat atggaaccct cgggctagaa tgctcaccac ggacaggttt 1500
ggatttcaat gaaatgatct yattgacaat gaagaacaaa gcatggatgg tacatagaca 1560
atggttcttt gacttacccc taccatggac atcaggagct acagcagaaa caccaacttg 1620
gaacaggaaa gagcttcttg tgacatttaa aaatgcacat gcaaaaaagc aagaagtagt 1680
tgttcttgga tcacaagagg gagcaatgca tacagcactg acaggagcta cagagatcca 1740
aacctcagga ggcacaagta tctttgcggg gcacttaaaa tgtagactca agatggacaa 1800
attggaactc aaagggatga gctatgcaat gtgcttgggt agctttgtgt tgaagaaaga 1860
agtctccgaa acgcagcatg ggacaatact cattaaggtt gagtacaaag ggaaagatgc 1920
accctgcaag attccttttct ccacggagga tggacaagga aaagctcaca atggcagact 1980
gatcacagcc aatccagtgg tgaccaagaa ggaggagcct gtcaacattg aggctgaacc 2040
tccttttgga gaaagtaaca tagtaattgg aattggagac aaagccctga aaatcaactg 2100

-continued

```
gtacaagaag ggaagctcga ttgggaagat gttcgaggct actgccagag gtgcaaggcg   2160
catggccatc ttgggagaca cagcctggga ctttggatca gtgggtggtg ttttgaattc   2220
attagggaaa atggtccacc aaatatttgg gagtgcttac acagccctat ttggtggagt   2280
ctcctggatg atgaaaattg gaataggtgt cctcttaacc tggatagggt tgaactcaaa   2340
aaatacttct atgtcatttt catgcatcgc gataggaatc attacactct atctgggagc   2400
cgtggtgcaa gctgacatgg ggtgtgtcat aaactggaaa ggcaaagaac tcaaatgtgg   2460
aagtggaatt ttcgtcacta atgaggtcca cacctggaca gagcaataca aatttcaagc   2520
agactccccc aagagactgg caacagccat tgcaggcgct tgggaaaatg gagtgtgcgg   2580
aattaggtca acaaccagaa tggagaacct cttgtggaag caaatagcca atgaactgaa   2640
ttacatatta tgggaaaaca acattaaatt aacggtagtt gtaggcgaca taactggggt   2700
cttagagcaa gggaaaagaa cactaacacc acaacccatg gagctaaaat attcttggaa   2760
aacatgggga aaggcaaaaa tagtgacagc tgaaacacaa aattcctctt tcataataga   2820
tgggccaagc acaccggagt gtccaagtgc ctcaagagca tggaatgtgt gggaggtgga   2880
ggattacggg ttcggagttt tcacaaccaa catatggctg aaactccgag aggtgtacac   2940
ccaactatgt gaccataggc taatgtcggc agccgtcaag gatgagaggg ctgtacatgc   3000
cgacatgggc tattggatag aaagccaaaa gaatgggagt tggaagctag aaaaagcatc   3060
cttcatagag gtgaaaacct gcacatggcc aaaatcacac actctctgga gcaatggtgt   3120
gctagagagt gacatgatta tcccaaagag tctagctggt cccatttcgc aacacaacca   3180
caggcccggg taccacaccc aaacggcagg accctggcac ttaggaaaat tggagctgga   3240
cttcaactat tgtgaaggaa caacagttgt catctcagaa aactgtggga caagaggccc   3300
atcattgaga acaacaacgg tgtcagggaa gttgatacac gaatggtgct gccgctcgtg   3360
cacacttcct cccctacgat acatgggaga agacggctgc tggtatggca tggaaatcag   3420
acccattaat gagaaagaag agaatatggt aaagtctcta gcctcagcag ggagtggaaa   3480
ggtggacaac ttcacaatgg gtgtcttgtg tttggcaatc ctctttgaag aggtgatgag   3540
aggaaaattt gggaaaaaac acatgattgc aggggttctc ttcacgtttg tgctcctcct   3600
ctcagggcaa ataacatgga gagacatggc gcacacactc ataatgattg ggtccaacgc   3660
ctctgacaga atggggatgg gcgtcactta cctagctcta attgcaacat ttaaaattca   3720
gccactcctg gctttgggat tcttcctgag gaaactgaca tctagagaaa atttattgct   3780
gggagttggg ttggccatgg cagcaacgtt acgactgcca gaggacattg aacagatggc   3840
gaatggaatt gctttggggc tcatggctct taaactgata acacaatttg aaacatacca   3900
actatggacg gcattagttt ccctaacgtg ttcaaataca attttcacgt tgactgttgc   3960
ctggagaaca gccactctga ttttagccgg aatttcgctt ttgccagtgt gccagtcttc   4020
gagcatgagg aaaacagatt ggctcccaat gactgtggca gctatgggag ctcaacccct   4080
accacttttt attttcagtc tgaaagatac actcaaaagg agaagctggc cactgaatga   4140
gggggtgatg gcagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatggaa caatgagaat   4380
aaaagatgac gagactgaga acatcttaac agtgctttta aaaacagcac tactaatagt   4440
```

-continued

```
atcaggcatc tttccatact ccatacccgc aacactgttg gtctggcata cttggcaaaa   4500
gcaaacccaa agatccggcg tcctatggga cgtacccagc cccccagaga cacagaaagc   4560
ggaactggaa gaaggggtct ataggatcaa acagcaagga atttttggga aaacccaagt   4620
gggggttgga gtacagaaag aaggagtttt ccacaccatg tggcatgtca caagaggggc   4680
agtgttgaca cacaatggga aaagactgga accaaactgg gctagcgtga aaaaagatct   4740
gatttcatac ggaggaggat ggagattgag tgcacaatgg aaaaaggggg aggaggtgca   4800
ggttattgcc gtagagcctg ggaagaaccc aaagaacttt caaaccatgc caggcatttt   4860
tcagacaaca acaggggaaa taggagcaat tgcactggat ttcaagcctg gaacttcagg   4920
atctcccatc ataaacagag agggaaaggt agtgggactg tatggcaatg gagtggttac   4980
aaagaatgga ggctatgtca gtggaatagc gcaaacaaat gcagaaccag atggaccgac   5040
accagagttg gaagaagaga tgttcaaaaa gcgaaatcta accataatgg atctccatcc   5100
tgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca caggaagaga   5280
gattgttgat ctaatgtgtc acgcaacgtt cacaatgcgc ttgctgtcac cagtcagggt   5340
tccaaactac aacttgataa taatggatga ggcccatttc acagacccag ccagtatagc   5400
ggctagaggg tacatatcaa ctcgtgtagg aatgggagag gcagccgcaa ttttcatgac   5460
agcaacaccc cctggaacag ctgatgcctt tcctcagagc aacgctccaa ttcaagatga   5520
agagagagac ataccggaac gctcatggaa ttcaggcaat gaatggatta ctgactttgt   5580
tgggaagaca gtgtggtttg tccctagcat caaagccgga aatgacatag caaactgctt   5640
gcggaaaaat ggaaaaaagg ttattcaact cagcaggaag acctttgaca cagaatatca   5700
aaagaccaaa ctgaatgatt gggactttgt ggtgacaaca gacatttcag aaatgggagc   5760
caatttcaaa gcagatagag tgatcgaccc aagaagatgt ctcaagccgg tgattttgac   5820
agatggaccc gagcgggtga tcctggctgg accaatgcca gtcaccgtag cgagcgctgc   5880
gcaaaggaga gggagagttg gcaggaaccc acaaaaagaa aatgaccagt acatattcat   5940
gggccagcct ctcaacaatg atgaagacca tgctcactgg acagaagcaa aaatgctgct   6000
ggacaacatc aacacaccag aagggattat accagctctc tttgaaccag aaagggagaa   6060
gtcagccgcc atagacggcg aataccgcct gaagggtgag tccaggaaga ctttcgtgga   6120
actcatgagg aggggtgacc tcccagtttg gctagcccat aaagtagcat cagaagggat   6180
caaatataca gatagaaaat ggtgctttga tggagaacgt aataatcaaa ttttagagga   6240
gaatatggat gtggaaatct ggacaaagga aggagaaaag aaaaaactga gacctaggtg   6300
gcttgatgcc cgcacttatt cagatccttt agcactcaaa gaattcaagg attttgcagc   6360
tggcagaaag tcaatcgccc ttgatcttgt gacagaaata ggaagagtgc cttcacactt   6420
agcccacaga acgagaaacg ccctggataa tttggtgatg ctgcacacgt cagaacatgg   6480
cggtagggcc tacaggcatg cagtggagga actaccagaa acgatggaaa cactcttact   6540
cctgggactg atgatcttgt taacaggtgg agcaatgctc ttcttgatat caggtaaagg   6600
gattggaaag acttcaatag gactcatttg tgtaattgct tccagcggca tgttatggat   6660
ggctgatgtc ccactccaat ggatcgcatc ggctatagtc ctggagtttt ttatgatggt   6720
gttgctcata ccagaaccag aaaagcagag aactccccaa gacaaccaac tcgcatatgt   6780
cgtgataggc atacttacat tggctgcaat agtagcggcc aatgaaatgg gactgttgga   6840
```

-continued

```
aactacaaag agagatttag gaatgtctaa agaaccaggt gttgtttctc caaccagcta   6900
tttggatgtg gacttgcacc cagcatcagc ctggacattg tacgccgtgg ccacaacagt   6960
aataacacca atgttgagac acaccataga gaattccaca gcaaatgtgt ctctggcagc   7020
catagctaac caggcagtgg tcctgatggg tttagacaaa ggatggccga tatcgaaaat   7080
ggacttgggc gtaccactat tggcactggg ttgctattca caagtgaacc cactaactct   7140
tgcagcggca gtacttttgc tagtcacaca ttatgcaatt ataggtccag gattgcaggc   7200
aaaagccacc cgtgaagctc agaaaaggac agctgctgga ataatgaaga atccaacggt   7260
ggatggaata atgacaatag acctagatcc tgtaatatat gattcaaaat ttgaaaagca   7320
actaggacag gtcatgctcc tggttctgtg tgcagtccaa cttttattga tgagaacatc   7380
atgggccttg tgtgaagttc taaccctagc cacaggacca ataacaacac tctgggaagg   7440
atcacctggg aagttctgga acaccacgat agctgtttcc atggcgaaca tctttagagg   7500
gagctattta gcaggagctg ggcttgcttt ttctatcatg aaatcagttg gaacaggaaa   7560
gagaggaaca gggtcacaag gtgaaacctt aggagaaaag tggaaaaaga aattaaatca   7620
gttatcccgg aaagagtttg acctttacaa gaaatccgga atcaccgaag tggatagaac   7680
agaagccaaa gaagggttaa aaagaggaga aataacacac catgccgtgt ccagaggcag   7740
cgcaaaactt caatggttcg tggagagaaa catggtcatt cctgaaggaa gagtcataga   7800
cctaggctgt ggaagaggag gctggtcata ttactgtgca ggactgaaaa aagttacaga   7860
agtgcgagga tacacaaaag gcggcccagg acacgaagaa ccagtaccta tgtctacata   7920
cggatggaac atagtcaagt taatgagtgg aaaggatgtt ttttatctgc cacctgaaaa   7980
gtgtgatacc ctattgtgtg acattggaga atcttcacca agcccaacag tggaagaaag   8040
cagaaccata agagttttga agatggttga accatggcta aagaacaacc agttttgcat   8100
taaagtattg aacccataca tgccaactgt gattgagcac ttagaaagac tacaaaggaa   8160
acatggagga atgcttgtga gaaatccact ctcacgaaac tccacgcacg aaatgtattg   8220
gatatccaat ggtacaggca atatcgtctc ttcagtcaac atggtatcca gattgctact   8280
gaacagattc acaatgacac acaggagacc caccatagag aaagatgtgg atctaggagc   8340
aggaacccga catgtcaatg cggaaccaga aacacccaac atggatgtca ttggggaaag   8400
aataaaaagg atcaaagagg agcatagttc aacatggcac tatgatgatg aaaatcctta   8460
caaaacgtgg gcttaccatg gatcctatga agtaaaagcc acaggctcag cctcctccat   8520
gataaatgga gtcgtgaaac tcctcacaaa accatgggat gtggtgccca tggtgacaca   8580
gatggcaatg acagatacaa ctccattcgg ccagcaaaga gtttttaaag agaaagtgga   8640
caccaggaca cctaggccca tgccaggaac aagaaaggtt atggagatca cagcggagtg   8700
gctttggagg accctgggaa ggaacaaaag acccagatta tgcacaaggg aggaattcac   8760
aaagaaggtc agaaccaacg cagctatggg cgctgtcttc acagaagaga accaatggga   8820
cagtgcgaga gctgctgttg aggacgaaga attttggaaa cttgtggaca gagaacgtga   8880
actccacaaa ctgggcaagt gtggaagctg cgtttacaac atgatgggca agagagagaa   8940
aaaacttgga gagtttggta aagcaaaagg cagtagggct atatggtaca tgtggttggg   9000
agccaggtac cttgagttcg aggcgctcgg attcctcaat gaagaccact ggttctcgcg   9060
tgaaaactct tacagtggag tagaaggaga aggactgcac aagctgggat acatcttgag   9120
agatatttcc aagatacccg gaggagccat gtatgctgat gacacagccg gttgggacac   9180
```

-continued

```
aagaataaca gaagatgacc tgcacaatga ggaaaaaatc acacagcaga tggaccctga   9240

acacaggcag ctagcgaacg ctatattcaa gctcacatac caaaacaaag tggtcaaagt   9300

ccaacgacca actccaaagg gcacggtaat ggacatcata tctaggaaag accaaagagg   9360

cagtggacag gtgggaactt atggtctgaa cacattcacc aacatggaag cccagctaat   9420

cagacaaatg gaaggagaag gcgtgttgtc aaaggcagac ctcgagaacc cccatccgct   9480

agagaagaaa attacacaat ggttggaaac taaaggagtg gaaaggttaa aaagaatggc   9540

catcagcggg gatgattgcg ttgtgaaacc aatcgacgac agattcgcca atgccctgct   9600

tgccctgaac gatatgggaa aggttagaaa ggacatacct caatggcagc catcaaaggg   9660

atggcatgat tggcaacagg tccccttctg ctcccaccac tttcatgaat tgatcatgaa   9720

agatggaaga aagttggtag ttccctgcag accccaggac gaactaatag gaagagcgag   9780

aatctcccaa ggagcaggat ggagccttag agaaactgca tgtctaggga aagcctacgc   9840

tcaaatgtgg gctctcatgt attttcacag aagagatctt agactagcat ccaacgccat   9900

atgttcagca gtaccagtcc actgggtccc cacgagcaga acgacatggt ctattcatgc   9960

tcaccatcag tggatgacta cagaagacat gcttactgtc tggaacaggg tgtggataga  10020

ggacaatcca tggatggaag acaaaactcc agtcacaacg tgggaagatg ttccatatct  10080

agggaagaga gaagaccaat ggtgcggatc actcataggt ctcacttcca gagcaacctg  10140

ggcccagaac atactcacag caatccaaca ggtgagaagc ctcataggca atgaagagtt  10200

tctggactac atgccttcga tgaagagatt caggaaggag gaggagtcag agggagccat  10260

ttggtaaaag caggaggtaa actgtcaggc cacattaagc cacagtacgg aagaagctgt  10320

gcagcctgtg agccccgtcc aaggacgtta aaagaagaag tcaggcccaa aagccacggt  10380

ttgagcaaac cgtgctgcct gtagctccgt cgtggggacg taaagcctgg gaggctgcaa  10440

accgtggaag ctgtacgcac ggtgtagcag actagtggtt agaggagacc cctcccatga  10500

cacaacgcag cagcggggcc cgagcactga gggaagctgt acctccttgc aaaggactag  10560

aggttagagg agaccccccg caaacaaaaa cagcatattg acgctgggag agaccagaga  10620

tcctgctgtc tcctcagcat cattccaggc acagaacgcc agaaaatgga atggtgctgt  10680

tgaatcaaca ggttctagt                                                10699
```

```
<210> SEQ ID NO 42
<211> LENGTH: 10648
<212> TYPE: DNA
<213> ORGANISM: Dengue virus
<220> FEATURE:
<221> NAME/KEY: misc_feature
<222> LOCATION: (1)..(10648)
<223> OTHER INFORMATION: LAV4

<400> SEQUENCE: 42
```

```
agttgttagt ctgtgtggac cgacaaggac agttccaaat cggaagcttg cttaacacag     60

ttctaacagt ttgtttgaat agagagcaga tctctggaaa aatgaaccaa cgaaaaaagg    120

tggttagacc acctttcaat atgctgaaac gcgagagaaa ccgcgtatca accccctcaag    180

ggttggtgaa gagattctca accggacttt tttctgggaa aggaccctta cggatggtgc    240

tagcattcat cacgtttttg cgagtccttt ccatcccacc aacagcaggg attctgaaaa    300

gatggggaca gttgaagaaa aataaggcca tcaggatact gattggattc aggaaggaga    360

taggccgcat gctgaacatc ttgaacggga gaaaaaggtc aacgataaca ttgctgtgct    420

tgattcccac cgtaatggcg tttcacttgt caacaagaga tggcgaaccc ctcatgatag    480
```

-continued

```
tggcaaaaca tgaaaggggg agacctctct tgtttaagac aacagagggg atcaacaaat    540
gcactctcat tgccatggac ttgggtgaaa tgtgtgagga cactgtcacg tataaatgcc    600
ccttactggt caataccgaa cctgaagaca ttgattgctg gtgcaatctc acgtctacct    660
gggtcatgta tgggacatgc acccagagcg gagaacggag acgagagaag cgctcagtag    720
ctttaacacc acattcagga atgggattgg aaacaagagc tgagacatgg atgtcatcgg    780
aaggggcttg gaagcatgct cagagagtag agagctggat actcagaaac ccaggattcg    840
cgctcttggc aggatttatg gcttatatga ttgggcaaac aggaatccag cgaactgtct    900
tctttgtcct aatgatgctg gtcgccccat cctacggaat gcgatgcgta ggagtaggaa    960
acagagactt tgtggaagga gtctcaggtg gagcatgggt cgatctggtg ctagaacatg   1020
gaggatgcgt cacaaccatg gcccagggaa aaccaacctt ggattttgaa ctgactaaga   1080
caacagccaa ggaagtggct ctgttaagaa cctattgcat tgaagcctca atatcaaaca   1140
taaccacggc aacaagatgt ccaacgcaag gagagcctta tctaaaagag gaacaagacc   1200
aacagtacat ctgccggaga gatgtggtag acagagggtg gggcaatggc tgtggcttgt   1260
ttggaaaagg aggagttgtg acatgtgcga agttttcatg ttcggggaag ataacaggca   1320
atttggtcca aattgagaac cttgaataca cagtggttgt aacagtccac aatggagaca   1380
cccatgcagt aggaaatgac acatccaatc atggagttac agccacgata actcccaggt   1440
caccatcggt ggaagtcaaa ttgccggact atggagaact aacactcgat tgtgaaccca   1500
ggtctggaat tgactttaat gagatgattc tgatgaaaat gaaaaagaaa acatggcttg   1560
tgcataagca atggtttttg gatctacctc taccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatctcaag tgcaaagtcc   1800
gtatggagaa attgagaatc aagggaatgt catacacgat gtgttcagga aagttctcaa   1860
ttgacaaaga gatggcagaa acacagcatg ggacaacagt ggtgaaagtc aagtatgaag   1920
gtgctggagc tccgtgtaaa gtccccatag agataagaga tgtgaacaag aaaaaagtgg   1980
ttgggcgtat catctcatcc accccctttgg ctgagaatac caacagtgca accaacatag   2040
agttagaacc cccctttggg gacagctaca tagtgatagg tgttggaaac agtgcattaa   2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggtttttgg aagtgtgtat acaaccatgt   2280
ttggaggagt ctcatggatg attagaatcc taattgggtt cctagtgttg tggattggca   2340
cgaactcaag gaacacttca atggctatga cgtgcatagc tgttggagga atcactctgt   2400
ttctgggctt cacagttcaa gcagacatgg gttgtgtggt gtcatggagt gggaaagaat   2460
tgaagtgtgg aagcggaatt tttgtggttg acaacgtgca cacttggaca gaacagtaca   2520
aatttcaacc ggagtcccca gcgagactag cgtctgcaat attgaatgcc cacaaagatg   2580
ggtctgtgg aattagatca accacgaggc tggaaaatgt catgtggaag caaataacca   2640
acgagctaaa ttatgttctc tgggaaggag gacatgacct cactgtagtg gctggggatg   2700
tgaagggggt gttgaccaaa ggcaagagag cactcacacc cccagtgaat gatctgaaat   2760
attcatggaa gacatgggga aaagcaaaaa tcttcacccc agaagcaaga aatagcacat   2820
```

-continued

```
ttttaataga cggaccagac acctccgaat gccccaatga acgaagagca tggaactttc   2880

ttgaggtgga agactatgga tttggcatgt tcacgaccaa catatggatg aaattccgag   2940

aaggaagttc agaagtgtgt gaccacaggt taatgtcagc ggcaattaaa gatcagaaag   3000

ctgtgcatgc tgacatgggt tattggatag agagctcaaa aaaccagacc tggcagatag   3060

agaaagcatc tcttattgaa gtgaaaacat gtctgtggcc caagacccac acattgtgga   3120

gcaatggagt gctggaaagc cagatgctca ttccaaaatc atatgcgggc cctttttcac   3180

accacaatta ccgccagggc tatgccacgc aaaccgtggg cccatggcac ttaggcaaat   3240

tagagataga ctttggagaa tgccccggaa caacagtcgc aattcaggag gattgtgacc   3300

atagaggccc atctttgagg accaccactg catctggaaa actagtcacg caatggtgct   3360

gccgctcctg cacgatgcct cccttaaggt tcttgggaga agatgggtgc tggtatggga   3420

tggagattag gcccttgagt gaaaaagaag agaacatggt caaatcacag gtaacggccg   3480

gacagggcac atcagaaact tttctatgg  gtctgttgtg cctgaccttg tttgtggaag   3540

aatgcttgag gagaagagtc actaggaaac acatgatatt ggttgtggtg atcactcttt   3600

gtgccatcat cctaggaggc ctcacatgga tggacttact acgagccctc atcatgttgg   3660

gggacactat gtctggtaga ataggaggac agatccacct agccatcatg gcagtgttca   3720

agatgtcacc aggatacgtg ctgggtgtgt ttttaaggaa actcacttca agagagacag   3780

cactaatggt aataggaatg gccatgacaa cggtgctttc aattccacat gaccttatgg   3840

aactcattga tggaatatca ctggggctaa ttttgctaaa aatagtgaca cattttgaca   3900

acacccaagt gggaacctta gccctttcct tgaccttcat aagatcaaca atgccattgg   3960

tcatggcttg gaggaccatt atggctgtgt tgtttgtggt cacactcatt cctttgtgca   4020

ggacaagctg tcttcaaaaa cagtctcatt gggtagaaat aacagcactc atcctaggag   4080

cccaagctct gccagtgtac ctaatgactc ttatgaaagg agcctcaaga agatcttggc   4140

ctcttaacga gggcataatg gctgtgggtt tggttagtct cttaggaagc gctcttttaa   4200

agaatgatgt ccctttagct ggcccaatgg tggcaggagg cttacttctg gcggcttacg   4260

tgatgagtgg tagctcagca gatctgtcac tagagaaggc cgccaatgtg cagtgggatg   4320

aaatggcaga cataacaggc tcaagcccaa tcatagaagt gaagcaggat gaagatggct   4380

ctttctccat acgggacgtc gaggaaacca atatgataac ccttttggtg aaactggcac   4440

tgataacagt gtcaggtctc taccccttgg caattccagt cacaatgacc ttatggtaca   4500

tgtggcaagt gaaaacacaa agatcaggag ccctgtggga cgtcccctca cccgctgcca   4560

ctcaaaaagc cgcactgtct gaaggagtgt acaggatcat gcaaagaggg ttatttggga   4620

aaactcaggt tggagtaggg atacacatgg aaggtgtatt tcacacaatg tggcatgtaa   4680

caagaggatc agtgatctgc catgagactg ggagattgga gccatcttgg gctgacgtca   4740

ggaatgacat gatatcatac ggtgggggat ggagacttgg agacaaatgg gacaaagaag   4800

aagatgttca ggtcctcgcc atagaaccag gaaaaaatcc taaacatgtc caaacgaaac   4860

ccggcctttt caagacccta actggagaaa ttggagcagt aacattagat ttcaaacccg   4920

gaacgtctgg ttctcccatc atcaacagga aaggaaaagt catcggactc tatggaaatg   4980

gagtagttac caaatcaggt gattacgtca gtgccataac gcaagccgaa agaattggag   5040

agccagatta tgaagtggat gaggacattt ttcgaaagaa aagattaact ataatggact   5100

tacaccccgg agctggaaag acaaaaagaa ttcttccatc aatagtgaga gaagccttaa   5160

aaaggaggct gcgaaccttg attttggctc ccacgagagt ggtggcggcc gagatggaag   5220
```

-continued

```
aggccctacg tggactgcca atccgttatc agaccccagc tgtgaaatca gaacacacag   5280
gaagagagat tgtagacctc atgtgtcatg caaccttcac aacaagactt ttgtcatcaa   5340
ccagagttcc aaattacaac ctcatagtga tggatgaagc acatttcacc gatccttcta   5400
gtgtcgcggc tagaggatac atctcgacca gggtggaaat gggagaggca gcagccatct   5460
tcatgaccgc aacccctccc ggagcgacag atccctttcc ccagagcaac agcccaatag   5520
aagacatcga gagggaaatt ccggaaaggt catggaacac agggttcgac tggataacag   5580
actaccaagg gaaaactgtg tggtttgttc ccagcataaa agctggaaat gacattgcaa   5640
attgtttgag aaagtcggga aagaaagtta tccagttgag taggaaaacc tttgatacag   5700
agtatccaaa aacgaaactc acggactggg attttgtggt cactacagac atatctgaaa   5760
tgggggccaa ttttagagct gggagagtga tagaccctag gagatgcctc aagccagtta   5820
tcctaacaga tgggccagag agagtcattt tagcaggtcc tattccagtg actccagcaa   5880
gcgctgctca gagaagaggg cgaataggaa ggaacccagc acaagaagac gaccaatacg   5940
ttttctccgg agacccacta aaaaatgatg aagatcatgc ccactggaca gaagcaaaga   6000
tgctgcttga caatatctac accccagaag ggatcattcc aacattgttt ggtccggaaa   6060
gggaaaaaac ccaagccatt gatggagagt ttcgcctcag aggggaacaa aggaagactt   6120
ttgtggaatt aatgaggaga ggagaccttc cggtgtggct gagctataag gtagcttctg   6180
ctggcatttc ttacaaagat cgggaatggt gcttcacagg ggaaaggaat aaccaaattt   6240
tagaagaaaa catggaggtt gaaatttgga ctagagaggg agaaaagaaa aagctaaggc   6300
caagatggtt agatgcacgt gtatacgctg accccatggc tttgaaggat tttaaggagt   6360
ttgctagtgg aaggaagagc ataactctcg acatcctaac agagattgcc agtttgccaa   6420
cttacctttc ctctagggcc aagctcgccc ttgataacat agtcatgctc cacacaacag   6480
aaagaggagg gagggcctac caacacgccc tgaacgaact cccggagtca ctggaaacac   6540
ttatgcttgt agctttacta ggtgctatga cagcaggtat cttcctgttt ttcatgcaag   6600
ggaaaggaat agggaaattg tcaatgggtt tgataaccat tgcggtggct agtggcttgt   6660
tctgggtagc agaaattcaa ccccagtgga tagcggcctc aatcatacta gagtttttc    6720
tcatggtact gttgataccg gaaccagaaa aacaaaggac ccccacaagac aatcaattga  6780
tctacgtcat attgaccatt ctcaccatta ttggtctcat agcagccaac gagatggggc   6840
tgattgaaaa aacaaaaacg gattttgggt tttaccaggt aaaaacagaa accaccatcc   6900
tcgatgtgga cttgagacca gcttcagcat ggacgctcta tgcagtagcc accacawttc   6960
tgactcccat gctgagacac accatagaaa acacgtcggc caacctatct ctagcagcca   7020
ttgccaacca ggcggccgtc ctaatggggc ttggaaaagg atggccgctc cacagaatgg   7080
acctcggtgt gccgctgtta gcaatgggat gctattctca agtgaaccca acaactttga   7140
cagcatcctt agtcatgctt tcagtccatt atgcaataat aggtccagga ttgcaggcaa   7200
aagccacaag agaggcccag aaaaggacag ctgctgggat catgaaaaac cccacggtgg   7260
acgggataac agtaatagat ctagaaccaa tatcctatga cccaaaattt gaaaagcaat   7320
tagggcaggt catgctactc gtcttgtgtg ctggacaact actcttgatg agaacaacat   7380
gggctttctg tgaagtcttg actttggcca caggaccaat cttgaccttg tgggagggca   7440
acccgggaag gttttggaac acgaccatag ccgtatccac cgccaacatt ttcaggggaa   7500
gttacctggc gggagctgga ctggcttttt cactcataaa gaatgyacaa acccctagga   7560
```

-continued

```
ggggaactgg gaccacagga gagacactgg gagagaagtg gaagagacag ctaaactcat   7620
takacagaaa agagtttgaa gagtataaaa gaagtggaat actagaagtg gacaggactg   7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
tgaaagggta tacaaaagga ggtccaggac atgaagaacc gattcccatg gctacttatg   7920
gctggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taacccctac atgccaacag tcatagaaga gctggagaaa ctgcagagaa   8160
aacatggtgg gaaccttgtc agatgcccgc tgtccaggaa ctccacccat gagatgtatt   8220
gggtgtcagg agcgtcggga aacattgtga gctctgtgaa cacaacatca aagatgttgt   8280
tgaacaggtt cacaacaagg cataggaaac ccacttatga gaaggacgta gatcttgggg   8340
caggaacgag aagtgtctcc actgaaacag aaaaaccaga catgacaatt attgggagaa   8400
ggcttcagcg attgcaagag gagcacaaag aaacctggca ttatgatcag gaaaacccat   8460
acagaacctg ggcgtatcat ggaagctatg aagctccttc gacaggctct gcatcctcca   8520
tggtgaacgg ggtagtaaaa ctgctaacaa aaccttggga tgtggttcca atggtgaccc   8580
agttagccat gacagacaca accccttttg ggcaacaaag agtgttcaaa gagaaggtgg   8640
ataccagaac accacaacca aaacccggta cacgaatggt tatgaccacg acagccaatt   8700
ggctgtgggc cctccttggg aagaagaaaa atcccagact gtgcacaagg gaagagttca   8760
tctcaaaagt tagatcaaac gcagccatag gcgcagtctt tcaggaagaa cagggatgga   8820
catcagccag tgaagctgtg aatgacagcc ggttttggga actggttgac aaagaaaggg   8880
ccctacacca ggaagggaaa tgtgaatcgt gtgtctacaa catgatggga aaacgtgaga   8940
aaaagttagg agagtttggc agagccaagg gaagccgagc aatctggtac atgtggctgg   9000
gagcgcggtt tctggaattt gaagccctgg gtttttttgaa tgaagatcac tggtttggca   9060
gagaaaattc atggagtgga gtggaagggg aaggtctgca cagattggga tatatcctgg   9120
aggagataga caagaaggat ggagacctaa tgtatgctga tgacacagca ggctgggaca   9180
caagaatcac tgaggatgac cttcaaaatg aagaactgat cacggaacag atggcccccc   9240
accacaagat cctagccaaa gccattttca aactaaccta tcaaaacaaa gtggtgaaag   9300
tcctcagacc cacaccgaga ggagcggtga tggatatcat atccaggaaa gaccaaagag   9360
gtagtggaca agttggaaca tatggtttga acacattcac caacatggaa gttcaactca   9420
tccgccaaat ggaagctgaa ggagtcatca cacaagatga catgcagaac ccaaaagggt   9480
tgaaagaaag agttgagaaa tggctgaaag agtgtggtgt cgacaggtta aagaggatgg   9540
caatcagtgg agacgattgc gtggtgaagc ccctggatga gaggtttggc acttccctcc   9600
tcttcttgaa cgacatggga aaggtgagga aagacattcc gcagtgggaa ccatctaagg   9660
gatggaaaaa ctggcaagag gttccttttt gctcccacca ctttcacaag atcttcatga   9720
aggatggccg ctcactagtt gttccatgta gaaaccagga tgaactgata gggagagcca   9780
gaatctcgca gggggctgga tggagcttaa gagaaacagc ctgcctgggc aaagcttacg   9840
cccagatgtg gtcgctcatg tacttccaca gaagggatct gcgtttagcc tccatggcca   9900
tatgctcagc agttccaacg gaatggtttc caacaagcag aacaacatgg tcaatccacg   9960
```

-continued

```
ctcatcatca gtggatgacc actgaagata tgctcaaagt gtggaacaga gtgtggatag  10020

aagacaaccc taatatgact gacaagactc cagtccattc gtgggaagat ataccttacc  10080

tagggaaaag agaggatttg tggtgtggat ccctgattgg actttcttcc agagccacct  10140

gggcgaagaa cattcacacg gccataaccc aggtcagaaa cctgatcgga aaagaggaat  10200

acgtggatta catgccagta atgaaaagat acagcgctcc ttcagagagt gaaggagttc  10260

tgtaattacc aacaacaaac accaaaggct attgaagtca ggccacttgt gccacggctt  10320

gagcaaaccg tgctgcctgt agctccgcca ataatgggag gcgtgaaatc cctagggagg  10380

ccatgcgcca cggaagctgt acgcgtggca tattggacta gcggttagag gagacccctc  10440

ccatcactga caaaacgcag caaaaggggg cccgaagcca ggaggaagct gtactcctgg  10500

tggaaggact agaggttaga ggagaccccc ccaacacaaa aacagcatat tgacgctggg  10560

aaagaccaga gatcctgctg tctctgcaac atcaatccag gcacagagcg aagcaagatg  10620

gattggtgtt gttgatccaa caggttct                                     10648
```